US012790372B2

(12) United States Patent
Pan

(10) Patent No.: US 12,790,372 B2
(45) **Date of Patent: *Nov. 10, 2026**

(54) IDENTIFICATION OF CHANNELRHODOPSIN-2 (CHR2) MUTATIONS AND METHODS OF USE

(71) Applicant: Wayne State University, Detroit, MI (US)

(72) Inventor: Zhuo-Hua Pan, Detroit, MI (US)

(73) Assignee: Wayne State University, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/639,381

(22) Filed: Apr. 18, 2024

(65) Prior Publication Data

US 2025/0066431 A1 Feb. 27, 2025

Related U.S. Application Data

(63) Continuation of application No. 17/202,064, filed on Mar. 15, 2021, now abandoned, which is a continuation of application No. 14/383,211, filed as application No. PCT/US2013/029171 on Mar. 5, 2013, now Pat. No. 10,947,281.

(60) Provisional application No. 61/606,663, filed on Mar. 5, 2012.

(51) Int. Cl.

| | |
|---|---|
| ***C07K 14/405*** | (2006.01) |
| ***A61K 38/16*** | (2006.01) |
| ***A61K 48/00*** | (2006.01) |
| ***A61P 27/02*** | (2006.01) |
| ***C07K 14/00*** | (2006.01) |

(52) U.S. Cl.

CPC ............ *C07K 14/405* (2013.01); *A61K 38/16* (2013.01); *A61P 27/02* (2018.01); *C07K 14/00* (2013.01); *A61K 48/00* (2013.01)

(58) Field of Classification Search

None

See application file for complete search history.

(56) References Cited

U.S. PATENT DOCUMENTS

| | | | |
|---|---|---|---|
| 4,498,919 | A | 2/1985 | Mann |
| 4,554,101 | A | 11/1985 | Hopp |
| 5,827,702 | A | 10/1998 | Cuthbertson |
| 6,610,287 | B1 | 8/2003 | Breakefield |
| 7,144,733 | B2 | 12/2006 | Miesenbock |
| 7,186,699 | B2 | 3/2007 | Harding |
| 7,427,138 | B2 | 9/2008 | Ellenbogen |
| 7,824,869 | B2 | 11/2010 | Hegemann |
| 8,470,790 | B2 | 6/2013 | Pan |
| 10,947,281 | B2 | 3/2021 | Pan |
| 2004/0022766 | A1 | 2/2004 | Acland |
| 2005/0202398 | A1 | 9/2005 | Hegemann |
| 2005/0208022 | A1 | 9/2005 | Masland |
| 2010/0015095 | A1 | 1/2010 | Pan |
| 2013/0259833 | A1 | 10/2013 | Pan |
| 2014/0121265 | A1 | 5/2014 | Pan |

FOREIGN PATENT DOCUMENTS

| | | | |
|---|---|---|---|
| WO | 1998048027 | A2 | 10/1998 |
| WO | 0015822 | A1 | 3/2000 |
| WO | 0183692 | A2 | 11/2001 |
| WO | 2005044096 | A2 | 5/2005 |
| WO | 2007024391 | A2 | 3/2007 |
| WO | 2007131180 | A2 | 11/2007 |
| WO | 2011140279 | A1 | 11/2011 |
| WO | 2012032103 | A1 | 3/2012 |
| WO | 2013134295 | A1 | 9/2013 |

OTHER PUBLICATIONS

Acland, G.M. et al., "Gene Therapyy Restores Vision in a Canine Model of Childhood Blindness," Nat. Genet., vol. 28, pp. 92-95 (2001 ). Abstract.

Ali, R.R. et al., "Restoration of Photoreceptor Ultrastructure and Function in Retinal Degeneration Slow Mice by Gene Therapy," Nat. Genet., vol. 25, pp. 306-310 (2000). Abstract.

Banghart, M. et al., "Light-activated ion channels for remote control of neuronal firing," Nat. Neurosci., vol. 7, pp. 1381-1386 (2004).

Baylor, D., "How Photons Start Vision," Proc. Natl. Acad. Sci. USA, vol. 93, pp. 560-565(1996).

Bennett, J. et al., "Photoreceptor cell rescue in retinal degeneration (rd) mice by in vivo gene therapy," Nat. Med., vol. 2, pp. 649-654 (1996). ,Abstract.

Bennett, J. et al., "Adenovirus-mediated delivery of rhodopsin-promoted bcl-2 results in a delay in photoreceptor cell death in the rd/rd mouse," Gene Therapy vol. 5, pp. 1156-1164 (1998).

Bennett, Jet al., "Stable transgene expression in rod photoreceptors afterrecombinant adeno-associated virus-mediated gene transfer to monkey retina," Proc. Natl. Acad. Sci. USA, vol. 96, pp. 9920-9925 (1999).

Berndt, A et al., "High-efficiency channelrhodopsins for fast neuronal stimulation at low light levels," Proceedings of the National Academy of Sciences, vol. 108, No. 18, May 3, 2011, pp. 7595-7600.

Kleinlogel, Sonja., et al., "Ultra light-sensitive and fast neuronal activation with the Ca2+-permeable channelrhodopsin CatCh," Nature Neuroscience, vol. 14, No. 4, Mar. 13, 2011, pp. 513-518.

Martin L. Rein et al., "The optogenetic (r)evolution," Molecular Genetics and Genomics, Springer, Berlin, DE, Dec. 20, 2011, vol. 287, No. 2, pp. 95-109.

NCBI Blast Protein Comparison between WO2012/032103 SEQ ID No. 1 and claimed SEQ ID No. 26, 2 pages (conducted on May 12, 2016).

Vimont, C., https://www.aao.org/eye-health/tips-prevention/what-does-20-20-vision-mean, 5 pages (2020) (Year: 2020).

(Continued)

*Primary Examiner* — Thea D'Ambrosio

(74) *Attorney, Agent, or Firm* — KDW Firm PLLC

(57) ABSTRACT

The invention provides compositions and kits including at least one nucleic acid or polypeptide molecule encoding for a mutant ChR2 protein. Methods of the invention include administering a composition comprising a mutant ChR2 to a subject to preserve, improve, or restore phototransduction. Preferably, the compositions and methods of the invention are provided to a subject having impaired vision, thereby restoring vision to normal levels.

13 Claims, 6 Drawing Sheets

Specification includes a Sequence Listing.

(56) References Cited

OTHER PUBLICATIONS

Zhuo-Hua Pan et al: "ChR2 Mutants at L 132 and TI59 with Improved Operational Light Sensitivity for Vision Restoration", PLoS ONE, vol. 9, No. 6, Jun. 5, 2014, p. e98924, (12 pages).
"Translation Study Guide," available online at https://depts.washing.edu/hhmibio/translationStudyGuide.pdf , 9 pages (first available 2004).
Ivanova et al., "Evaluation of AAV-Mediated Expression of Chop2-GFP in the Marmoset Retina," Investigative Opthamology & Visual Science, vol. 51, No. 10: 5288-5296 (Oct. 2010).
Prigge et al., "Color-tuned Channelrhodopsins for Multiwavelength Optogenetics," Journal of Biological Chemistry, vol. 287, No. 38: 31804-31812 (Jul. 27, 2012).
Ullrich et al., "Degradation of channelopsin-2 in the absence of retinal and degradation resistance in certain mutants," Biological Chemistry, vol. 394, No. 2: 271-280 (Feb. 2013).
Zhang et al., "The Microbial Opsin Family of Optogenetic Tools," Cell, vol. 147, No. 7: 1446-1457 (Nov. 23, 2011).
Berson, "Phototransduction in Ganglion-Cell Photoreceptors," Eur. J. Physiol., vol. 454: 849-855 (2007).
Bi et al., "Ectopic expression of a microbial-type rhodopsin restores visual responses in mice with photoreceptor degeneration," Neuron, vol. 50: 23-33 (2006)—Abstract.
Borras, "Recent Developments in Ocular Gene Therapy," Exp. Eye Res., vol. 76: 643-562 (2003)—Abstract.
Casini et al., "Developmental Expression of Neurokinin-1 and Neurokinin-3 Receptors in the Rat Retina," J. Comp. Neurol., vol. 421: 275-287 (2001)—Abstract.
Chang et al., "Retinal Degeneration Mutant in the Mouse," Vision Res., vol. 42: 517-525 (2002).
Communication Pursuant to Article 94(3) EPC issued by the European Patent Office for Application No. EP07797340.2, dated Sep. 25, 2014, 5 pages.
Flannery et al., "Looking Within for Vision," Neuron, vol. 50(1): 3 pages (2006)—Abstract.
Flannery et al., "Efficient Photoreceptor-targeted gene expression in vivo by recombinant adeno-associated virus," Proc. Natl. Acad. Sci. USA, vol. 94: 6916-6921 (1997).
Greenberg et al., "In vivo Transgene Expression in ON-Type Retinal Ganglion Cells: Application to Retinal Disease," ARVO (2007)—Abstract.
Hankins et al., "Melanopsin: An Exciting Photopigment," Trends Neurosci., vol. 31(1): 27-36 (2007)—Abstract.
Hauswirth, "The Consortium Project to Treat RPE65 Deficiency in Humans," Retina, vol. 25: 60 (2005).
Hauswirth et al., "Ocular Gene Therapy: Quo Vadis?," Invest. Ophthal. Vis. Sci., vol. 41(10): 2821-2826 (2000).
Haverkamp et al., "Immunocytochemical Description of Five Bipolar Cell Types of the Mouse Retina," J Comp. Neurol., vol. 455(4): 463-476 (2003).
Hossain et al., "Artificial Means for Restoring Vision," Brit. Med. J., vol. 330: 30-33 (2005).
Humphries et al., "On the Molecular Genetics of Retinitis Pigmentosa," Science, vol. 256: 804-808 (1992)—Abstract.
International Preliminary Report on Patentability and Written Opinion of the International Searching Authority for PCT/US2007/068263, dated May 15, 2008, 6 pages.
International Search Report issued by the International Searching Authority for PCT/US2007/068263, dated May 15, 2008, 4 pages.
International Preliminary Report on Patentability and Written Opinion of the International Searching Authority for PCT/US2011/035266, dated Nov. 6, 2012, 5 pages.
International Search Report of the International Searching Authority for PCT/US2011/035266, dated Jul. 27, 2011, 4 pages.
International Preliminary Report on Patentability and Written Opinion of the International Searching Authority for PCT/US2013/029171, dated Sep. 9, 2014, 12 pages.
Ishizuka et al., "Kinetic Evaluation of Photosensitivity in Genetically Engineered Neurons Expressing Green Algae Light-Gated Channels," Neurosci. Res., vol. 54: 85-94 (Nov. 17, 2005).
Jacobson, "Discussion of Human Gene Transfer Protocol #0410-677: Phase I Trial of Ocular Subretinal Injection of a Recombinant Adeno-Associated Virus (rAAV-RPE65) Gene Vector in Patients with Retinal Disease due to RPE65 Mutations," National Institutes of Health Recominant DNA Advisory Committee (RAC) Meeting Jun. 15-16, 2005, 47 pages.
Kay et al., "Viral Vectors for Gene Therapy: The Art of Turning Infectious Agents into Vehicles of Therapeutics," Nat. Med. vol. 7: 33-40 (2001)—Abstract.
Kumar-Singh et al., "Encapsidated adenovirus mini-chromosome-mediated delivery of genes to the retina: application to the rescue of photoreceptor degeneration," Hum. Mol. Genet., vol. 7: 1893-10 (1998).
Lanyi , "Bacteriorhodopsin," Ann. Rev. Physiol., vol. 66: 665-688 (2004).
Lanyi, "Halorhodopsin, a Light-Driven Electrogenic Chloride-Transport System," Physiol. Rev., vol. 70(2): 319-330 (1990).
Lau et al., "Retinal Degeneration is Slowed in Transgenic Rats by AAV-Mediated Delivery of FGF-2," Invest. Ophthalmol. Vis. Sci., vol. 41: 3622-3622 (2000).
Lavail et al., "Ribozyme rescue of photoreceptor cells in P23H transgenic rats: Long-term survival and late-stage therapy," Proc. Natl. Proc. Natl. Acad. Sci. USA, vol. 97: 11488-11493 (2000).
Lavail et al., "Multiple growth factors, cytokines, and neurotrophins rescue photoreceptors from the damaging effects of constant light," Proc. Natl. Acad. Sci. USA, vol. 89: 11249-11253 (1992).
Lewin et al., "Ribozyme Rescue of photoreceptor cells in a transgenic rat model of autosomal dominant retinitis pigmentosa," Nat. Med., vol. 4: 967-971 (1998).
Lin et al., "Restoration of visual function in retinal degeneration mice by ectopic expression of melanopsin," Proc. Natl. Acad. Sci. USA, vol. 105: 16009-16014 (2008).
McFarland et al., "Gene therapy for proliferative ocular diseases," Exp. Opin. Biol. Ther., vol. 4(7): 1053-1058 (2004).
Han et al., "Multiple-color optical activation, silencing, and desynchronization of neural activity, with single-spike temporal resolution," PLoS ONE, vol. 2(3): e299 (2007).
Medeiros et al., "Preservation of ganglion cell layer neurons in age-related macular degeneration," Invest. Ophthal. Vis. Sci., vol. 42(3): 795-803 (2001).
Melyan et al., "Addition of human melanopsin renders mammalian cells photoresponsive," Nature, vol. 433: 741-745 (2005).
Milam et al., "Histopathology of the Human Retina in Retinitis Pigmentosa," Prog. Retin. Eye Res., vol. 17: 175-205 (1998).
Nagel et al., "Channelrhodopsin-1: A light-Gated Proton Channel in Green Algae," Science, vol. 296: 2395-2398 (2002).
Nagel et al., "Channelrhodopsin-2, a Directly light-gated cation-selective membrane channel," Proc. Natl. Acad. Sci. USA, vol. 100(24): 13940-13945 (2003).
Nakajima et al., "Molecular Characterization of a Novel Retinal Metabotropic Glutamate Receptor mGluR6 with a High Agonist Selectivity for L-2-Amino-4-phosphonobutyrate," J. Biol. Chem., vol. 268: 11868-11873 (1993).
Oesterhelt et al., "Functions of a New Photoreceptor Membrane," Proc. Natl. Acad. Sci. USA, vol. 70: 2853-2857 (1973).
Oesterhelt, "The structure and mechanism of the family of retinal proteins from halophilic archaea," Curr. Opin. Struct. Biol., vol. 8: 489-500 (1998).
Office Action issued by the United States Patent and Trademark Office for U.S. Appl. No. 13/899,198, dated Jul. 21, 2014, 20 pages.
Office Action issued by the United States Patent and Trademark Office for U.S. Appl. No. 12/299,574, dated Aug. 28, 2012, 15 pages.
Office Action issued by the United States Patent and Trademark Office for U.S. Appl. No. 12/299,574, dated Jan. 12, 2012, 10 pages.
Olshevskaya, EV et al. , "The Y99C Mutation in Guanylyl Cyclase-Activating Protein 1 Increases Intracellular Ca2 and Causes Photoreceptor Degeneration in Transgenic Mice," J. Neurosci. vol. 24, 2004, pp. 6078-6085.
Pan et al., "Functional expression of a directly light-gated membrane channel in mammalian retinal neurons: A potential strategy

(56) References Cited

OTHER PUBLICATIONS for restoring light sensitivity to the retina after photoreceptor degeneration" Investigative Ophthalmology Visual Science 46:E-Abstract 4631 (2005)—Abstract.
Panda et al., "Illumination of the Melanopsin Signaling Pathway," Science, vol. 307: 600-604 (2005).
Qiu et al., "Induction of photosensitivity by heterologous expression of melanopsin," Nature, vol. 433: 745-749 (2005).
Reutsky et al. "Patterned Optical Activation of Channelrhodopsin II Expressing RetinalGanglion Cells." Proc. 3rd Int. IEEE EMBS Cont. Neural Engin. (2007) :50-52.
Santos, AH et al., "Preservation of the Inner Retina in Retinitis Pigmentosa," Arch. Ophthalmol. vol. 115: 511-515 (1997).
Sineshchekov et al., "Two rhodopsins mediate phototaxis to low- and high-intensity light in Chlamydomonas reinhardtii," Proceedings of the National Academy of Sciences of the United States of America, vol. 99: 8689-8694 (2002).
Sung et al., "Rhodopsin mutations in autosomal dominant retinitis pigmentosa," Proceedings of the National Academy of Sciences of the United States of America, vol. 88: 6481-6485 (1991).
Supplementary European Search Report issued by the European Patent Office for Application No. EP07797340.2, dated Oct. 27, 2010, 7 pages.
Takahashi , M. et al. , "Rescue from Photoreceptor Degeneration in the rd Mouse by Human Immunodeficiency Virus Vector-Mediated Gene Transfer," J Virol. vol. 73, 1999, pp. 7812-7816.
Thyagarajan et al., "Visual Function in Mice with Photoreceptor Degeneration and Transgenic Expression of Channelrhodopsin 2 in Ganglion Cells," J Neurosci 2010; 30: 8745-5.
Tomita et al., "Channelrhodopsins provide a breakthrough insight into strategies for curing blindness," Journal of Genetics, 88:409-415 (2009).
Tomomura et al., "Purification of Purkinje cells by fluorescence-activated cell sorting from transgenic mice that express green fluorescent protein," European Journal of Neuroscience, vol. 14: 57-63 (2001).
Ueda et al., "The mGluR6 5 upstream transgene sequence directs a cell-specific and developmentally regulated expression in retinal cord and ON-type cone bipolar cells," Journal of Neuroscience, vol. 17: 3014-3023 (1997).
Veraart et al., "Vision Rehabilitation in the case of Blindness," Expert Rev. Medical Devices 1 (1):139-153 (2004)—Abstract.
Walther et al., "Viral Vectors for Gene Transfer a Review of Their Use in the Treatment of Human Diseases," Drugs, vol. 60: 249-271 (2000).
Wassle, "Parallel Processing in the Mammalian Retina," Nature Reviews Neuroscience, vol. 5: 747-757 (2004).
Zemelman et al., "Selective Photostimulation of Genetically Charged Neurons," Neuron, vol. 33: 15-22 (2002).
Zhang et al., "Multimodal fast optical interrogation of neural circuitry," Nature, vol. 446: 633-639 (2007).
Zrenner et al., "Will Retinal Implants Restore Vision" Science, vol. 295(1): 022-025 (2002).

IDENTIFICATION OF CHANNELRHODOPSIN-2 (CHR2) MUTATIONS AND METHODS OF USE

CROSS-REFERENCE TO RELATED APPLICATIONS

This application is a continuation application of U.S. patent application Ser. No. 17/202,064, filed Mar. 15, 2021, which is a continuation of and claims the benefit of U.S. patent application Ser. No. 14/383,211 filed Sep. 5, 2014, now U.S. Pat. No. 10,947,281 issued Mar. 16, 2021, which is a national stage application filed under 35 U.S.C. § 371 of International Application No. PCT/US2013/029171 filed Mar. 5, 2013, which claims the benefit of and priority under 35 U.S.C. § 119(e) to U.S. Provisional Application No. 61/606,663, filed Mar. 5, 2012, the contents of which are incorporated by reference herein in their entireties.

GOVERNMENT SUPPORT

This invention was made with U.S. Government support under the National Institutes of Health/National Eye Institute grant NIH EY 17130. The Government has certain rights in the invention.

INCORPORATION BY REFERENCE OF SEQUENCE LISTING

The present application contains a sequence listing which has been submitted in XML format. The content of the computer readable XML file named "6065_0506C2_SequenceListing.xml", which was created on Apr. 18, 2024 and is 58.7 kilobytes in size, is hereby incorporated by reference in its entirety.

FIELD OF THE INVENTION

This invention relates generally to the field of molecular biology. Mutations in the Channelopsin-2 (Chop2) gene are identified. Compositions comprising a mutant Chop2 gene are used in therapeutic methods to improve and restore vision loss.

BACKGROUND OF THE INVENTION

The retina is composed of photoreceptors (or photoreceptor cells, rods and cones). Photoreceptors are highly specialized neurons that are responsible for phototransduction, or the conversion of light (in the form of electromagnetic radiation) into electrical and chemical signals that propagate a cascade of events within the visual system, ultimately generating a representation of our world.

Photoreceptor loss or degeneration severely compromises, if not completely inhibits, phototransduction of visual information within the retina. Loss of photoreceptor cells and/or loss of a photoreceptor cell function are the primary causes of diminished visual acuity, diminished light sensitivity, and blindness. There is a long-felt need in the art for compositions and method that restore photosensitivity of the retina of a subject experiencing vision loss.

SUMMARY OF THE INVENTION

The invention provides a solution for the long-felt need for a method of restoring and/or increasing the light sensitivity of photoreceptor cells by expression of advantageous mutations, and/or combinations thereof, of the Channelopsin-2 (Chop2) gene, and subsequently providing methods for Channelopsin-2 (Chop2)-based gene therapy.

Channelopsin-2 (Chop2)-based gene therapy offers a superior strategy for restoring retinal photosensitivity after photoreceptor degeneration. The protein product of the Chop2 gene, when bound to the light-isomerizable chromophore all-trans-retinal, forms a functional light-gated channel, called channelrhodopsin-2 (ChR2). Native ChR2 shows low light sensitivity. Recently, two mutant ChR2s, L132C and T159C, were reported to markedly increase their light sensitivity (Kleinlogel et al. (2011) Nat Neurosci. 14:513-8; Berndt et al. (2011) Proc Natl Acad Sci USA. 108:7595-600; Prigge et al. (2012) J Biol Chem. 287 (38) 3104:12; the contents of each of which are incorporated herein in their entireties). The properties of these two ChR2 mutants (i.e., L132C and T159C) were examined and compared with a number of double mutants at these two sites to identify suitable candidates for therapeutic methods. Compositions comprising one or more of these mutations are provided to a subject in need thereof for the purpose of restoring vision. Specifically, desired mutations in the Chop2 gene are introduced to a cell and/or integrated into the genomic DNA of a cell to improve or restore vision. Desired mutations in the Chop2 gene that are introduced to a cell to improve or restore vision may also remain episomal, not having integrated into the genomic DNA.

Mutations at the L132 or T159 amino acid positions of Chop2 (and therefore, the resulting ChR2) markedly lower the threshold light intensity that is required to elicit the ChR2-mediated photocurrent. Double mutants at the amino acid positions L132 and T159 further increase the photocurrent at low light intensities, exceeding that of either of the corresponding single mutations. Retinal ganglion cells expressing the double mutants at the L132 and T159 positions can respond to light intensities that fall within the range of normal outdoor lighting conditions but should still maintain adequate, and high temporal resolution that are suitable for restoring useful vision. Thus, mutant Chop2 protein of the present invention that form mutant ChR2s having improved light sensitivity are used alone or in combination to restore or improve vision.

Specifically, the invention provides an isolated polypeptide molecule comprising or consisting of SEQ ID NO: 26 in which the amino acid at position 132 of SEQ ID NO: 26 is not leucine (L). In certain embodiments of the isolated polypeptide molecule, the amino acid at position 132 is cysteine (C) or alanine (A). When the amino acid at position 132 is cysteine (C), the polypeptide molecule may comprise or consist of SEQ ID NO: 13. When the amino acid at position 132 is alanine (A), the polypeptide molecule may comprise or consist of SEQ ID NO: 20.

The invention provides an isolated polypeptide molecule comprising or consisting of SEQ ID NO: 26 in which the amino acid at position 159 of SEQ ID NO: 26 is not a threonine (T). In certain embodiments of the isolated polypeptide molecule, the amino acid at position 159 is cysteine (C), serine (S), or alanine (A). When the amino acid at position 159 is cysteine (C), the polypeptide molecule may comprise or consist of SEQ ID NO: 14. When the amino acid at position 159 is serine (S), the polypeptide molecule may comprise or consist of SEQ ID NO: 17. When the amino acid at position 159 is alanine (A), the polypeptide molecule may comprise or consist of SEQ ID NO: 23.

The invention provides isolated polypeptide molecule comprising or consisting of SEQ ID NO: 26 in which the amino acid at position 132 of SEQ ID NO: 26 is not leucine (L) and the amino acid at position 159 is not threonine (T). In certain embodiments of the isolated polypeptide molecule comprising or consisting of SEQ ID NO: 26 in which the amino acid at position 132 of SEQ ID NO: 26 is not leucine (L) and the amino acid at position 159 is not threonine (T), the amino acid at position 132 is cysteine (C), and the amino acid at position 159 is cysteine (C). In a preferred embodiment of this isolated polypeptide molecule, the polypeptide molecule comprises or consists of SEQ ID NO: 16. The invention provides an isolated nucleic acid molecule that encodes for the isolated polypeptide comprising or consisting of SEQ ID NO: 16. Preferably, the isolated nucleic acid molecule that encodes for the isolated polypeptide comprising or consisting of SEQ ID NO: 16, is a nucleic acid molecule that comprises or consists of SEQ ID NO: 15.

In certain embodiments of the isolated polypeptide molecule comprising or consisting of SEQ ID NO: 26 in which the amino acid at position 132 of SEQ ID NO: 26 is not leucine (L) and the amino acid at position 159 is not threonine (T), the amino acid at position 132 is cysteine (C) and the amino acid at position 159 is serine (S). The isolated polypeptide molecule comprising or consisting of SEQ ID NO: 26 in which the amino acid at position 132 of SEQ ID NO: 26 is not leucine (L) and the amino acid at position 159 is not threonine (T), may comprise or consist of SEQ ID NO: 19. Alternatively, or in addition, the isolated polypeptide molecule comprising or consisting of SEQ ID NO: 26 in which the amino acid at position 132 of SEQ ID NO: 26 is not leucine (L) and the amino acid at position 159 is not threonine (T), wherein the amino acid at position 132 is cysteine (C) and wherein the amino acid at position 159 is serine (S) may comprise or consist of SEQ ID NO: 19. The invention provides an isolated nucleic acid molecule that encodes for the isolated polypeptide that comprises or consists of SEQ ID NO: 19. Preferably, the nucleic acid molecule comprises or consists of SEQ ID NO: 18.

In certain embodiments of the isolated polypeptide molecule comprising or consisting of SEQ ID NO: 26 in which the amino acid at position 132 of SEQ ID NO: 26 is not leucine (L) and the amino acid at position 159 is not threonine (T), the amino acid at position 132 is alanine (A) and the amino acid at position 159 is cysteine (C). The isolated polypeptide molecule comprising or consisting of SEQ ID NO: 26 in which the amino acid at position 132 of SEQ ID NO: 26 is not leucine (L) and the amino acid at position 159 is not threonine (T) may comprise or consist of SEQ ID NO: 22. Alternatively, or in addition, the isolated polypeptide molecule comprising or consisting of SEQ ID NO: 26 in which the amino acid at position 132 of SEQ ID NO: 26 is not leucine (L) and the amino acid at position 159 is not threonine (T), wherein the amino acid at position 132 is alanine (A) and wherein the amino acid at position 159 is cysteine (C) may comprise or consist of SEQ ID NO: 22. The invention provides an isolated nucleic acid molecule that encodes for the isolated polypeptide that comprises or consists of SEQ ID NO: 22. Preferably, this nucleic acid molecule comprises or consists of SEQ ID NO: 21.

In certain embodiments of the isolated polypeptide molecule comprising or consisting of SEQ ID NO: 26 in which the amino acid at position 132 of SEQ ID NO: 26 is not leucine (L) and the amino acid at position 159 is not threonine (T), the amino acid at position 132 is cysteine (C) and the amino acid at position 159 is alanine (A). The isolated polypeptide molecule comprising or consisting of SEQ ID NO: 26 in which the amino acid at position 132 of SEQ ID NO: 26 is not leucine (L) and the amino acid at position 159 is not threonine (T) may comprise or consist of SEQ ID NO: 25. Alternatively, or in addition, the isolated polypeptide molecule comprising or consisting of SEQ ID NO: 26 in which the amino acid at position 132 of SEQ ID NO: 26 is not leucine (L) and the amino acid at position 159 is not threonine (T), wherein the amino acid at position 132 is cysteine (C) and wherein the amino acid at position 159 is alanine (A) may comprise or consist of SEQ ID NO: 25. The invention provides an isolated nucleic acid molecule that encodes for the isolated polypeptide that comprises or consists of SEQ ID NO: 25. Preferably, this nucleic acid molecule comprises or consists of SEQ ID NO: 24.

The invention provides any one of the isolated polypeptide molecules described herein, wherein the polypeptide molecule encodes for a mutant Chop2 protein that forms a mutant ChR2, which elicits a current in response to a threshold intensity of light that is lower than the threshold of a wild type ChR2 protein. Moreover, the current conducts cations. Exemplary cations include, but are not limited to, $H^+$, $Na^+$, $K^+$, and $Ca^{2+}$ ions. The ChR2 wild type and mutant proteins described herein non-specifically conduct cations. Consequently, the current conducts one or more of the following: $H^+$, $Na^+$, $K^+$, and $Ca^{2+}$ ions.

The invention provides any one of the isolated polypeptide molecules described herein further comprising a pharmaceutically acceptable carrier. The invention also provides a composition comprising at least one isolated polynucleotide molecule described herein. The composition may further comprise a pharmaceutically-acceptable carrier.

The invention provides an isolated nucleic acid molecule that encodes for any of the isolated polypeptides described herein. Moreover, the isolated nucleic acid molecule may further include a pharmaceutically acceptable carrier. The invention also provides a composition comprising at least one isolated nucleic acid molecule described herein. The composition may further comprise a pharmaceutically-acceptable carrier.

The invention provides a cell, wherein the cell has been contacted with or comprises an isolated polypeptide molecule of the invention. Moreover, the invention provides a cell, wherein the cell has been contacted with or comprises an isolated nucleic acid molecule that encodes for an isolated polypeptide molecule of the invention. The invention provides, a composition comprising, consisting essentially of, or consisting of a cell that comprises an isolated polypeptide molecule of the invention or a nucleic acid molecule that encodes for an isolated polypeptide molecule of the invention. Cells of the invention may be contacted with the isolated polypeptide or an isolated nucleic acid encoding the polypeptide in vitro, ex vivo, in vivo, or in situ. In certain embodiments of the invention, the cell is a photoreceptor: a horizontal cell: a bipolar cell: an amacrine cell, and, especially, an AII amacrine cell; or a retinal ganglion cell, including a photosensitive retinal ganglion cell. Preferably, the cell is a retinal ganglion cell, a photosensitive retinal ganglion cell, a bipolar cell, an ON-type bipolar cell, a rod bipolar cell, or an AII amacrine cell. In certain aspects of the invention, the cell is a photoreceptor, a bipolar cell, a rod bipolar cell, an ON-type cone bipolar cell, a retinal ganglion cell, a photosensitive retinal ganglion cell, a horizontal cell, an amacrine cell, or an AII amacrine cell.

The invention provides a method of improving or restoring vision, comprising administering to a subject any one of the compositions described herein. The invention further provides a prophylactic method of preserving vision, comprising administering to a subject any one of the compositions described herein.

The methods described herein may also be applied to those subjects who are healthy, blind (in part or in total), and/or those subjects with retinal degeneration (characterized by a loss of rod and/or cone photoreceptor cells), but may be dependent upon the activity of photosensitive retinal ganglion cells for a determination of ambient light levels. For example, the methods described herein can be used to preserve, improve, or restore the activity of a photosensitive retinal ganglion cell that mediates the transduction of light information for synchronizing circadian rhythms to the 24-hour light/dark cycle, pupillary control and reflexes, and photic regulation of melatonin release.

In certain embodiments of the methods of the invention, the subject may have normal vision or impaired vision. Alternatively, or in addition, the subject may be at risk for developing an ocular disease that leads to impairment of vision. For example, the subject may have a family history of, ocular disease, including, macular degeneration and retinitis pigmentosa. The subject may be at risk for incurring an eye injury that causes damage to photosensitive cells in the retina. The subject may have a genetic marker or genetic/congenital condition that results in impaired vision, low vision, legal blindness, partial blindness, or complete blindness. Subjects may have a refractive defect that results in myopia (near-sightedness) or hyperopia (far-sightedness).

Compositions of methods of the invention may be administered to a subject either systemically or locally. A preferred route of local administration is intravitreal injection.

Other features and advantages of the invention will be apparent from and are encompassed by the following detailed description and claims.

DETAILED DESCRIPTION

Visual System

Figure 1A:
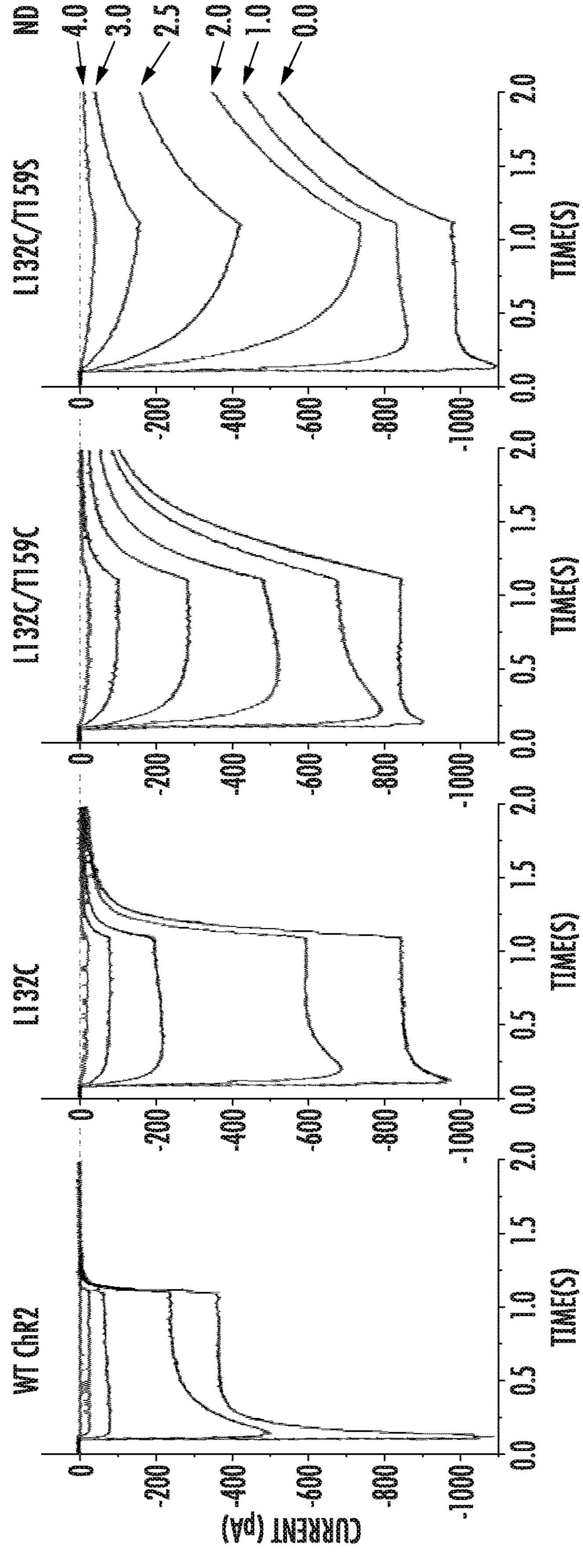
FIG. 1A-B show representative recordings of the light-evoked currents from wild-type (WT) ChR2, L132C, L132C/T159C, and L132C/159S mutants in HEK cells for comparison of their light sensitivity (A). The light stimuli (photons/cm$^2$·s at 460 nm) were generated by a xenon arc lamp and attenuated by neutral density filters: ND4.0 (2.8×10$^{14}$), ND3.0 (1.4×10$^{15}$), ND2.5 (4.8×10$^{15}$); ND2.0 (1.6×10$^{16}$), ND1.0 (1.3×10$^{17}$), ND0 (1.2×10$^{18}$). The same current traces in FIG. 1A are shown at a different current scale in FIG. 1B. The traces pointed by arrows are evoked by the same light intensity (ND2.5).

The central nervous system mediates vision (also referred to herein as sight) through specialized cells and unique methods of signal transduction present in the visual system. The principle responsibility of the visual system is to transform light, in the form of electromagnetic radiation, into a representation or image of the surrounding world. In addition to the "visual" function of this system, the visual system also regulates the pupillary light reflex (PLR), circadian photoentrainment to periodic light/dark cycles, and release of the hormone melatonin.

The cells of the retina are the first cells of the visual or nervous system to encounter light (electromagnetic radiation of varying wavelengths and intensities). Photons travel through the cornea, pupil, and lens before reaching the retina. The retina has a unique structure because the photoreceptor cells that directly absorb photons are located in the outer layer of the retina. Photons that traverse the lens first encounter an inner layer of retinal ganglion cells (a minority of which are photosensitive through the expression of the opsin, melanopsin) and an intermediate layer of bipolar cells before reaching the outer layer of photoreceptor cells (also known as rods and cones). Rod photoreceptors operate in dim illumination condition (scotopic vision) while cone photoreceptors operate in bright illumination conditions (photopic vision) responsible for color vision. Cone photoreceptors synapse directly onto ON- and OFF-type cone bipolar cells, which in turn, synapse directly onto ON- and OFF-type retinal ganglion cells. Rod photoreceptors synapse to rod bipolar cells (a unique type of bipolar cells, which is ON-type), which synapse to AII amacrine cells. The AII amacrine cells then relay the visual signals to ON-type cone bipolar cells through gap junction and to OFF-type cone bipolar cells as well as OFF ganglion cells through inhibitory glycinergic synapses. Retinal ganglion cells are responsible for relating visual information to neurons of the brain.

Phototransduction

Within the retina, photoreceptor cells absorb photon particles and transform the raw data of light frequency and wavelength into chemical and subsequently electrical signals that propagate this initial information throughout the visual and nervous systems. Specifically, an opsin protein located on the surface of a photoreceptor (rod, cone, and/or photosensitive retinal ganglion cell) absorbs a photon and initiates an intracellular signaling cascade, which results in the hyperpolarization of the photoreceptor. In the dark, the opsin proteins absorb no photons, the photoreceptors are depolarized. The visual signals of photoreceptors then relay through bipolar cells, amacrine cells, and ganglion cells to the high visual centers in the brain. Specifically, when rod and cone photoreceptors are depolarized (in the dark), they cause the depolarization of rod bipolar cells and ON-type cone bipolar cells, but the hyperpolarization of OFF-type cone bipolar cells, which in turn cause the depolarization of AII amacrine cells and the increase of the spiking of ON-type retinal ganglion cells and the decrease of the spiking of OFF-type retinal ganglion cells. The opposite happens (to rod, ON- and OFF-bipolar cells, AII amacrine and ON- and OFF-ganglion cells), when rod and cone photoreceptors are hyperpolarized (in response to light).

Light information is processed and refined significantly by the actions of photoreceptors, bipolar cells, horizontal cells, amacrine cells, and retinal ganglion cells. To add to the complexity of this system, photoreceptors are found in three main varieties, including rods, cones (of which three types respond most strongly to distinct wavelengths of light), and photosensitive retinal ganglion cells. Thus, a first layer of information processing occurs at the level of the photoreceptors which respond differentially to certain wavelengths and intensities of light. Bipolar cells of the retina receive information from both photoreceptor cells and horizontal cells. Horizontal cells of the retina receive information from multiple photoreceptor cells, and, therefore, integrate information between cell types and across distances in the retina. Bipolar cells further integrate information directly from photoreceptor cells and horizontal cells by producing mainly graded potentials to retinal ganglion cells, although some recent studies indicate that some bipolar cells can generate action potentials. Cone bipolar cells synapse on retinal ganglion cells and amacrine cells while rod bipolar cells synapse only to AII amacrine cells. Similar to horizontal cells, most amacrine cells integrate information laterally within the retina. Unlike horizontal cells, most amacrine cells are inhibitory (GABAergic) interneurons. Amacrine cells are also more specialized than horizontal cells, because each amacrine cell specifically synapses on a particular type of bipolar cell (one of the ten varieties of bipolar cell). Particularly, the AII amacrine cell is a critical relay neuron in the rod pathway (under scotopic vision when cone photoreceptors do not respond). The AII amacrine cells receive synaptic inputs from rod bipolar cells and then piggy-back the signals to cone pathway through ON- and OFF-cone bipolar cells to ON- and OFF-ganglion cells as described above. Therefore, expression of Chop2, and the resulting formation of ChR2, in rod bipolar cells or AII amacrine cells can create both ON and OFF responses in retinal ganglion cells. Furthermore, retinal ganglion cells integrate information from bipolar cells and from amacrine cells. Although retinal ganglion cells vary significantly with respect to size, connectivity, and responses to visual stimulation (e.g. visual fields), all retinal ganglion cells extend a long axon into the brain. Except for a minute portion of the retinal ganglion cells that transduce non-visual information regarding the pupillary light reflex and circadian entrainment, the totality of axons extending from the retinal ganglion cells form the optic nerve, optic chiasm, and optic tract of the central nervous system. Consequently, a significant amount of information processing occurs in the retina itself.

Photoreceptor cells express endogenous opsin proteins, such as rhodopsin. The mutant Chop2 proteins of the invention may be expressed in any cell type, and form functional ChR2 channels. Preferably, the cell is a retinal cell. Exemplary cells, include, but are not limited to, photoreceptor cells (e.g., rods, cones, and photosensitive retinal ganglion cells), horizontal cells, bipolar cells, amacrine cells, and retinal ganglion cells.

Channelopsin-2 (Chop2)

Channelopsin-2 (Chop2) was first isolated from the green algae, *Chlamydomonas reinhardtii*. Channelopsin-2 is a seven transmembrane domain protein that becomes photoswitchable (light sensitive) when bound to the chromophore all-trans-retinal. Chop2, when linked to a retinal molecule via Schiff base linkage forms a light-gated, nonspecific, inwardly rectifying, cation channel, called Channelrhodopsin-2 (Chop2 retinalidene, abbreviated ChR2).

As referred to herein, "channelopsin-2" or "Chop2" refers to the gene that encodes channelopsin-2, which then forms Channelrhodopsin-2 (ChR2) once bound to retinal. Gene constructs of the present invention refer primarily to channelopsin-2 (i.e., without the retinal), and all Chop2 variants disclosed herein form functional channelrhodopsin-2 variants. The methods disclosed herein may include delivering Chop2 to cells without exogenous retinal. It is understood that upon expression of Chop2 in cells (i.e., retinal neurons), endogenously available retinal binds to the wild-type Chop2 or the Chop2 mutants of the present invention to form functional light-gated channels, WT ChR2 or mutant ChR2. As such, Chop2 proteins, as referred to herein, can also be synonymous with ChR2.

As used herein, "channelrhodopsin-2" or "ChR2" refers to the retinal-bound functional light-sensitive channel. In one embodiment, the bound retinal may be provided exogenously. In a preferred embodiment, the bound retinal is provided from endogenous levels available in the cell. The present invention also encompasses the functional channelrhodopsin-2 channels formed by the polypeptides and polynucleotides encoding the Chop2 mutants described herein.

Upon illumination by the preferred dose of light radiation, ChR2 opens the pore of the channel, through which $H^+$, $Na^+$, $K^+$, and/or $Ca^{2+}$ ions flow into the cell from the extracellular space. Activation of the ChR2 channel typically causes a depolarization of the cell expressing the channel. Depolarized cells produce graded potentials and or action potentials to carry information from the Chop2/ChR2-expressing cell to other cells of the retina or brain.

The wild type form of ChR2 or mutant ChR2s with high temporal resolution have become a central focus of neuroscience research. When expressed in a mammalian neuron, ChR2 mediates light-controlled depolarization of in vitro or ex vivo cultures. Wild type ChR2s or mutant ChR2s with high temporal resolution (the latter usually display low light sensitivity) presents several challenges that must be addressed to enable their use for the purpose of vision restoration. For the purpose of vision restoration, the ChR2 with high light sensitivity rather than high temporal resolution is desired.

Wild type ChR2 proteins require illumination from high blue light intensities for full activation (i.e. $10^{18}$-$10^{19}$ photons $s^{-1}$ $cm^{-2}$ at a wavelength of 480 nm). Continuous illumination of this type can damage cells.

The kinetics of the wild type ChR2 protein is suboptimal for maximizing channel efficacy. Efficacy can be increased by modifying one or more amino acids of the wild type ChR2 protein either to prolong the open state of the channel or increase the unit conductance of the channel, or both. The single-channel conductance of wild-type ChR2 is small. Thus, neuronal activation in vivo would either require high expression of the wild type channel or very intense activation with the preferred wavelength of blue-light. A simpler solution may be found by altering the channel conductance or to prolong the channel open time. Either one of these mechanisms and, in particular, the combination of these mechanisms, enable lower and safer light intensities to be used to achieve the same level of cellular depolarization.

For example, mutant ChR2 proteins of the invention achieve greater light sensitivity through the prolongation of the channel open state. Consequently, each mutant ChR2 channel conducts a greater photocurrent than a wild type ChR2 channel when activated by the same light intensities. Therefore, the mutant channels are activated by light intensities that are lower than those required for activation of the wild type ChR2 channels. Quantitatively, detectable spiking activity of retinal ganglion cells expressing mutant ChR2 proteins can be elicited by a light intensity that is 1.5-2 log units lower than the light intensity required to elicit spiking activity from retinal ganglion cells expressing wild type ChR2. Thus, the light intensities required to activate the mutant ChR2 proteins are close to or fall within the range of normal outdoor lighting conditions.

The following sequences provide non-limiting examples of wild type and mutant Chop2 proteins, and polynucleotides encoding said WT and mutant Chop2 proteins of the invention, and forming WT and mutant ChR2s of the invention.

A wild type (WT) Chop2 of the invention may be encoded by the following *Chlamydomonas reinhardtii* chlamyopsin 4 light-gated ion channel (COP4) mRNA sequence (GenBank Accession No. XM_001701673, and SEQ ID NO: 1):

```
   1 gcagcaccat acttgacatc tgtcgccaag caagcattaa acatggatta tggaggcgcc
  61 ctgagtgccg ttgggcgcga gctgctattt gtaacgaacc cagtagtcgt caatggctct
 121 gtacttgtgc ctgaggacca gtgttactgc gcgggctgga ttgagtcgcg tggcacaaac
 181 ggtgcccaaa cggcgtcgaa cgtgctgcaa tggcttgctg ctggcttctc catcctactg
 241 cttatgtttt acgcctacca aacatggaag tcaacctgcg gctgggagga gatctatgtg
 301 tgcgctatcg agatggtcaa ggtgattctc gagttcttct tcgagtttaa gaacccgtcc
 361 atgctgtatc tagccacagg ccaccgcgtc cagtggttgc gttacgccga gtggcttctc
 421 acctgcccgg tcattctcat tcacctgtca aacctgacgg gcttgtccaa cgactacagc
 481 aggcgcacca tgggtctgct tgtgtctgat attggcacaa ttgtgtgggg cgccacttcc
 541 gccatggcca ccggatacgt caaggtcatc ttcttctgcc tgggtctgtg ttatggtgct
 601 aacacgttct ttcacgctgc caaggcctac atcgagggtt accacaccgt gccgaagggc
 661 cggtgtcgcc aggtggtgac tggcatggct tggctcttct tcgtatcatg ggtatgttc
 721 cccatcctgt tcatcctcgg ccccgagggc ttcggcgtcc tgagcgtgta cggctccacc
 781 gtcggccaca ccatcattga cctgatgtcg aagaactgct ggggtctgct cggccactac
 841 ctgcgcgtgc tgatccacga gcatatcctc atccacggcg acattcgcaa gaccaccaaa
 901 ttgaacattg gtggcactga gattgaggtc gagacgctgg tggaggacga ggccgaggct
 961 ggcgcggtca acaagggcac cggcaagtac gcctcccgcg agtccttcct ggtcatgcgc
1021 gacaagatga aggagaaggg cattgacgtg cgcgcctctc tggacaacag caaggaggtg
1081 gagcaggagc aggccgccag ggctgccatg atgatgatga acggcaatgg catgggtatg
1141 ggaatgggaa tgaacggcat gaacggaatg ggcggtatga acgggatggc tggcggcgcc
1201 aagcccggcc tggagctcac tccgcagcta cagcccggcc gcgtcatcct ggcggtgccg
1261 gacatcagca tggttgactt cttccgcgag cagtttgctc agctatcggt gacgtacgag
1321 ctggtgccgg ccctgggcgc tgacaacaca ctggcgctgg ttacgcaggc gcagaacctg
1381 ggcggcgtgg actttgtgtt gattcacccc gagttcctgc gcgaccgctc tagcaccagc
1441 atcctgagcc gcctgcgcgg cgcgggccag cgtgtggctg cgttcggctg ggcgcagctg
1501 gggcccatgc gtgacctgat cgagtccgca aacctggacg gctggctgga gggcccctcg
1561 ttcggacagg gcatcctgcc ggcccacatc gttgccctgg tggccaagat gcagcagatg
1621 cgcaagatgc agcagatgca gcagattggc atgatgaccg gcggcatgaa cggcatgggc
1681 ggcggtatgg gcggcggcat gaacggcatg ggcggcggca acggcatgaa caacatgggc
1741 aacggcatgg gcggcggcat gggcaacggc atgggcggca atggcatgaa cggaatgggt
1801 ggcggcaacg gcatgaacaa catgggcggc aacggaatgg ccggcaacgg aatgggcggc
1861 ggcatgggcg gcaacggtat gggtggctcc atgaacggca tgagctccgg cgtggtggcc
1921 aacgtgacgc cctccgccgc cggcggcatg ggcggcatga tgaacggcgg catggctgcg
1981 ccccagtcgc ccggcatgaa cggcggccgc ctgggtacca acccgctctt caacgccgcg
2041 ccctcaccgc tcagctcgca gctcggtgcc gaggcaggca tgggcagcat gggaggcatg
```

-continued

```
2101 ggcggaatga gcggaatggg aggcatgggt ggaatggggg gcatgggcgg cgccggcgcc
2161 gccacgacgc aggctgcggg cggcaacgcg gaggcggaga tgctgcagaa tctcatgaac
2221 gagatcaatc gcctgaagcg cgagcttggc gagtaaaagg ctggaggccg gtactgcgat
2281 acctgcgagc tcgcgcgcct gactcgtcgt acacacggct caggagcacg cgcgcgtgga
2341 cttctcaacc tgtgtgcaac gtatctagag cggcctgtgc gcgaccgtcc gtgagcattc
2401 cggtgcgatc ttcccgcctt cgcaccgcaa gttcccttcc tggccctgct gcgcctgacg
2461 catcgtccga acggaagggc ggcttgatca gtaaagcatt gaagactgaa gtcgtgcgac
2521 cgtagtgcta tggctctgca cgtaagtggg cgctgccctg cttactacgc attgcccaag
2581 actgcttcct tttggtggcc gaggccctgg tcccacatca ttcatttgca taacgtactg
2641 tttagttaca tacgctttgc ttaacctcga caattgcaac atgggctgag agtccgtacg
2701 gcggctatgg acgaaggtgt tatcggatgt gattaggaat ctcggttgaa aggcttcgag
2761 aaagtgagct tcatctgtgg cttctgttgg ggtcatcaag aagaacgacg gtaaggcaaa
2821 cgaggtaaaa gtggcacgtc tttgtgcaca acgggcccgt ggagagtggg ggagtgcatg
2881 tgtgcggtcc taacacgcga gtgcaaagcg ggcttttctg gagctgggtt acggtctggc
2941 tcggcaactg ctctgtgttt taaccacagc ttcggaagtc tgggtatgtt ttgttggcag
3001 aaacatttgg gtaacttgag ggtgattcgt ctggagtcgg acaacatggc tgccgtccgt
3061 gtgcagggac ggtaatcaat gagctggagc tgtgatgctc accacacgtt gcatacccct
3121 gcttacaaaa acactttgat gtcgtggcca aactatgcgt gagcaaagag ttaaagaggc
3181 atgagtgcat ggttgcggac gtgcgcaaca attgcatcaa gtatttgacg ccttcaagcc
3241 aacaagtgcg cgcgcggcaa cttgattaac acgccggacg cagtggtggg ggcgtgtaca
3301 gtgtttatga gctgccattc tgcgatccgt agtgttaggt tgcgtgtgac gccgcgcggc
3361 tgtgggccct tacatggaga gttgggtgct tcaccacacg gttggcgccg ctgaagggtg
3421 tgctatgttt tggtaaagcc ggggccctga agaccgcaac cgtagaaccg tactgaaagg
3481 gtgtcagccc ggggtaactg gatgccctgg gacatagcta ttaatgttga agtgaagccg
3541 tcaagccgag tgccgtgcgc cgctgtatca ccaaggcccg tccta
```

A wild type (WT) ChR2 of the invention may be encoded by the following *Chlamydomonas reinhardtii* chlamyopsin 4 light-gated ion channel (COP4) amino acid sequence (GenBank Accession No. XP_001701725, and SEQ ID NO: 2):

```
  1 mdyggalsav grellfvtnp vvvngsvlvp edqcycagwi esrgtngaqt asnvlqwlaa
 61 gfsilllmfy ayqtwkstcg weeiyvcaie mvkvilefff efknpsmlyl atghrvqwlr
121 yaewlltcpv ilihlsnltg lsndysrrtm gllvsdigti vwgatsamat gyvkviffcl
181 glcygantff haakayiegy htvpkgrcrq vvtgmawlff vswgmfpilf ilgpegfgvl
241 svygstvght iidlmskncw gllghylrvl ihehilihgd irkttklnig gteievetlv
301 edeaeagavn kgtgkyasre sflvmrdkmk ekgidvrasl dnskeveqeq aaraammmmn
361 gngmgmgmgm ngmngmggmn gmaggakpgl eltpqlqpgr vilavpdism vdffreqfaq
421 lsvtyelvpa lgadntlalv tqaqnlggvd fvlihpeflr drsstsilsr lrgagqrvaa
481 fgwaqlgpmr dliesanldg wlegpsfgqg ilpahivalv akmqqmrkmq qmqqigmmtg
541 gmngmgggmg ggmngmgggn gmnnmgngmg ggmgngmggn gmngmgggng mnnmggngma
```

-continued

```
601 gngmgggmgg ngmggsmngm ssgvvanvtp saaggmggmm nggmaapqsp gmnggrlgtn

661 plfnaapspl ssqlgaeagm gsmggmggms gmggmggmgg mggagaattq aaggnaeaem

721 lqnlmneinr lkrelge
```

A wild type (WT) Chop2 of the invention may be encoded by the following *Chlamydomonas reinhardtii* retinal binding protein (cop4) gene sequence (GenBank Accession No. AF461397, and SEQ ID NO: 3):

```
   1 gcatctgtcg ccaagcaagc attaaacatg gattatggag gcgccctgag tgccgttggg
  61 cgcgagctgc tatttgtaac gaacccagta gtcgtcaatg gctctgtact tgtgcctgag
 121 gaccagtgtt actgcgcggg ctggattgag tcgcgtggca caaacggtgc ccaaacggcg
 181 tcgaacgtgc tgcaatggct tgctgctggc ttctccatcc tactgcttat gttttacgcc
 241 taccaaacat ggaagtcaac ctgcggctgg gaggagatct atgtgtgcgc tatcgagatg
 301 gtcaaggtga ttctcgagtt cttcttcgag tttaagaacc cgtccatgct gtatctagcc
 361 acaggccacc gcgtccagtg gttgcgttac gccgagtggc ttctcacctg cccggtcatt
 421 ctcattcacc tgtcaaacct gacgggcttg tccaacgact acagcaggcg caccatgggt
 481 ctgcttgtgt ctgatattgg cacaattgtg tggggcgcca cttccgccat ggccaccgga
 541 tacgtcaagg tcatcttctt ctgcctgggt ctgtgttatg gtgctaacac gttctttcac
 601 gctgccaagg cctacatcga gggttaccac accgtgccga agggccggtg tcgccaggtg
 661 gtgactggca tggcttggct cttcttcgta tcatggggta tgttccccat cctgttcatc
 721 ctcggccccg agggcttcgg cgtcctgagc gtgtacggct ccaccgtcgg ccacaccatc
 781 attgacctga tgtcgaagaa ctgctggggt ctgctcggcc actacctgcg cgtgctgatc
 841 cacgagcata tcctcatcca cggcgacatt cgcaagacca ccaaattgaa cattggtggc
 901 actgagattg aggtcgagac gctggtggag gacgaggccg aggctggcgc ggtcaacaag
 961 ggcaccggca agtacgcctc ccgcgagtcc ttcctggtca tgcgcgacaa gatgaaggag
1021 aagggcattg acgtgcgcgc ctctctggac aacagcaagg aggtggagca ggagcaggcc
1081 gccagggctg ccatgatgat gatgaacggc aatggcatgg gtatgggaat gggaatgaac
1141 ggcatgaacg gaatgggcgg tatgaacggg atggctggcg gcgccaagcc cggcctggag
1201 ctcactccgc agctacagcc cggccgcgtc atcctggcgg tgccggacat cagcatggtt
1261 gacttcttcc gcgagcagtt tgctcagcta tcggtgacgt acgagctggt gccggccctg
1321 ggcgctgaca acacactggc gctggttacg caggcgcaga acctgggcgg cgtggacttt
1381 gtgttgattc accccgagtt cctgcgcgac cgctctagca ccagcatcct gagccgcctg
1441 cgcggcgcgg gccagcgtgt ggctgcgttc ggctgggcgc agctggggcc catgcgtgac
1501 ctgatcgagt ccgcaaacct ggacggctgg ctggagggcc cctcgttcgg acagggcatc
1561 ctgccggccc acatcgttgc cctggtggcc aagatgcagc agatgcgcaa gatgcagcag
1621 atgcagcaga ttggcatgat gaccggcggc atgaacggca tgggcggcgg tatgggcggc
1681 ggcatgaacg gcatgggcgg cggcaacggc atgaacaaca tgggcaacgg catgggcggc
1741 ggcatgggca acggcatggg cggcaatggc atgaacggaa tgggtggcgg caacggcatg
1801 aacaacatgg gcggcaacgg aatggccggc aacggaatgg gcggcggcat gggcggcaac
1861 ggtatgggtg gctccatgaa cggcatgagc tccggcgtgg tggccaacgt gacgccctcc
1921 gccgccggcg gcatgggcgg catgatgaac ggcggcatgg ctgcgcccca gtcgcccggc
1981 atgaacggcg gccgcctggg taccaacccg ctcttcaacg ccgcgccctc accgctcagc
```

-continued 2041 tcgcagctcg gtgccgaggc aggcatgggc agcatgggag gcatgggcgg aatgagcgga 2101 atgggaggca tgggtggaat ggggggcatg ggcggcgccg gcgccgccac gacgcaggct 2161 gcgggcggca acgcggaggc ggagatgctg cagaatctca tgaacgagat caatcgcctg 2221 aagcgcgagc ttggcgagta a A wild type (WT) Chop2 of the invention may be encoded by the following *Chlamydomonas reinhardtii* retinal binding protein (cop4) amino acid sequence (GenBank Accession No. AAM15777, and SEQ ID NO: 4):

1 mdyggalsav grellfvtnp vvvngsvlvp edqcycagwi esrgtngaqt asnvlqwlaa 61 gfsilllmfy ayqtwkstcg weeiyvcaie mvkvilefff efknpsmlyl atghrvqwlr 121 yaewlltcpv ilihlsnltg lsndysrrtm gllvsdigti vwgatsamat gyvkviffcl 181 glcygantff haakayiegy htvpkgrcrq vvtgmawlff vswgmfpilf ilgpegfgvl 241 svygstvght iidlmskncw gllghylrvl ihehilihgd irkttklnig gteievetiv 301 edeaeagavn kgtgkyasre sflvmrdkmk ekgidvrasl dnskeveqeq aaraammmmn 361 gngmgmgmgm ngmngmggmn gmaggakpgl eltpqlqpgr vilavpdism vdffreqfaq 421 lsvtyelvpa lgadntlalv tqaqnlggvd fvlihpeflr drsstsilsr lrgagqrvaa 481 fgwaqlgpmr dliesanldg wlegpsfgqg ilpahivalv akmqqmrkmq qmqqigmmtg 541 gmngmgggmg ggmngmgggn gmnnmgngmg ggmgngmggn gmngmgggng mnnmggngma 601 gngmgggmgg ngmggsmngm ssgvvanvtp saaggmggmm nggmaapqsp gmnggrlgtn 661 plfnaapspl ssqlgaeagm gsmggmggms gmggmggmgg mggagaattq aaggnaeaem 721 lqnlmneinr lkrelge A wild type (WT) Chop2 of the invention may be encoded by the following *Chlamydomonas reinhardtii* sensory opsin B (CSOB) mRNA sequence (GenBank Accession No. AF508966, and SEQ ID NO: 5):

1 ttgacatctg tcgccaagca agcattaaac atggattatg gaggcgccct gagtgccgtt 61 gggcgcgagc tgctatttgt aacgaaccca gtagtcgtca atggctctgt acttgtgcct 121 gaggaccagt gttactgcgc gggctggatt gagtcgcgtg gcacaaacgg tgcccaaacg 181 gcgtcgaacg tgctgcaatg gcttgctgct ggcttctcca tcctactgct tatgttttac 241 gcctaccaaa catggaagtc aacctgcggc tgggaggaga tctatgtgtg cgctatcgag 301 atggtcaagg tgattctcga gttcttcttc gagtttaaga acccgtccat gctgtatcta 361 gccacaggcc accgcgtcca gtggttgcgt tacgccgagt ggcttctcac ctgcccggtc 421 attctcattc acctgtcaaa cctgacgggc ttgtccaacg actacagcag gcgcaccatg 481 ggtctgcttg tgtctgatat tggcacaatt gtgtggggcg ccacttccgc catggccacc 541 ggatacgtca aggtcatctt cttctgcctg ggtctgtgtt atggtgctaa cacgttcttt 601 cacgctgcca aggcctacat cgagggttac cacaccgtgc cgaagggccg gtgtcgccag 661 gtggtgactg gcatggcttg gctcttcttc gtatcatggg gtatgttccc catcctgttc 721 atcctcggcc ccgagggctt cggcgtcctg agcgtgtacg gctccaccgt cggccacacc 781 atcattgacc tgatgtcgaa gaactgctgg ggtctgctcg gccactacct gcgcgtgctg 841 atccacgagc atatcctcat ccacggcgac attcgcaaga ccaccaaatt gaacattggt 901 ggcactgaga ttgaggtcga gacgctggtg gaggacgagg ccgaggctgg cgcggtcaac 961 aagggcaccg gcaagtacgc ctcccgcgag tccttcctgg tcatgcgcga caagatgaag -continued 1021 gagaagggca ttgacgtgcg cgcctctctg gacaacagca aggaggtgga gcaggagcag
1081 gccgccaggg ctgccatgat gatgatgaac ggcaatggca tgggtatggg aatgggaatg
1141 aacggcatga acggaatggg cggtatgaac gggatggctg gcggcgccaa gcccggcctg
1201 gagctcactc cgcagctaca gcccggccgc gtcatcctgg cggtgccgga catcagcatg
1261 gttgacttct tccgcgagca gtttgctcag ctatcggtga cgtacgagct ggtgccggcc
1321 ctgggcgctg acaacacact ggcgctggtt acgcaggcgc agaacctggg cggcgtggac
1381 tttgtgttga ttcaccccga gttcctgcgc gaccgctcta gcaccagcat cctgagccgc
1441 ctgcgcggcg cgggccagcg tgtggctgcg ttcggctggg cgcagctggg gcccatgcgt
1501 gacctgatcg agtccgcaaa cctggacggc tggctggagg gcccctcgtt cggacagggc
1561 atcctgccgg cccacatcgt tgccctggtg gccaagatgc agcagatgcg caagatgcag
1621 cagatgcagc agattggcat gatgaccggc ggcatgaacg gcatgggcgg cggtatgggc
1681 ggcggcatga acggcatggg cggcggcaac ggcatgaaca acatgggcaa cggcatgggc
1741 ggcggcatgg gcaacggcat gggcggcaat ggcatgaacg gaatgggtgg cggcaacggc
1801 atgaacaaca tgggcggcaa cggaatggcc ggcaacggaa tgggcggcgg catgggcggc
1861 aacggtatgg gtggctccat gaacggcatg agctccggcg tggtggccaa cgtgacgccc
1921 tccgccgccg gcggcatggg cggcatgatg aacggcggca tggctgcgcc ccagtcgccc
1981 ggcatgaacg gcggccgcct gggtaccaac ccgctcttca acgccgcgcc ctcaccgctc
2041 agctcgcagc tcggtgccga ggcaggcatg ggcagcatgg gaggcatggg cggaatgagc
2101 ggaatgggag gcatgggtgg aatggggggc atgggcggcg ccggcgccgc cacgacgcag
2161 gctgcgggcg gcaacgcgga ggcggagatg ctgcagaatc tcatgaacga gatcaatcgc
2221 ctgaagcgcg agcttggcga gtaaaaggct ggaggccggt actgcgatac ctgcgagctc
2281 gcgcgcctga ctcgtcgtac acacggctca ggagcacgcg cgcgtggact tctcaacctg
2341 tgtgcaacgt atctagagcg gcctgtgcgc gaccgtccgt gagcattccg gtgcgatctt
2401 cccgccttcg caccgcaagt tcccttcctg gccctgctgc gcctgacgca tcgtccgaac
2461 ggaagggcgg cttgatcagt aaagcattga agactgaagt cgtgcgaccg tagtgctatg
2521 gctctgcacg taagtgggcg ctgccctgct tactacgcat tgcccaagac tgcttccttt
2581 tggtggccga ggccctggtc ccacatcatt catttgcata acgtactgtt tagttacata
2641 cgctttgctt aacctcgaca attgcaacat gggctgagag tccgtacggc ggctatggac
2701 gaaggtgtta tcggatgtga ttaggaatct cggttgaaag gcttcgagaa agtgagcttc
2761 ttctgtggct tctgttgggg tcatcaagaa gaacgacggt aaggcaaacg aggtaaaagt
2821 ggcacgtctt tgtgcacaac gggcccgtgg agagtggggg agtgcatgtg tgcggtccta
2881 acacgcgagt gcaaagcggg cttttctgga gctgggttac ggtctggctc ggcaactgct
2941 ctgtgtttta accacagctt cggaagtctg ggtatgtttt gttggcagaa acatttgggt
3001 aacttgaggg tgattcgtct ggagtcggac aacatggctg ccgtccgtgt gcagggacgg
3061 taatcaatga agctgaagct gtgatgctca ccacacgttg catacccctg cttacaaaaa
3121 cactttgatg tcgtggccaa actatgcgtg agcaaagagt taaagaggca tgagtgcatg
3181 gttgcggacg tgcgcaacaa ttgcatcaag tatttgacgc cttcaagcca acaagtgcgc
3241 gcgcggcaac ttgattaaca cgccggacgc agtggtgggg gcgtgtacag tgtttatgag
3301 ctgccattct gcgatccgta gtgttaggtt gcgtgtgacg ccgcgcggct gtgggccctt
3361 acatggagag ttgggtgctt caccacacgg ttggcgccgc tgaagggtgt gctatgtttt
3421 ggtaaagccg gggccctgaa gaccgcaacc gtagaaccgt actgaaaggg tgtcagcccg -continued 3481 gggtaactgg atgccctggg acatagctat taatgttgaa gtgaagccgt caagccgagt 3541 gccgtgcgcc gctgtatcac caaggcccgt ccaaaaaaaa aaaaaaaaaa aaaaaaaaa A wild type (WT) Chop2 of the invention may be encoded by the following *Chlamydomonas reinhardtii* sensory opsin B (CSOB) amino acid sequence (GenBank Accession No. AAM44040, and SEQ ID NO: 6):

1 mdyggalsav grellfvtnp vvvngsvlvp edqcycagwi esrgtngaqt asnvlqwlaa 61 gfsilllmfy ayqtwkstcg weeiyvcaie mvkvilefff efknpsmlyl atghrvqwlr 121 yaewlltcpv ilihlsnltg lsndysrrtm gllvsdigti vwgatsamat gyvkviffcl 181 glcygantff haakayiegy htvpkgrcrq vvtgmawlff vswgmfpilf ilgpegfgvl 241 svygstvght iidlmskncw gllghylrvl ihehilihgd irkttklnig gteievetlv 301 edeaeagavn kgtgkyasre sflvmrdkmk ekgidvrasl dnskeveqeq aaraammmmn 361 gngmgmgmgm ngmngmggmn gmaggakpgl eltpqlqpgr vilavpdism vdffreqfaq 421 lsvtyelvpa lgadntlalv tqaqnlggvd fvlihpeflr drsstsilsr lrgagqrvaa 481 fgwaqlgpmr dliesanldg wlegpsfgqg ilpahivalv akmqqmrkmq qmqqigmmtg 541 gmngmgggmg ggmngmgggn gmnnmgngmg ggmgngmggn gmngmgggng mnnmggngma 601 gngmgggmgg ngmggsmngm ssgvvanvtp saaggmggmm nggmaapqsp gmnggrlgtn 661 plfnaapspl ssqlgaeagm gsmggmggms gmggmggmgg mggagaattq aaggnaeaem 721 lqnlmneinr lkrelge A wild type (WT) Chop2 of the invention may be encoded by the following *Chlamydomonas reinhardtii* acop2 mRNA for archaeal-type opsin 2 nucleic acid sequence (GenBank Accession No. AB058891, and SEQ ID NO: 7):

1 catctgtcgc caagcaagca ttaaacatgg attatggagg cgccctgagt gccgttgggc 61 gcgagctgct atttgtaacg aacccagtag tcgtcaatgg ctctgtactt gtgcctgagg 121 accagtgtta ctgcgcgggc tggattgagt cgcgtggcac aaacggtgcc caaacggcgt 181 cgaacgtgct gcaatggctt gctgctggct tctccatcct actgcttatg ttttacgcct 241 accaaacatg gaagtcaacc tgcggctggg aggagatcta tgtgtgcgct atcgagatgg 301 tcaaggtgat tctcgagttc ttcttcgagt ttaagaaccc gtccatgctg tatctagcca 361 caggccaccg cgtccagtgg ttgcgttacg ccgagtggct tctcacctgc ccggtcattc 421 tcattcacct gtcaaacctg acgggcttgt ccaacgacta cagcaggcgc accatgggtc 481 tgcttgtgtc tgatattggc acaattgtgt ggggcgccac ttccgccatg gccaccggat 541 acgtcaaggt catcttcttc tgcctgggtc tgtgttatgg tgctaacacg ttctttcacg 601 ctgccaaggc ctacatcgag ggttaccaca ccgtgccgaa gggccggtgt cgccaggtgg 661 tgactggcat ggcttggctc ttcttcgtat catggggtat gttccccatc ctgttcatcc 721 tcggccccga gggcttcggc gtcctgagcg tgtacggctc caccgtcggc cacaccatca 781 ttgacctgat gtcgaagaac tgctggggtc tgctcggcca ctacctgcgc gtgctgatcc 841 acgagcatat cctcatccac ggcgacattc gcaagaccac caaattgaac attggtggca 901 ctgagattga ggtcgagacg ctggtggagg acgaggccga ggctggcgcg gtcaacaagg 961 gcaccggcaa gtacgcctcc cgcgagtcct tcctggtcat gcgcgacaag atgaaggaga 1021 agggcattga cgtgcgcgcc tctctggaca acagcaagga ggtggagcag gagcaggccg 1081 ccagggctgc catgatgatg atgaacggca atggcatggg tatgggaatg ggaatgaacg -continued

```
1141 gcatgaacgg aatgggcggt atgaacggga tggctggcgg cgccaagccc ggcctggagc
1201 tcactccgca gctacagccc ggccgcgtca tcctggcggt gccggacatc agcatggttg
1261 acttcttccg cgagcagttt gctcagctat cggtgacgta cgagctggtg ccggccctgg
1321 gcgctgacaa cacactggcg ctggttacgc aggcgcagaa cctgggcggc gtggactttg
1381 tgttgattca ccccgagttc ctgcgcgacc gctctagcac cagcatcctg agccgcctgc
1441 gcggcgcggg ccagcgtgtg gctgcgttcg gctgggcgca gctggggccc atgcgtgacc
1501 tgatcgagtc cgcaaacctg gacggctggc tggagggccc ctcgttcgga cagggcatcc
1561 tgccggccca catcgttgcc ctggtggcca agatgcagca gatgcgcaag atgcagcaga
1621 tgcagcagat tggcatgatg accggcggca tgaacggcat gggcggcggt atgggcggcg
1681 gcatgaacgg catgggcggc ggcaacggca tgaacaacat gggcaacggc atgggcggcg
1741 gcatgggcaa cggcatgggc ggcaatggca tgaacggaat gggtggcggc aacggcatga
1801 acaacatggg cggcaacgga atggccggca acggaatggg cggcggcatg ggcggcaacg
1861 gtatgggtgg ctccatgaac ggcatgagct ccggcgtggt ggccaacgtg acgccctccg
1921 ccgccggcgg catgggcggc atgatgaacg gcggcatggc tgcgccccag tcgcccggca
1981 tgaacggcgg ccgcctgggt accaacccgc tcttcaacgc cgcgccctca ccgctcagct
2041 cgcagctcgg tgccgaggca ggcatgggca gcatgggagg catgggcgga atgagcggaa
2101 tgggaggcat gggtggaatg gggggcatgg gcggcgccgg cgccgccacg acgcaggctg
2161 cgggcggcaa cgcggaggcg gagatgctgc agaatctcat gaacgagatc aatcgcctga
2221 agcgcgagct tggcgagtaa aaggctggag gccggtactg cgatacctgc gagctcgcgc
2281 gcctgactcg tcgtacacac ggctcaggag cacgcgcgcg tggacttctc aacctgtgtg
2341 caacgtatct agagcggcct gtgcgcgacc gtccgtgagc attccggtgc gatcttcccg
2401 ccttcgcacc gcaagttccc ttcctggccc tgctgcgcct gacgcatc
```

A wild type (WT) Chop2 of the invention may be encoded by the following *Chlamydomonas reinhardtii* acop2 mRNA for archaeal-type opsin 2 amino acid sequence (GenBank Accession No. BAB68567, and SEQ ID NO: 8):

```
  1 mdyggalsav grellfvtnp vvvngsvlvp edqcycagwi esrgtngaqt asnvlqwlaa
 61 gfsilllmfy ayqtwkstcg weeiyvcaie mvkvilefff efknpsmlyl atghrvqwlr
121 yaewlltcpv ilihlsnltg lsndysrrtm gllvsdigti vwgatsamat gyvkviffcl
181 glcygantff haakayiegy htvpkgrcrq vvtgmawlff vswgmfpilf ilgpegfgvl
241 svygstvght iidlmskncw gllghylrvl ihehilihgd irkttklnig gteievetlv
301 edeaeagavn kgtgkyasre sflvmrdkmk ekgidvrasl dnskeveqeq aaraammmmn
361 gngmgmgmgm ngmngmggmn gmaggakpgl eltpqlqpgr vilavpdism vdffreqfaq
421 lsvtyelvpa lgadntlalv tqaqnlggvd fvlihpeflr drsstsilsr lrgagqrvaa
481 fgwaqlgpmr dliesanldg wlegpsfgqg ilpahivalv akmqqmrkmq qmqqigmmtg
541 gmngmgggmg ggmngmgggn gmnnmgngmg ggmgngmggn gmngmgggng mnnmggngma
601 gngmgggmgg ngmggsmngm ssgvvanvtp saaggmggmm nggmaapqsp gmnggrlgtn
661 plfnaapspl ssqlgaeagm gsmggmggms gmggmggmgg mggagaattq aaggnaeaem
721 lqnlmneinr lkrelge
```

ChR2 Mutants

The present invention provides Chop2 mutants wherein one or more amino acids are mutated. In some embodiments, the Chop2 is the full-length polypeptide, such as SEQ ID NOs: 2, 4, 6, and 8, with at least one amino acid mutation. In some embodiments, the mutation is at amino acid 132 and/or amino acid 159. In some preferred embodiments, the amino acid at position 132 is mutated from a leucine to a cysteine or an alanine. In some preferred embodiments, the amino acid at position 159 is mutated from a threonine to an alanine, a cysteine, or a serine. In all embodiments, the Chop2 mutants form a functional ChR2 channel.

The present invention also encompasses Chop2 proteins and nucleic acids that encode a biologically active fragment or a conservative amino acid substitution or other mutation variant of Chop2. Non-limiting examples of useful fragments include polypeptides encoding amino acids 1-315 of the wild-type Chop2, i.e., SEQ ID NO: 26, wherein at least one amino acid is mutated or conservatively substituted, for example at amino acid positions 132 and/or 159. Smaller fragments of wild-type Chop2, wherein at least one amino acid is mutated or conservatively substituted (i.e., at amino acid positions 132 and/or 159) may also be useful in the present invention. Accordingly, Chop2 polypeptides and nucleic acids of the present invention further include, but are not limited to, biologically active fragments encoding amino acids 1-315, 1-310, 1-300, 1-275, 1-250, 1-225, 1-200, 1-175, or 1-160 of the wild-type Chop2, wherein at least one amino acid is mutated or conservatively substituted, for example at amino acid positions 132 and/or 159. In other embodiments, the Chop2 polypeptides and nucleic acids of the present invention can be up to, or about, 315 amino acids long, 310 amino acids long, 300 amino acids long, 275 amino acids long, 250 amino acids long, 225 amino acids long, 200 amino acids long, 175 amino acids long, or 160 amino acids long.

A single mutant Chop2 of the invention may be encoded by the following Synthetic construct hVChR1-mKate-betahChR2 (L132C) gene sequence (GenBank Accession No. JN836746, and SEQ ID NO: 9) with the following annotations, GFP sequence is in bold, L132C Chop2 sequence is underlined:

1 atggattacc ctgtggcccg gtccctgatt gtaagatacc ccaccgatct gggcaatgga 61 accgtgtgca tgcccagagg acaatgctac tgcgaggggt ggctgaggag ccggggcact 121 agtatcgaaa aaaccatcgc tatcaccctc cagtgggtag tgttcgctct gtccgtagcc 181 tgtctcggct ggtatgcata ccaagcctgg agggctacct gtgggtggga ggaagtatac 241 gtggccctga tcgagatgat gaagtccatc atcgaggctt tccatgagtt cgactcccca 301 gccacactct ggctcagcag tgggaatggc gtagtgtgga tgagatatgg agagtggctg 361 ctgacctgtc ccgtcctgct cattcatctg tccaatctga ccgggctgaa agatgactac 421 tccaagagaa caatgggact gctggtgagt gacgtggggt gtattgtgtg gggagccacc 481 tccgccatgt gcactggatg gaccaagatc ctctttttcc tgatttccct ctcctatggg 541 atgtatacat acttccacgc cgctaaggtg tatattgagg ccttccacac tgtacctaaa 601 ggcatctgta gggagctcgt gcgggtgatg gcatggacct tctttgtggc ctgggggatg 661 ttccccgtgc tgttcctcct cggcactgag ggatttggcc acattagtcc ttacgggtcc 721 gcaattggac actccatcct ggatctgatt gccaagaata tgtgggggt gctgggaaat 781 tatctgcggg taaagatcca cgagcatatc ctgctgtatg gcgatatcag aaagaagcag 841 aaaatcacca ttgctggaca ggaaatggag gtggagacac tggtagcaga ggaggaggac 901 gggaccgcgg tcgccaccat ggtgtctaag ggcgaagagc tgattaagga gaacatgcac

961 atgaagctgt acatggaggg caccgtgaac aaccaccact tcaagtgcac atccgagggc

1021 gaaggcaagc cctacgaggg cacccagacc atgagaatca aggtggtcga gggcggccct

1081 ctccccttcg ccttcgacat cctggctacc agcttcatgt acggcagcaa aaccttcatc

1141 aaccacaccc agggcatccc cgacttcttt aagcagtcct tccctgaggg cttcacatgg

1201 gagagagtca ccacatacga agacgggggc gtgctgaccg ctacccagga caccagcctc

1261 caggacggct gcctcatcta caacgtcaag atcagagggg tgaacttccc atccaacggc

1321 cctgtgatgc agaagaaaac actcggctgg gaggcctcca ccgagatgct gtaccccgct

1381 gacggcggcc tggaaggcag agccgacatg gccctgaagc tcgtgggcgg gggccacctg

1441 atctgcaact tgaagaccac atacagatcc aagaaacccg ctaagaacct caagatgccc

1501 ggcgtctact atgtggacag aagactggaa agaatcaagg aggccgacaa agagacctac

1561 gtcgagcagc acgaggtggc tgtggccaga tactgcgacc tccctagcaa actggggcac 1621 aaacttaatt gcctgcagga gaagaagtca tgcagccagc gcatggccga attccggcaa -continued 1681 tactgttgga acccggacac tgggcagatg ctgggccgca ccccagcccg gtgggtgtgg 1741 atcagcctgt actatgcagc tttctacgtg gtcatgactg ggctctttgc cttgtgcatc 1801 tatgtgctga tgcagaccat tgatccctac acccccgact accaggacca gttaaagtca 1861 ccgggggtaa ccttgagacc ggatgtgtat ggggaaagag ggctgcagat ttcctacaac 1921 atctctgaaa acagctctag acaggcccag atcaccggac gtccggagac tgagacattg 1981 ccaccggtgg actacggggg ggccctgagc gctgtgggca gagaactcct gttcgtgaca 2041 aatccagtcg tggtgaacgg ctccgtactc gtacccgagg atcagtgcta ttgcgcagga 2101 tggatcgaga gcagaggcac aaacggcgca cagactgcat ccaacgtgct ccagtggttg 2161 gccgcaggct tttccattct cctgctcatg ttttacgcct accagacttg gaagtccaca 2221 tgtggctggg aggaaatcta cgtgtgtgca atcgaaatgg tgaaggtgat cctggagttt 2281 ttcttcgaat ttaaaaaccc aagcatgctg tacctggcta ctggccacag agtgcagtgg 2341 ctgcggtatg ccgaatggct gctgacttgc ccagtgattt gcatccacct gtccaacctg 2401 actgggctgt ctaacgatta cagtaggaga acaatgggac tgctcgtatc cgacatcggc 2461 actatcgtat ggggcgcaac tagtgccatg gccactggat acgtgaaagt gatcttcttc 2521 tgcctgggac tctgctacgg agcaaacaca ttttttcatg ccgcaaaagc atatatcgag 2581 gggtatcata ccgtcccaaa gggccggtgt agacaagtgg tgactggcat ggcttggctg 2641 ttcttcgtgt cctgggggat gtttcccatc ctctttatcc tgggcccaga aggcttcggg 2701 gtgctgagtg tgtatggcag taccgtagga cacactatca ttgacctgat gagcaaaaac 2761 tgctgggggc tgctcggcca ctacctgaga gtactcatcc acgagcatat cctgattcat 2821 ggcgatatcc ggaaaactac caagctcaat atcgggggca ccgagattga agtggagaca 2881 ctcgtggagg acgaggccga ggccggagca gtgaacaaag gcactggcaa gtatgcctcc 2941 agagaatcct ttctggtgat gcgggacaaa atgaaggaga aaggcattga tgtacggtgc 3001 agtaatgcca aagccgtcga gactgatgtg tag A single mutant ChR2 of the invention may be encoded by the following Synthetic construct hVChR1-mKate-betahChR2 (L132C) amino acid sequence (GenBank Accession No. AER29839, and SEQ ID NO: 10) with the following annotations, GFP sequence is in bold, L132C Chop2 sequence is underlined:

1 mdypvarsli vryptdlgng tvcmprgqcy cegwlrsrgt siektiaitl qwvvfalsva 61 clgwyayqaw ratcgweevy valiemmksi ieafhefdsp atlwlssgng vvwmrygewl 121 ltcpvllihl snltglkddy skrtmgllvs dvgcivwgat samctgwtki lfflislsyg 181 mytyfhaakv yieafhtvpk gicrelvrvm awtffvawgm fpvlfllgte gfghispygs 241 aighsildli aknmwgvlgn ylrvkihehi llygdirkkq kitiagqeme vetlvaeeed 301 gtavatmvsk geelikenmh mklymegtvn nhhfkctseg egkpyegtqt mrikvveggp

361 lpfafdilat sfmygsktfi nhtqgipdff kqsfpegftw ervttyedgg vltatqdtsl

421 qdgcliynvk irgvnfpsng pvmqkktlgw eastemlypa dgglegradm alklvggghl

481 icnlkttyrs kkpaknlkmp gvyyvdrrle rikeadkety veqhevavar ycdlpsklgh 541 klnclqekks csqrmaefrq ycwnpdtgqm lgrtparwvw islyyaafyv vmtglfalci 601 yvlmqtidpy tpdyqdqlks pgvtlrpdvy gerglqisyn isenssrqaq itgrpetetl 661 ppvdyggals avgrellfvt npvvvngsvl vpedqcycag wiesrgtnga qtasnvlqwl 721 aagfsilllm fyayqtwkst cgweeiyvca iemvkvilef ffefknpsml ylatghrvqw 781 lryaewlltc pvicihlsnl tglsndysrr tmgllvsdig tivwgatsam atgyvkviff -continued 841 clglcygant ffhaakayie gyhtvpkgrc rqvvtgmawl ffvswgmfpi lfilgpegfg 901 vlsvygstvg htiidlmskn cwgllghylr vlihehilih gdirkttkln iggteievet 961 lvedeaeaga vnkgtgkyas resflvmrdk mkekgidvrc snakavetdv A single mutant Chop2 of the invention may be encoded by the following Synthetic construct hVChR1-mKate-betahChR2 (L132C) gene sequence (GenBank Accession No. JN836745, and SEQ ID NO: 11) with the following annotations, GFP sequence is in bold, L132C Chop2 sequence is underlined:

1 atggattacc ctgtggcccg gtccctgatt gtaagatacc ccaccgatct gggcaatgga 61 accgtgtgca tgcccagagg acaatgctac tgcgaggggt ggctgaggag ccggggcact 121 agtatcgaaa aaaccatcgc tatcaccctc cagtgggtag tgttcgctct gtccgtagcc 181 tgtctcggct ggtatgcata ccaagcctgg agggctacct gtgggtggga ggaagtatac 241 gtggccctga tcgagatgat gaagtccatc atcgaggctt tccatgagtt cgactcccca 301 gccacactct ggctcagcag tgggaatggc gtagtgtgga tgagatatgg agagtggctg 361 ctgacctgtc ccgtcctgct cattcatctg tccaatctga ccgggctgaa agatgactac 421 tccaagagaa caatgggact gctggtgagt gacgtggggt gtattgtgtg gggagccacc 481 tccgccatgt gcactggatg gaccaagatc ctcttttcc tgatttccct ctcctatggg 541 atgtatacat acttccacgc cgctaaggtg tatattgagg ccttccacac tgtacctaaa 601 ggcatctgta gggagctcgt gcgggtgatg gcatggacct tctttgtggc ctgggggatg 661 ttccccgtgc tgttcctcct cggcactgag ggatttggcc acattagtcc ttacgggtcc 721 gcaattggac actccatcct ggatctgatt gccaagaata tgtgggggt gctgggaaat 781 tatctgcggg taaagatcca cgagcatatc ctgctgtatg gcgatatcag aaagaagcag 841 aaaatcacca ttgctggaca ggaaatggag gtggagacac tggtagcaga ggaggaggac 901 gggaccgcgg tcgccaccat ggtgtctaag ggcgaagagc tgattaagga gaacatgcac

961 atgaagctgt acatggaggg caccgtgaac aaccaccact tcaagtgcac atccgagggc

1021 gaaggcaagc cctacgaggg cacccagacc atgagaatca aggtggtcga gggcggccct

1081 ctccccttcg ccttcgacat cctggctacc agcttcatgt acggcagcaa aaccttcatc

1141 aaccacaccc agggcatccc cgacttcttt aagcagtcct tccctgaggg cttcacatgg

1201 gagagagtca ccacatacga agacgggggc gtgctgaccg ctacccagga caccagcctc

1261 caggacggct gcctcatcta caacgtcaag atcagagggg tgaacttccc atccaacggc

1321 cctgtgatgc agaagaaaac actcggctgg gaggcctcca ccgagatgct gtaccccgct

1381 gacggcggcc tggaaggcag agccgacatg gccctgaagc tcgtgggcgg gggccacctg

1441 atctgcaact tgaagaccac atacagatcc aagaaacccg ctaagaacct caagatgccc

1501 ggcgtctact atgtggacag aagactggaa agaatcaagg aggccgacaa agagacctac

1561 gtcgagcagc acgaggtggc tgtggccaga tactgcgacc tccctagcaa actggggcac 1621 aaacttaatt gcctgcagga gaagaagtca tgcagccagc gcatggccga attccggcaa 1681 tactgttgga acccggacac tgggcagatg ctgggccgca ccccagcccg gtgggtgtgg 1741 atcagcctgt actatgcagc tttctacgtg gtcatgactg ggctctttgc cttgtgcatc 1801 tatgtgctga tgcagaccat tgatccctac acccccgact accaggacca gttaaagtca 1861 ccgggggtaa ccttgagacc ggatgtgtat ggggaaagag ggctgcagat ttcctacaac 1921 atctctgaaa acagctctag acaggcccag atcaccggac gtccggagac tgagacattg 1981 ccaccggtgg actacggggg ggccctgagc gctgtgggca gagaactcct gttcgtgaca -continued 2041 aatccagtcg tggtgaacgg ctccgtactc gtacccgagg atcagtgcta ttgcgcagga 2101 tggatcgaga gcagaggcac aaacggcgca cagactgcat ccaacgtgct ccagtggttg 2161 gccgcaggct tttccattct cctgctcatg ttttacgcct accagacttg gaagtccaca 2221 tgtggctggg aggaaatcta cgtgtgtgca atcgaaatgg tgaaggtgat cctggagttt 2281 ttcttcgaat ttaaaaaccc aagcatgctg tacctggcta ctggccacag agtgcagtgg 2341 ctgcggtatg ccgaatggct gctgacttgc ccagtgattc tgatccacct gtccaacctg 2401 actgggctgt ctaacgatta cagtaggaga acaatgggac tgctcgtatc cgacatcggc 2461 actatcgtat ggggcgcaac tagtgccatg gccactggat acgtgaaagt gatcttcttc 2521 tgcctgggac tctgctacgg agcaaacaca ttttttcatg ccgcaaaagc atatatcgag 2581 gggtatcata ccgtcccaaa gggccggtgt agacaagtgg tgactggcat ggcttggctg 2641 ttcttcgtgt cctgggggat gtttcccatc ctctttatcc tgggcccaga aggcttcggg 2701 gtgctgagtg tgtatggcag taccgtagga cacactatca ttgacctgat gagcaaaaac 2761 tgctggggcc tgctcggcca ctacctgaga gtactcatcc acgagcatat cctgattcat 2821 ggcgatatcc ggaaaactac caagctcaat atcgggggca ccgagattga agtggagaca 2881 ctcgtggagg acgaggccga ggccggagca gtgaacaaag gcactggcaa gtatgcctcc 2941 agagaatcct ttctggtgat gcgggacaaa atgaaggaga aaggcattga tgtacggtgc 3001 agtaatgcca aagccgtcga gactgatgtg tag A single mutant Chop2 of the invention may be encoded by the following Synthetic construct hVChR1-mKate-betahChR2 (L132C) amino acid sequence (GenBank Accession No. AER29838, and SEQ ID NO: 12) with the following annotations, GFP sequence is in bold, L132C Chop2 sequence is undefined:

1 mdypvarsli vryptdlgng tvcmprgqcy cegwlrsrgt siektiaitl qwvvfalsva 61 clgwyayqaw ratcgweevy valiemmksi ieafhefdsp atlwlssgng vvwmrygewl 121 ltcpvllihl snltglkddy skrtmgllvs dvgcivwgat samctgwtki lfflislsyg 181 mytyfhaakv yieafhtvpk gicrelvrvm awtffvawgm fpvlfllgte gfghispygs 241 aighsildli aknmwgvlgn ylrvkihehi llygdirkkq kitiagqeme vetlvaeeed 301 gtavatmvsk geelikenmh mklymegtvn nhhfkctseg egkpyegtqt mrikvveggp

361 lpfafdilat sfmygsktfi nhtqgipdff kqsfpegftw ervttyedgg vltatqdtsl

421 qdgcliynvk irgvnfpsng pvmqkktlgw eastemlypa dgglegradm alklvggghl

481 icnlkttyrs kkpaknlkmp gvyyvdrrle rikeadkety veqhevavar ycdlpsklgh 541 klnclqekks csqrmaefrq ycwnpdtgqm lgrtparwvw islyyaafyv vmtglfalci 601 yvlmqtidpy tpdyqdqlks pgvtlrpdvy gerglqisyn isenssrqaq itgrpetetl 661 ppvdyggals avgrellfvt npvvvngsvl vpedqcycag wiesrgtnga qtasnvlqwl 721 aagfsilllm fyayqtwkst cgweeiyvca iemvkvilef ffefknpsml ylatghrvqw 781 lryaewlltc pvilihlsnl tglsndysrr tmgllvsdig tivwgatsam atgyvkviff 841 clglcygant ffhaakayie gyhtvpkgrc rqvvtgmawl ffvswgmfpi lfilgpegfg 901 vlsvygstvg htiidlmskn cwgllghylr vlihehilih gdirkttkln iggteievet 961 lvedeaeaga vnkgtgkyas resflvmrdk mkekgidvrc snakavetdv A L132C single mutant Chop2 of the invention may be encoded by the following amino acid sequence (positions 132 underlined and bolded, SEQ ID NO: 13):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ICIHLSNLTG LSNDYSRRTM GLLVSDIGTI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A T159C single mutant Chop2 of the invention may be encoded by the following amino acid sequence (positions 159 underlined and bolded, SEQ ID NO: 14):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ILIHLSNLTG LSNDYSRRTM GLLVSDIGCI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A L132C/T159C double mutant Chop2 of the invention may be encoded by the following nucleotide sequence (SEQ ID NO: 15):

```
  1 atggactacg ggggggctct gtctgctgtc gggagggaac tgctgtttgt gactaaccct
 61 gtcgtcgtga acgggagtgt gctggtccct gaggaccagt gctactgtgc cggctggatc
121 gaatcacgcg gaaccaacgg ggcccagaca gctagcaatg tgctgcagtg gctggccgct
181 gggtttagta tcctgctgct gatgttctac gcctatcaga cttggaagtc aacctgcggc
241 tgggaggaaa tctacgtgtg cgctattgag atggtgaaag tgatcctgga gttcttcttc
301 gagttcaaga acccaagcat gctgtacctg gctactggac accgagtgca gtggctgaga
361 tatgcagaat ggctgctgac atgccccgtc atctgcattc acctgtccaa cctgacaggc
421 ctgagcaatg actactccag gagaactatg ggactgctgg tgtccgacat cggctgcatt
481 gtctggggag caacttctgc tatggcaacc ggatacgtga aggtcatctt tttctgcctg
541 gggctgtgct atggcgcaaa tacctttttc cacgcagcca aggcctacat tgaggggtat
601 cataccgtgc caaaaggccg gtgccgacag gtggtcacag gaatggcttg gctgtttttc
661 gtctcttggg gaatgtttcc catcctgttc attctggggc ctgaagggtt cggcgtgctg
721 tctgtctacg gaagtacagt ggggcatact atcattgacc tgatgtccaa aaactgttgg
781 ggcctgctgg gacactatct gagagtgctg atccacgagc atatcctgat tcatggcgat
841 attcggaaga ccacaaaact gaatatcggc ggaaccgaga ttgaagtgga aacactggtg
901 gaagacgagg ctgaggctgg ggctgtgaac aaggggactg gcaaa
```

A L132C/T159C double mutant Chop2 of the invention may be encoded by the following amino acid sequence (positions 132 and 159 underlined and bolded, SEQ ID NO: 16):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ICIHLSNLTG LSNDYSRRTM GLLVSDIGCI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A T159S single mutant Chop2 of the invention may be encoded by the following amino acid sequence (positions 159 underlined and bolded, SEQ ID NO: 17):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ILIHLSNLTG LSNDYSRRTM GLLVSDIGSI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A L132C/T159S double mutant Chop2 of the invention may be encoded by the following nucleotide sequence (SEQ ID NO: 18):

```
  1 atggactacg gggggcgctct gtctgctgtc gggagggaac tgctgtttgt gactaaccct
 61 gtcgtcgtga acgggagtgt gctggtccct gaggaccagt gctactgtgc cggctggatc
121 gaatcacgcg gaaccaacgg ggcccagaca gctagcaatg tgctgcagtg gctggccgct
181 gggtttagta tcctgctgct gatgttctac gcctatcaga cttggaagtc aacctgcggc
241 tgggaggaaa tctacgtgtg cgctattgag atggtgaaag tgatcctgga gttcttcttc
301 gagttcaaga acccaagcat gctgtacctg gctactggac accgagtgca gtggctgaga
361 tatgcagaat ggctgctgac atgccccgtc atctgcattc acctgtccaa cctgacaggc
421 ctgagcaatg actactccag gagaactatg ggactgctgg tgtccgacat cggcagcatt
481 gtctggggag caacttctgc tatggcaacc ggatacgtga aggtcatctt tttctgcctg
541 gggctgtgct atggcgcaaa tacctttttc cacgcagcca aggcctacat tgaggggtat
601 cataccgtgc caaaaggccg gtgccgacag gtggtcacag gaatggcttg gctgtttttc
661 gtctcttggg gaatgtttcc catcctgttc attctggggc ctgaagggtt cggcgtgctg
721 tctgtctacg gaagtacagt ggggcatact atcattgacc tgatgtccaa aaactgttgg
781 ggcctgctgg gacactatct gagagtgctg atccacgagc atatcctgat tcatggcgat
841 attcggaaga ccacaaaact gaatatcggc ggaaccgaga ttgaagtgga aacactggtg
901 gaagacgagg ctgaggctgg ggctgtgaac aaggggactg gcaaa
```

A L132C/T159S double mutant Chop2 of the invention may be encoded by the following amino acid sequence (positions 132 and 159 underlined and bolded, SEQ ID NO: 19):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ICIHLSNLTG LSNDYSRRTM GLLVSDIGSI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A L132A single mutant Chop2 of the invention may be encoded by the following amino acid sequence (position 132 underlined and bolded, SEQ ID NO: 20):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV IAIHLSNLTG LSNDYSRRTM GLLVSDIGTI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A L132A/T159C double mutant Chop2 of the invention may be encoded by the following nucleotide sequence (SEQ ID NO: 21):

```
  1 ATGGACTACG GGGGGGCTCT GTCTGCTGTC GGGAGGGAAC TGCTGTTTGT GACTAACCCT
 61 GTCGTCGTGA ACGGGAGTGT GCTGGTCCCT GAGGACCAGT GCTACTGTGC CGGCTGGATC
121 GAATCACGCG GAACCAACGG GGCCCAGACA GCTAGCAATG TGCTGCAGTG GCTGGCCGCT
181 GGGTTTAGTA TCCTGCTGCT GATGTTCTAC GCCTATCAGA CTTGGAAGTC AACCTGCGGC
241 TGGGAGGAAA TCTACGTGTG CGCTATTGAG ATGGTGAAAG TGATCCTGGA GTTCTTCTTC
301 GAGTTCAAGA ACCCAAGCAT GCTGTACCTG GCTACTGGAC ACCGAGTGCA GTGGCTGAGA
361 TATGCAGAAT GGCTGCTGAC ATGCCCCGTC ATCGCCATTC ACCTGTCCAA CCTGACAGGC
421 CTGAGCAATG ACTACTCCAG GAGAACTATG GGACTGCTGG TGTCCGACAT CGGCTGCATT
481 GTCTGGGGAG CAACTTCTGC TATGGCAACC GGATACGTGA AGGTCATCTT TTTCTGCCTG
541 GGGCTGTGCT ATGGCGCAAA TACCTTTTTC CACGCAGCCA AGGCCTACAT TGAGGGGTAT
601 CATACCGTGC CAAAAGGCCG GTGCCGACAG GTGGTCACAG GAATGGCTTG GCTGTTTTTC
661 GTCTCTTGGG GAATGTTTCC CATCCTGTTC ATTCTGGGGC CTGAAGGGTT CGGCGTGCTG
721 TCTGTCTACG GAAGTACAGT GGGGCATACT ATCATTGACC TGATGTCCAA AAACTGTTGG
781 GGCCTGCTGG GACACTATCT GAGAGTGCTG ATCCACGAGC ATATCCTGAT TCATGGCGAT
841 ATTCGGAAGA CCACAAAACT GAATATCGGC GGAACCGAGA TTGAAGTGGA AACACTGGTG
901 GAAGACGAGG CTGAGGCTGG GGCTGTGAAC AAGGGGACTG GCAAA
```

A L132A/T159C double mutant Chop2 of the invention may be encoded by the following amino acid sequence (positions 132 and 159 underlined and bolded, SEQ ID NO: 22):

1 MDYGGALSAV GRELLFVTNP VVVNGSVLVP EDQCYCAGWI ESRGTNGAQT ASNVLQWLAA

61 GFSILLLMFY AYQTWKSTCG WEEIYVCAIE MVKVILEFFF EFKNPSMLYL ATGHRVQWLR

121 YAEWLLTCPV IAIHLSNLTG LSNDYSRRTM GLLVSDIGCI VWGATSAMAT GYVKVIFFCL

181 GLCYGANTFF HAAKAYIEGY HTVPKGRCRQ VVTGMAWLFF VSWGMFPILF ILGPEGFGVL

241 SVYGSTVGHT IIDLMSKNCW GLLGHYLRVL IHEHILIHGD IRKTTKLNIG GTEIEVETLV

301 EDEAEAGAVN KGTGK

A T159A single mutant Chop2 of the invention may be encoded by the following amino acid sequence (position 159 underlined and bolded, SEQ ID NO: 23):

1 MDYGGALSAV GRELLFVTNP VVVNGSVLVP EDQCYCAGWI ESRGTNGAQT ASNVLQWLAA

61 GFSILLLMFY AYQTWKSTCG WEEIYVCAIE MVKVILEFFF EFKNPSMLYL ATGHRVQWLR

121 YAEWLLTCPV ILIHLSNLTG LSNDYSRRTM GLLVSDIGAI VWGATSAMAT GYVKVIFFCL

181 GLCYGANTFF HAAKAYIEGY HTVPKGRCRQ VVTGMAWLFF VSWGMFPILF ILGPEGFGVL

241 SVYGSTVGHT IIDLMSKNCW GLLGHYLRVL IHEHILIHGD IRKTTKLNIG GTEIEVETLV

301 EDEAEAGAVN KGTGK

A L132C/T159A double mutant Chop2 of the invention may be encoded by the following nucleotide sequence (SEQ ID NO: 24):

1 atggactacg ggggggctct gtctgctgtc gggagggaac tgctgtttgt gactaaccct 61 gtcgtcgtga acgggagtgt gctggtccct gaggaccagt gctactgtgc cggctggatc 121 gaatcacgcg gaaccaacgg ggcccagaca gctagcaatg tgctgcagtg gctggccgct 181 gggtttagta tcctgctgct gatgttctac gcctatcaga cttggaagtc aacctgcggc 241 tgggaggaaa tctacgtgtg cgctattgag atggtgaaag tgatcctgga gttcttcttc 301 gagttcaaga acccaagcat gctgtacctg gctactggac accgagtgca gtggctgaga 361 tatgcagaat ggctgctgac atgccccgtc atctgcattc acctgtccaa cctgacaggc 421 ctgagcaatg actactccag gagaactatg ggactgctgg tgtccgacat cggcgccatt 481 gtctggggag caacttctgc tatggcaacc ggatacgtga aggtcatctt tttctgcctg 541 gggctgtgct atggcgcaaa taccttttc cacgcagcca aggcctacat tgaggggtat 601 cataccgtgc caaaaggccg gtgccgacag gtggtcacag gaatggcttg gctgtttttc 661 gtctcttggg gaatgtttcc catcctgttc attctggggc ctgaagggtt cggcgtgctg 721 tctgtctacg gaagtacagt ggggcatact atcattgacc tgatgtccaa aaactgttgg 781 ggcctgctgg gacactatct gagagtgctg atccacgagc atatcctgat tcatggcgat 841 attcggaaga ccacaaaact gaatatcggc ggaaccgaga ttgaagtgga aacactggtg 901 gaagacgagg ctgaggctgg ggctgtgaac aaggggactg gcaaa A L132C/T159A double mutant Chop2 of the invention may be encoded by the following amino acid sequence (positions 132 and 159 underlined and bolded, SEQ ID NO: 25):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ICIHLSNLTG LSNDYSRRTM GLLVSDIGAI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A wild type (WT) Chop2 of the invention may be encoded by the following amino acid sequence (SEQ ID NO: 26):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ILIHLSNLTG LSNDYSRRTM GLLVSDIGTI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

Mutant ChR2 proteins of the invention also demonstrate slower channel kinetics. Higher light sensitivity was found to correlate with slower channel kinetics, indicating a trade-off between light sensitivity and channel kinetics. Chop2 proteins that form the ChR2 proteins of the present invention may also comprise additional mutations or modifications that may improve channel kinetics, or increase the deactivation rate, of the ChR2. Particularly preferred ChR2 mutants balance the threshold of light sensitivity with channel kinetics.

Compositions and Kits

Compositions and kits of the invention comprise at least one nucleic acid molecule or polypeptide molecule that encodes a mutant Chop2 protein, and the resulting ChR2, of the invention. The at least one nucleic acid molecule or polypeptide molecule that encodes a mutant Chop2 protein of the invention may further include a pharmaceutically-acceptable carrier. Kits of the invention further include instructions for administering a composition of the invention to a subject.

Therapeutic Uses

Mutations were made on a codon optimized Chop2-GFP fusion protein to create single and double mutations at the L132 (Leucine 132) and T159 (threonine 159) sites. The functional properties of each mutant ChR2, or a combination thereof, were first examined in HEK cells. AAV2 virus vectors carrying mutant Chop2-GFP constructs driven by CAG promoter were made and injected intravitreally into the eyes of adult mice. Mutant Chop2-mediated light responses were examined by using multi-electrode array recordings from whole-mount retinas.

Single mutant ChR2, i.e., L132 and T159C, markedly lower the threshold light intensity that is required to evoke a ChR2-mediated photocurrent. Moreover, several double mutant ChR2 variants, including L132C/T159C, L132A/T159C, and L132C/T159S, were found to further increase the photocurrent above the results of any single mutant ChR2 at low light intensities. The double mutants exhibited a slower off-rate, which is likely to contribute to the increased photocurrent at the low light intensities. Spiking activity of retinal ganglion cells mediated by the L132C/T159C double mutant was observed at the light intensity of $10^{13}$ photon/cm$^2$/s and at the wavelength of 473 nm. This light level is about 1.5 to 2 log units lower than the light level that is required to elicit the spiking activity with wild-type ChR2. The spike firing of retinal ganglion cells expressing L132C/T159C could follow a light flicker frequency of up to 15 Hz. Ongoing studies are evaluating the long-term expression and safety of mutant ChR2s of the invention in retinal neurons.

Furthermore, expression of the mutant Chop2 proteins, and the resulting ChR2 proteins, of the present invention was not found to cause neurotoxicity of up to two months after viral injection in mice, demonstrating the safety of the present invention for therapeutic use.

Vectors for use in the present invention can include various viral vectors, such as plasmids and recombinant viruses, i.e., recombinant adeno-associated virus (rAAV), recombinant adenoviruses, recombinant retroviruses, recombinant lentiviruses, and other viruses known in the art.

In some embodiments, the expression of the Chop2 proteins of the present invention is driven by a constitutive promoter, i.e., CAG promoter, CMV promoter, LTR. In other embodiments, the promoter is an inducible or a cell-specific promoter. Cell type-specific promoters that enable Chop2 protein expression in specific subpopulations of cells, i.e., retinal neuron cells or degenerating cells, may be preferred. These cells may include, but are not limited to, a retinal ganglion cell, a photoreceptor cell, a bipolar cell, a rod bipolar cell, an ON-type cone bipolar cell, a retinal ganglion cell, a photosensitive retinal ganglion cell, a horizontal cell, an amacrine cell, or an AII amacrine cell. Cell type-specific promoters are well known in the art. Particularly preferred cell type-specific promoters include, but are not limited to mGluR6, NK-3, and Pcp2 (L7).

In some embodiments, use of different opsin genes in addition to the mutant Chop2 proteins of the present invention and targeted gene expression may further increase light sensitivity or improve vision. Visual information is processed through the retina through two pathways: an ON pathway which signals the light ON, and an OFF pathway which signals the light OFF. The existence of the ON and OFF pathway is important for the enhancement of contrast sensitivity. The visual signal in the ON pathway is relay from ON-cone bipolar cells to ON ganglion cells. Both ON-cone bipolar cells and ON-ganglion cells are depolarized in response to light. On the other hand, the visual signal in the OFF pathway is carried from OFF-cone bipolar cells to OFF ganglion cells. Both OFF-cone bipolar cells and OFF-ganglion cells are hypopolarized in response to light. Rod bipolar cells, which are responsible for the ability to see in dim light (scotopic vision), are ON bipolar cells (depolarized in response to light). Rod bipolar cells relay the vision signal through AII amacrine cells (an ON type retinal cells) to ON an OFF cone bipolar cells.

Accordingly, a dual rhodopsin system can be used to recapitulate the ON and OFF pathways integral to visual processing and acuity. Briefly, a Chop2 protein of the present invention can be specifically targeted to ON type retinal neurons (i.e., ON type ganglion cells and/or ON type bipolar cells), while a hypopolarizing light sensor (i.e., halorhodopsin or other chloride pump known in the art) can be targeted to OFF type retinal neurons (i.e. OFF type ganglion cells and/or OFF type bipolar cells) to create ON and OFF pathways. The specific targeting to preferred cell subpopulations can be achieved through the use of different cell type-specific promoters. For example, Chop2 expression may be driven by the mGluR6 promoter for targeted expression in ON-type retinal neurons (i.e., ON type ganglion cells and/or ON type bipolar cells) while a hypopolarizing channel, such as halorhodopsin, expression is driven by the NK-3 promoter for targeted expression in OFF-type retinal neurons (i.e., OFF type ganglion cells and/or OFF type bipolar cells).

An alternative approach to restore ON and OFF pathways in the retina is achieved by, expressing a depolarizing light sensor, such as ChR2, to rod bipolar cells or AII amacrine. In this approach, the depolarization of rod bipolar cells or AII amacrine cells can lead to the ON and OFF responses at the levels of cone bipolar cells and the downstream retinal ganglion cells. Thus, the ON and OFF pathways that are inherent in the retina are maintained.

The present invention can be formulated to a pharmaceutical composition or medicament suitable for administration into a subject or patient. Suitable routes of administration include, for example, intravitreal, intraocular, or subretinal injection.

Such formulations comprise a pharmaceutically and/or physiologically acceptable vehicle, diluent, carrier or excipient, such as buffered saline or other buffers, e.g., HEPES, to maintain physiologic pH. For a discussion of such components and their formulation, see, generally, Gennaro, A E., *Remington: The Science and Practice of Pharmacy*. Lippincott Williams & Wilkins Publishers: 2003 or latest edition). See also, WO00/15822. If the preparation is to be stored for long periods, it may be frozen, for example, in the presence of glycerol.

The pharmaceutical composition described above is administered to a subject having a visual or blinding disease by any appropriate route, preferably by intravitreal or subretinal injection, depending on the retinal layer being targeted.

Disclosures from Bennett and colleagues (cited herein) concern targeting of retinal pigment epithelium—the most distal layer from the vitreal space. According to the present invention, the Chop2 construct or polypeptide is targeted to retinal cells, i.e., retinal ganglion cells or bipolar cells. Such cells are known to be reasonably well-accessible to intravitreal injection as disclosed herein. Intravitreal and/or subretinal injection can provide the necessary access to the bipolar cells, especially in circumstances in which the photoreceptor cell layer is absent due to degeneration—which is the case in certain forms of degeneration that the present invention is intended to overcome.

To test for the vector's ability to express the Chop2 mutants of the present invention, specifically in mammalian retinal neurons, by AAV-mediated delivery, a combination of a preferred promoter sequence linked to a reporter gene such as LacZ or GFP linked to a SV40 poly A sequence can be inserted into a plasmid and packaged into rAAV virus particles, concentrated, tested for contaminating adenovirus and titered for rAAV using an infectious center assay. The right eyes of a number of test subjects, preferably inbred mice, can be injected sub-retinally with about 1 μl of the rAAV preparation (e.g., greater than about $10^{10}$ infectious units ml). Two weeks later, the right (test) and left (control) eyes of half the animals may be removed, fixed and stained with an appropriate substrate or antibody or other substance to reveal the presence of the reporter gene. A majority of the test retinas in injected eyes will exhibited a focal stained region, e.g., blue for LacZ/Xgal, or green for GFP consistent with a subretinal bleb of the injected virus creating a localized retinal detachment. All control eyes may be negative for the reporter gene product. Reporter gene expression examined in mice sacrificed at later periods is detected for at least 10 weeks post-injection, which suggests persistent expression of the reporter transgene.

In one embodiment, the Chop2 constructs are packaged in adenoviral vectors for transgene delivery. An effective amount of rAAV virions carrying a nucleic acid sequence encoding the Chop2 DNA under the control of the promoter of choice, preferably a constitutive CMV promoter or a cell-specific promoter such as mGluR6, is preferably in the range of between about $10^{10}$ to about $10^{13}$ rAAV infectious units in a volume of between about 150 and about 800 μl per injection. The rAAV infectious units can be measured according to McLaughlin, S K et al., 1988, *J Virol* 62:1963. More preferably, the effective amount is between about $10^{10}$ and about $10^{12}$ rAAV infectious units and the injection volume is preferably between about 250 and about 500 μl. Other dosages and volumes, preferably within these ranges but possibly outside them, may be selected by the treating professional, taking into account the physical state of the subject (preferably a human), who is being treated, including, age, weight, general health, and the nature and severity of the particular ocular disorder.

It may also be desirable to administer additional doses ("boosters") of the present nucleic acid(s) or rAAV compositions. For example, depending upon the duration of the transgene expression within the ocular target cell, a second treatment may be administered after 6 months or yearly, and may be similarly repeated. Neutralizing antibodies to AAV are not expected to be generated in view of the routes and doses used, thereby permitting repeat treatment rounds.

The need for such additional doses can be monitored by the treating professional using, for example, well-known electrophysiological and other retinal and visual function tests and visual behavior tests. The treating professional will be able to select the appropriate tests applying routine skill in the art. It may be desirable to inject larger volumes of the composition in either single or multiple doses to further improve the relevant outcome parameters.

Ocular Disorders

The ocular disorders for which the present Chop2 proteins, and the resulting ChR2 proteins, are intended and may be used to improve one or more parameters of vision include, but are not limited to, developmental abnormalities that affect both anterior and posterior segments of the eye. Anterior segment disorders include glaucoma, cataracts, corneal dystrophy, keratoconus. Posterior segment disorders include blinding disorders caused by photoreceptor malfunction and/or death caused by retinal dystrophies and degenerations. Retinal disorders include congenital stationary night blindness, age-related macular degeneration, congenital cone dystrophies, and a large group of retinitis-pigmentosa (RP)-related disorders. These disorders include genetically pre-disposed death of photoreceptor cells, rods and cones in the retina, occurring at various ages. Among those are severe retinopathies, such as subtypes of RP itself that progresses with age and causes blindness in childhood and early adulthood and RP-associated diseases, such as genetic subtypes of LCA, which frequently results in loss of vision during childhood, as early as the first year of life. The latter disorders are generally characterized by severe reduction, and often complete loss of photoreceptor cells, rods and cones. (Trabulsi, E I, ed., *Genetic Diseases of the Eye*. Oxford University Press, NY, 1998).

In particular, the Chop2 and ChR2 proteins of the present invention useful for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by the Chop2 and ChR2 proteins of the present invention. Thus, the particular ocular disorder treated by the present invention may include the above-mentioned disorders and a number of diseases which have yet to be so characterized.

Optogenetics

The emerging field of optogenetics involves the combination of genetic and optical methods to control specific events in targeted cells of a living tissue. Optogenetics may be used within freely moving mammals and other animals. Moreover, the temporal precision (millisecond-timescale) of optogenetic methods are sufficient to function within intact biological systems.

The instant invention provides Chop2-gene therapy to retinal tissues of the eye, by introducing into retinal cells a nucleic acid or polypeptide encoding for at least one mutant form of Chop2. Mutant Chop2/ChR2 proteins of the invention are specifically adapted to be light-activated at lower thresholds of light intensities than their wild type counterparts. Accordingly, the mutant Chop2/ChR2 proteins of the invention can be used to activate cells of the retina and visual system using less damaging sources of illumination. The mutant Chop2/ChR2 proteins also conduct larger photocurrents upon activation, resulting in a more robust or efficacious response from the mutant Chop2/ChR2-expressing cells.

For example, mutant Chop2 proteins of the invention are administered to a subject through local, intravitreous or subretinal, injection of a nucleic acid molecule encoding a mutant Chop2, a mutant Chop2 polypeptide molecule, or a cell expressing a mutant Chop2/ChR2. Retinal cells of the subject express the mutant Chop2 proteins within the plasma membrane. When the transfected or transformed retinal cells encounter light radiation, the transfected or transformed retinal cells transduce an improved or restored signal.

These methods may be used in subjects of normal and/or impaired vision. Chop2/ChR2 mutants of the invention may preserve, improve, or restore vision. Moreover, Chop2/ChR2 mutants of the invention are used to preserve, improve, or restore the transduction of non-visual information from photosensitive retinal ganglion cells to the brain.

The term "vision" as used herein is defined as the ability of an organism to usefully detect light as a stimulus for differentiation or action. Vision is intended to encompass the following:

1. Light detection or perception—the ability to discern whether or not light is present;
2. Light projection—the ability to discern the direction from which a light stimulus is coming;
3. Resolution—the ability to detect differing brightness levels (i.e., contrast) in a grating or letter target; and
4. Recognition—the ability to recognize the shape of a visual target by reference to the differing contrast levels within the target.

Thus, "vision" includes the ability to simply detect the presence of light. The polypeptides and polynucleotides encoding mutant Chop2 of the present invention can be used to improve or restore vision, wherein the improvement or restoration in vision includes, for example, increases in light detection or perception, increase in light sensitivity or photosensitivity in response to a light stimulus, increase in the ability to discern the direction from which a light stimulus is coming, increase in the ability to detect differing brightness levels, increase in the ability to recognize the shape of a visual target, and increases in visual evoked potential or transmission from the retina to the cortex. As such, improvement or restoration of vision may or may not include full restoration of sight, i.e., wherein the vision of the patient treated with the present invention is restored to the degree to the vision of a non-affected individual. The visual recovery described in the animal studies described below may, in human terms, place the person on the low end of vision function by increasing one aspect of vision (i.e., light sensitivity, or visual evoked potential) without restoring full sight. Nevertheless, placement at such a level would be a significant benefit because these individuals could be trained in mobility and potentially in low order resolution tasks which would provide them with a greatly improved level of visual independence compared to total blindness. Even basic light perception can be used by visually impaired individuals, whose vision is improved using the present compositions and methods, to accomplish specific daily tasks and improve general mobility, capability, and quality of life.

The degree of restoration of vision can be determined through the measurement of vision before, and preferably after, administering a vector comprising, for example, DNA encoding Chop2. Vision can be measured using any of a number of methods well-known in the art or methods not yet established. Vision, as improved or restored by the present invention, can be measured by any of the following visual responses:

1. a light detection response by the subject after exposure to a light stimulus—in which evidence is sought for a reliable response of an indication or movement in the general direction of the light by the subject individual when the light it is turned on;
2. a light projection response by the subject after exposure to a light stimulus in which evidence is sought for a reliable response of indication or movement in the specific direction of the light by the individual when the light is turned on;
3 light resolution by the subject of a light vs. dark patterned visual stimulus, which measures the subject's capability of resolving light vs dark patterned visual stimuli as evidenced by:
a. the presence of demonstrable reliable optokinetically produced nystagmoid eye movements and/or related head or body movements that demonstrate tracking of the target (see above) and/or
b. the presence of a reliable ability to discriminate a pattern visual stimulus and to indicate such discrimination by verbal or non-verbal means, including, for example pointing, or pressing a bar or a button: or
4. electrical recording of a visual cortex response to a light flash stimulus or a pattern visual stimulus, which is an endpoint of electrical transmission from a restored retina to the visual cortex, also referred to as the visual evoked potential (VEP). Measurement may be by electrical recording on the scalp surface at the region of the visual cortex, on the cortical surface, and/or recording within cells of the visual cortex.

Thus, improvement or restoration of vision, according to the present invention, can include, but is not limited to: increases in amplitude or kinetics of photocurrents or electrical response in response to light stimulus in the retinal cells, increases in light sensitivity (i.e., lowering the threshold light intensity required for initiating a photocurrent or electrical response in response to light stimulus, thereby requiring less or lower light to evoke a photocurrent) of the retinal cells, increases in number or amplitude of light-evoked spiking or spike firings, increases in light responses to the visual cortex, which includes increasing in visual evoked potential transmitted from the retina or retinal cells to the visual cortex or the brain.

Both in vitro and in vivo studies to assess the various parameters of the present invention may be used, including recognized animal models of blinding human ocular disorders. Large animal models of human retinopathy, e.g., childhood blindness, are useful. The examples provided herein allow one of skill in the art to readily anticipate that this method may be similarly used in treating a range of retinal diseases.

While earlier studies by others have demonstrated that retinal degeneration can be retarded by gene therapy techniques, the present invention demonstrates a definite physiological recovery of function, which is expected to generate or improve various parameters of vision, including behavioral parameters.

Behavioral measures can be obtained using known animal models and tests, for example performance in a water maze, wherein a subject in whom vision has been preserved or restored to varying extents will swim toward light (Hayes, J M et al., 1993, *Behav Genet* 23:395-403).

In models in which blindness is induced during adult life or congenital blindness develops slowly enough that the individual experiences vision before losing it, training of the subject in various tests may be done. In this way, when these tests are re-administered after visual loss to test the efficacy of the present compositions and methods for their vision-restorative effects, animals do not have to learn the tasks de novo while in a blind state. Other behavioral tests do not require learning and rely on the instinctiveness of certain behaviors. An example is the optokinetic nystagmus test (Balkema G W et al., 1984, *Invest Ophthalmol Vis Sci.* 25:795-800; Mitchiner J C et al., 1976, *Vision Res.* 16:1169-71).

The present invention may also be used in combination with other forms of vision therapy known in the art to improve or restore vision. For example, the use of visual prostheses, which include retinal implants, cortical implants, lateral *geniculate* nucleus implants, or optic nerve implants. Thus, in addition to genetic modification of surviving retinal neurons using the present methods, the subject being treated may be provided with a visual prosthesis before, at the same time as, or after the molecular method is employed. The effectiveness of visual prosthetics can be improved with training of the individual, thus enhancing the potential impact of the Chop2 transformation of patient cells as contemplated herein. Training methods, such as habituation training characterized by training the subject to recognize (i) varying levels of light and/or pattern stimulation, and/or (ii) environmental stimulation from a common light source or object as would be understood by one skilled in the art; and orientation and mobility training characterized by training the subject to detect visually local objects and move among said objects more effectively than without the training. In fact, any visual stimulation techniques that are typically used in the field of low vision rehabilitation are applicable here.

EXAMPLES

Example 1: Generation of Labeled Mutant Chop2 Constructs

Mutations were made on a codon optimized Chop2-GFP fusion protein to create single and double mutations at the L132 (Leucine 132) and T159 (Threonine 159) sites. Several mutants were generated, for example, single mutants such as L132A, L132C, T159A, T159C, and T 159S, and double mutants such as L132C/T159C, L132C/T159S, L132A/T159C, and L132C/T159A. Chop2-GFP transgenes were cloned into a rAAV vector under the control of a CAG promoter using methods known in the art.

Example 2: In Vitro Analysis of Mutant Chop2 Constructs

The functional properties of each mutant Chop2, or a combination thereof, were first examined in HEK cells. Chop2 constructs were delivered to HEK cells by adenoviral infection, for example. Upon expression of the WT or mutant Chop2, functional WT and mutant ChR2 channels were formed. Measurements of the light sensitivity and other properties of the ChR2 channels were assessed as described herein. The light stimuli (photons/$cm^2$·s at 460 nm) were generated by a xenon arc lamp and attenuated by neutral density filters: ND4.0 ($2.8\times10^{14}$), ND3.0 ($1.4\times10^{15}$), ND2.5 ($4.8\times10^{15}$): ND2.0 ($1.6\times10^{16}$), ND1.0 ($1.3\times10^{17}$), ND0 ($1.2\times10^{18}$). Light evoked currents were measured from wild-type ChR2, T159C, L132C, L132C/T159C, and L132C/T159S. Patch clamp recordings were performed using methods known in the art.

Figure 1B:
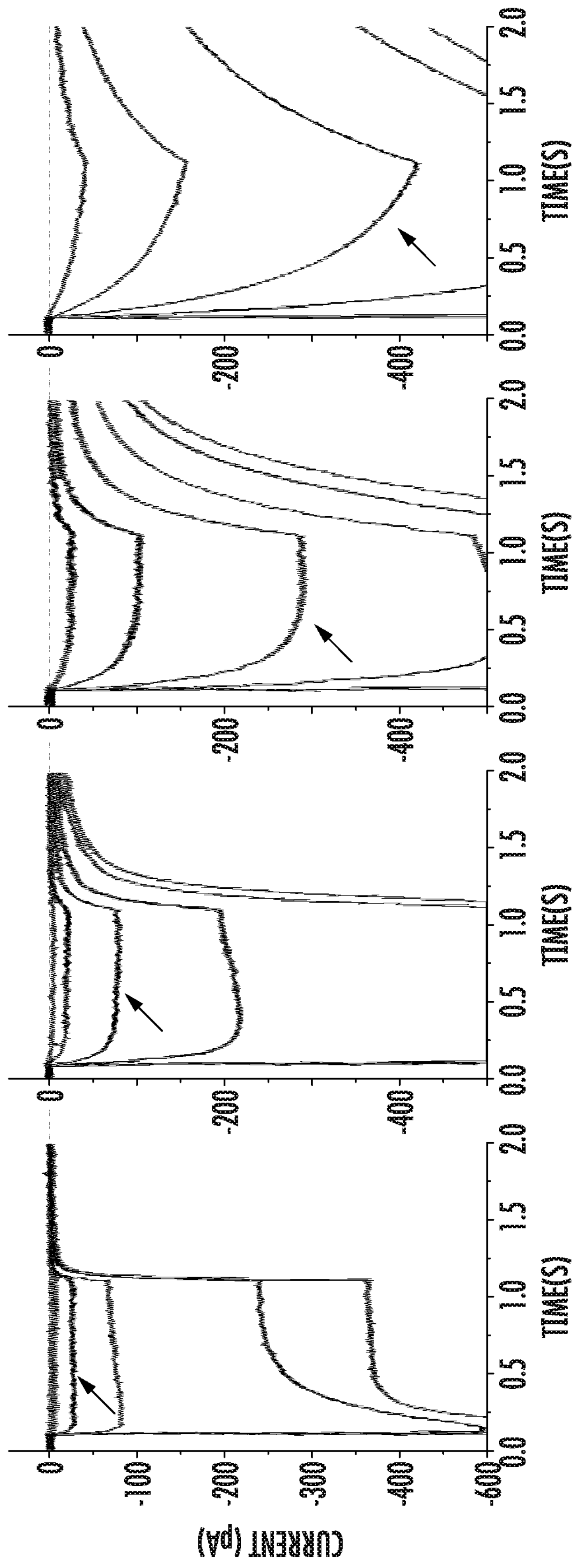

Representative recordings from this experiment comparing light sensitivity between the Chop2 constructs demonstrated that mutations at L132 alone or in combination with mutation at T159 show increased photocurrent in comparison to WT (FIGS. 1A and 1B). FIG. 1B shows the same current traces at a different scale to illustrate the difference in amplitude of the photocurrents between WT ChR2 and ChR2 mutants more clearly. FIG. 1B specifically compares the current traces resulting from light stimulation using the neutral density filter (ND 2.5), equivalent to $4.8\times10^{15}$ photos/cm$^2$/s: the traces are designated by the arrows. The amplitude of the photocurrent of the L132C mutant is larger than that of WT: the amplitude of the photocurrent of double mutant L132C/T159C is larger than that of L132C; and the amplitude of the photocurrent of the L132C/T159S mutant larger than L132/T159C. The current traces of the ChR2 mutants, particularly double mutants L132C/T159C and L132C/T159S, also show slower deactivation kinetics when compared to WT and L132C.

Figure 2:
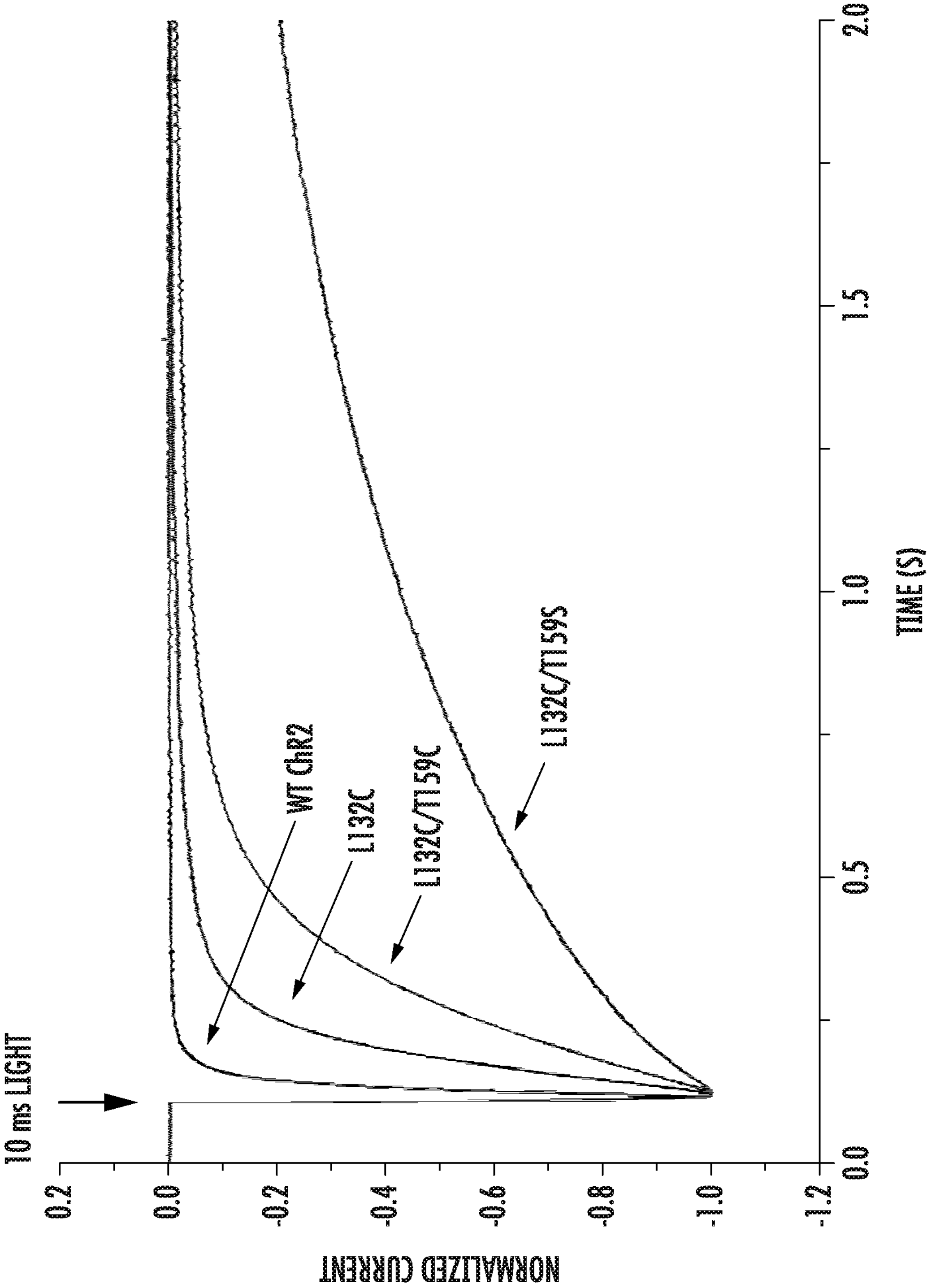
FIG. 2 shows representative recordings of the light-evoked currents from wild-type (WT) ChR2, T159C, L132C, L132C/T159C, and L132C/T159S mutants to a 10 ms light pulse (1.2×10$^{18}$ photons/cm$^2$/s at 460 nm) in HEK cells for comparison of their deactivation time course (decay time course after light off).

FIG. 2 shows the representative recordings of light-evoked currents from WT ChR2, L132C, L132C/T159C, and L132C/T159S after stimulation by a 10 ms light pulse ($1.2\times10^{18}$ photons/cm$^2$/s at 460 nm wavelength) to compare the deactivation time course, or decay time course after the light is off. Mutant ChR2 show longer deactivation time courses, with the double mutant L132C/T159S having the longest. Higher light sensitivity, as demonstrated by L132C/T159C and L132C/T159S, may be correlated with slower channel kinetics.

Example 3: In Vivo Ocular Administration and Analysis of Mutant Chop2 Constructs AAV2 virus vectors carrying mutant Chop2-GFP constructs driven by CAG promoter were made and injected intravitreally into the eyes of C57BL/6J adult mice. Adult mice were anesthetized by IP injection of ketamine (100 mg/kg) and xylazine (10 mg/kg). Under a dissecting microscope, an incision was made by scissors through the eyelid to expose the sclera. A small perforation was made in the sclera region posterior to the lens with a needle and viral vector suspension of 0.8-1.5 μl at the concentration of approximately $10^{11}$ genomic particles/ml was injected into intravitreal space through the hole with a Hamilton syringe with a 32-gauge blunt-ended needle. For each animal, usually only one eye was injected with viral vectors carrying a Chop2 construct, and the other eye was uninjected or injected with control viral vectors carrying GFP alone. Upon expression of the WT or mutant Chop2 of the present invention, functional WT or mutant ChR2 channels were formed utilizing endogenous retinal, and the properties of these ChR2 proteins were assessed as described herein.

ChR2-mediated light responses were examined by using multi-electrode array recordings from whole-mount retinas. Light stimuli (photons/cm$^2$/s) was generated by a 473 nm blue laser and attenuated by neutral density filters: ND0 ($6.3\times10^{16}$), ND1.0 ($7.4\times10^{15}$), ND1.5 ($2.7\times10^{15}$), ND2.0 ($7.3\times10^{14}$), ND2.5 ($3.2\times10^{14}$), ND3.0 ($8.5\times10^{13}$), ND3.5 ($3.8\times10^{13}$), and ND4.0 ($9.5\times10^{12}$).

The multielectrode array recordings were based on the procedures reported by Tian and Copenhagen (2003). Briefly, the retina was dissected and placed photoreceptor side down on a nitrocellulose filter paper strip (Millipore Corp., Bedford, MA). The mounted retina was placed in the MEA-60 multielectrode array recording chamber of 30 μm diameter electrodes spaced 200 μm apart (Multi Channel System MCS GmbH, Reutlingen, Germany), with the ganglion cell layer facing the recording electrodes. The retina was continuously perfused in oxygenated extracellular solution at 34° C. during all experiments. The extracellular solution contained (in mM): NaCl, 124; KCl, 2.5; $CaCl_2$, 2; $MgCl_2$, 2; $NaH_2PO_4$, 1.25; $NaHCO_3$, 26; and glucose, 22 (pH 7.35 with 95% $O_2$ and 5% $CO_2$). Recordings were usually started 60 min after the retina was positioned in the recording chamber. The interval between onsets of each light stimulus was 10-15 s. The signals were filtered between 200 Hz (low cut off) and 20 kHz (high cut off). The responses from individual neurons were analyzed using Offline Sorter software (Plexon, Inc., Dallas, TX).

Figure 3:
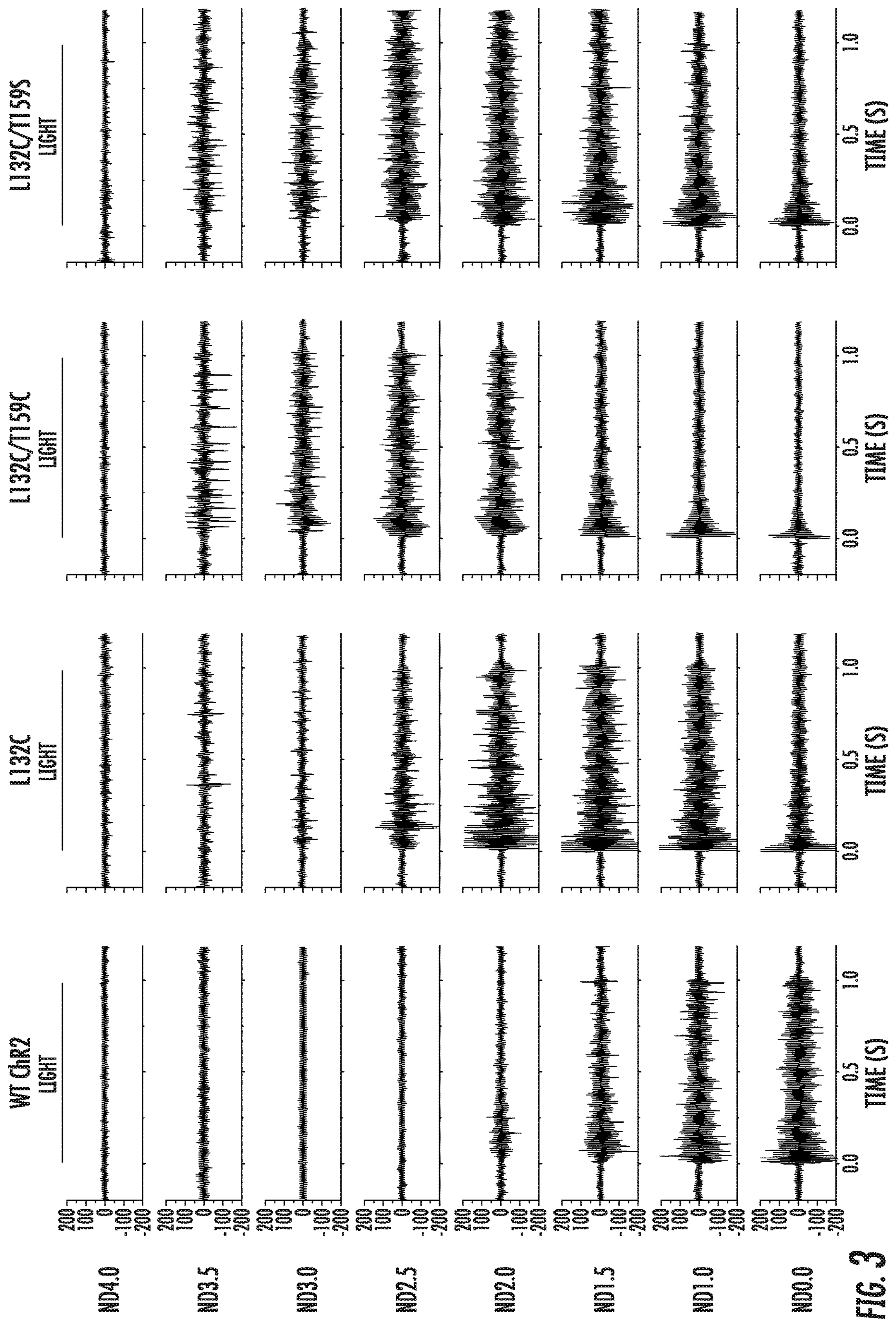
FIG. 3 shows representative multichannel array recordings of WT ChR2, L132C, L132C/T159C, and L132C/T159S mediated spiking activities from retinal ganglion cells in retinal whole-mounts for comparison of their light sensitivity. Light stimuli (photons/cm$^2$/s) was generated by a 473 nm blue laser and attenuated by neutral density filters: ND0 (6.3×10$^{16}$), ND1.0 (7.4×10$^{15}$), ND1.5 (2.7×10$^{15}$), ND2.0 (7.3×10$^{14}$), ND2.5 (3.2×10$^{14}$), ND3.0 (8.5×10$^{13}$), ND3.5 (3.8×10$^{13}$), and ND4.0 (9.5×10$^{12}$).
Figure 4A:
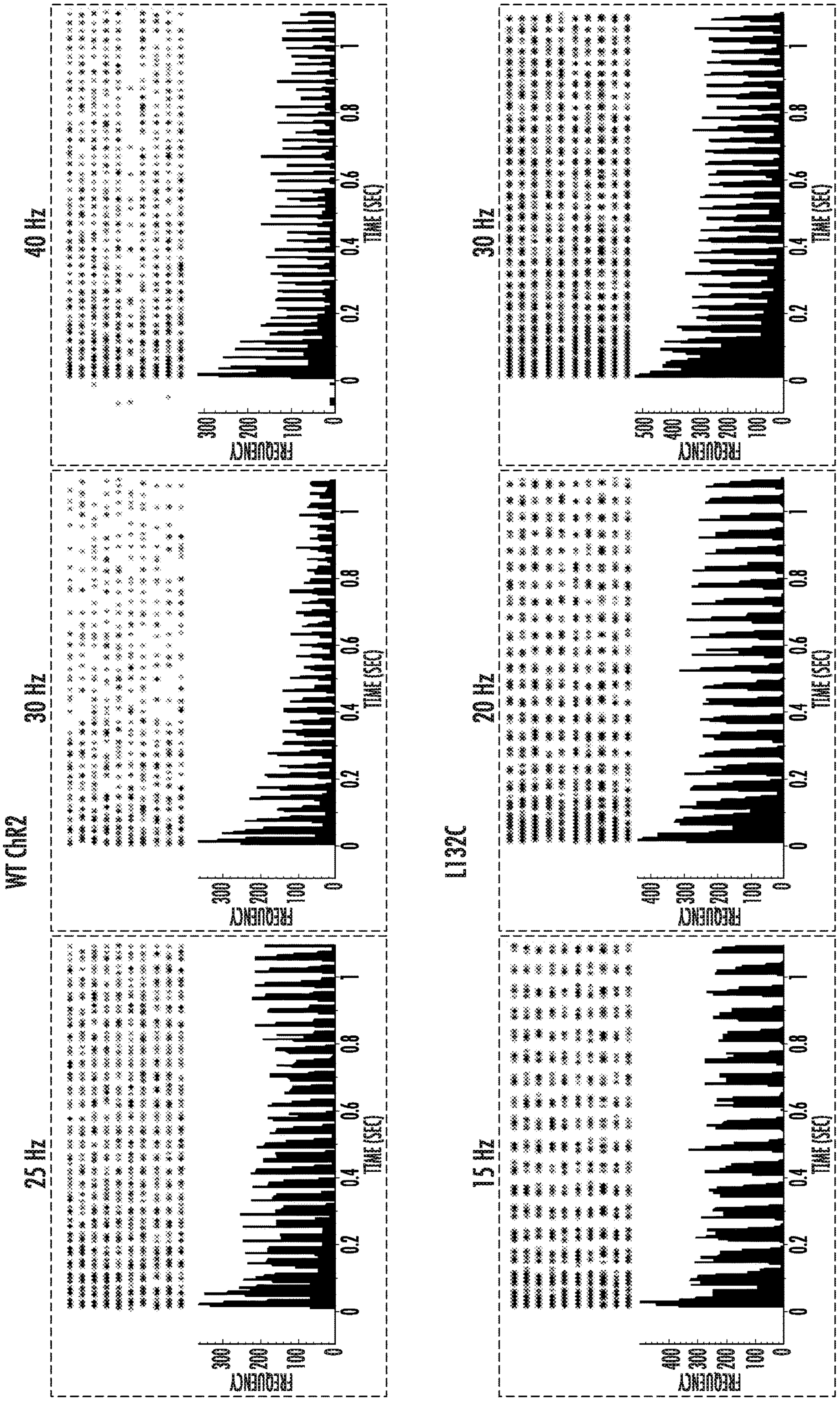
FIG. 4A-B show representative multichannel array recordings of WT ChR2, L132C, L132C/T159C, and L132C/T159S mediated spiking activities from retinal ganglion cells in retinal whole-mounts for comparison of their temporal dynamics. In each panel, the raster plots of 10 consecutive light-elicited spikes originated from a single neuron (top) and the averaged spike rate histograms (bottom) are shown. Light pulses at different frequency was generated by a 473 nm blue laser with intensities about one log unit above the threshold intensity of each mutant. Recordings of WT ChR2 and L132C are shown in FIG. 4A, and recordings of L132C/T159C and L132C/T159S are shown in FIG. 4B.
Figure 4B:
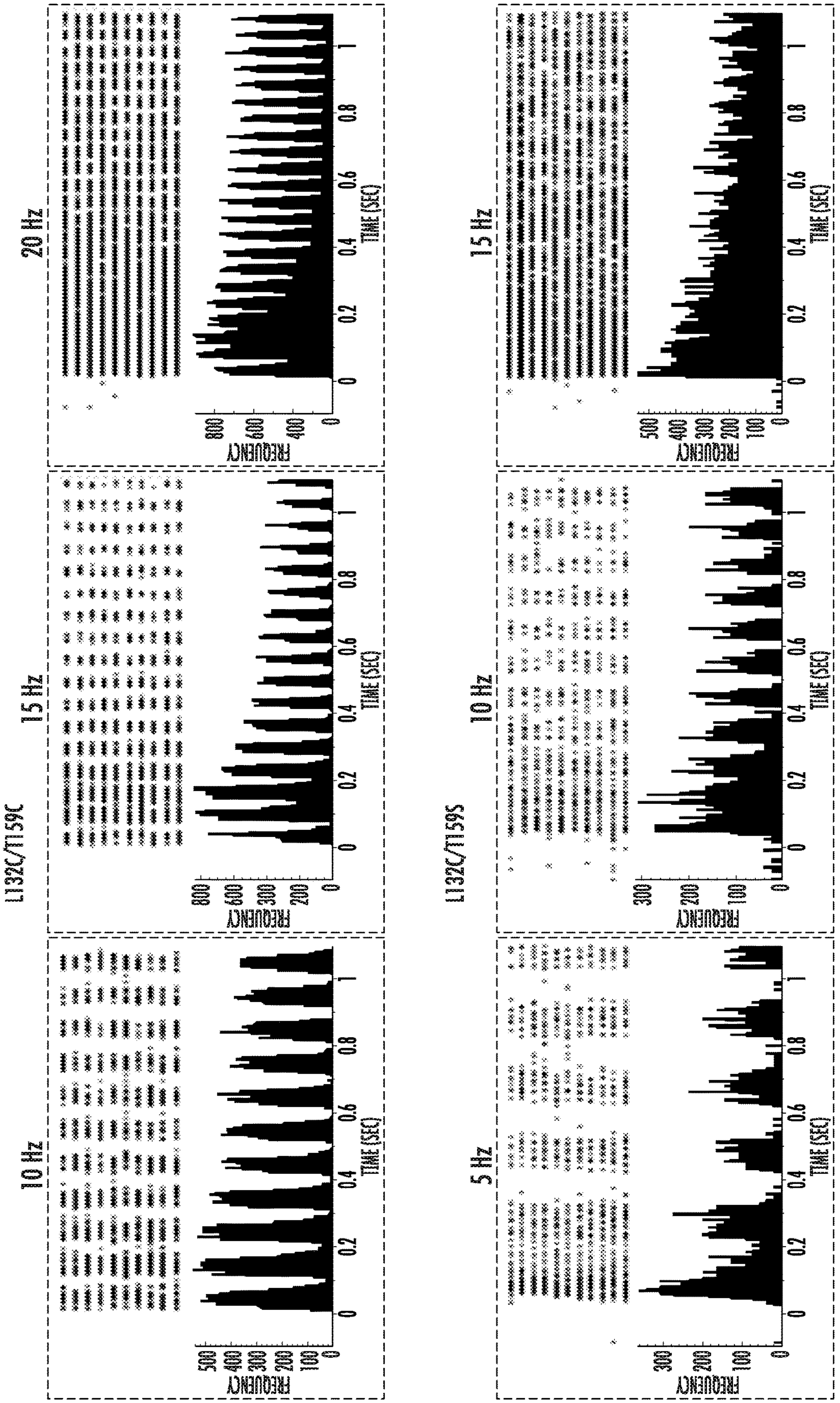

Single mutant Chop2/ChR2 mutants, i.e., L132 and T159C, markedly lower the threshold light intensity that is required to evoke a ChR2-mediated photocurrent. Moreover, several double mutants, including L132C/T159C, L132A/T159C, and L132C/T159S, were found to further increase the photocurrent at low light intensities. Different neutral density filters were used to attenuate the light stimuli to differentiate the light-evoked responses of the Chop2 constructs in low light. Spiking activity of retinal ganglion cells mediated by the mutants of the present invention was observed at the light intensities about 1.5 to 2 log units lower than the light level that is required to elicit the spiking activity with wild-type ChR2 (FIG. 3). Specifically, WT ChR2 exhibited did not exhibit any spiking activity in response to light stimuli with neutral density filter 2.5 ($3.2\times10^{14}$ photons/cm$^2$/s) while ChR2 mutants (L132C, L132C/T159C, and L132C/T159S) demonstrate spiking activity. In fact, the ChR2 mutants still exhibited spiking activity in response to light with neutral density filters 3.0 and 3.5. Therefore, ChR2 mutants of the present invention possess higher light sensitivity and, thus, a markedly lower threshold light intensity that is required to elicit a ChR2-mediated photocurrent. Moreover, ChR2 double mutants possess a higher light sensitivity than single mutants, i.e. L132C. In addition, the spike firing of retinal ganglion cells expressing L132C/T159C and L132/T159S could follow a light flicker frequency of up to 15 Hz and 5 Hz, respectively (FIG. 4).

The L132C/T159A mutant shows high light sensitivity, probably the most light sensitive among these mutants, but it also shows extremely slow off-rate (the channel continue open for many many sends after light off). Interestingly, it can be turned off more quickly using a light with long-wavelengths, such as yellow light. The L132C/T159A mutant (encoded by SEQ ID NOs: 24 and 25) demonstrates significant potential.

Given the trade-off between light sensitivity and channel kinetics, Chop2/ChR2 mutants that demonstrate a balance between light sensitivity and channel kinetics, such as L132C/T159C or L132C/T159S, may be suitable for the application of vision restoration.

Example 4: Analysis of Mutant Chop2 Constructs in Mouse Models of Disease

Mouse models of degenerative ocular diseases are known in the art. For example, homozygous rd1 (rd1/rd1) mice are a commonly used photoreceptor degeneration model. Rd1 mice carry a null mutation in a cyclic GMP phosphodiesterase, PDE6, similar to some forms of retinitis pigmentosa in humans. Other well-established mouse models of ocular disease that may be of particular interest to demonstrate ChR2 mutant safety and efficacy include rds (also known as $Prph^{Rd2}$), rd3, rd4, rd5, rd6, rd7, rd8, rd9, $Pde6b^{rd10}$, or cpfl1 mice.

The Chop2-GFP constructs of the present invention can be injected intravitreally into the eyes of newborn (P1) or adult mice at 2-12 months of age. GFP signal can be observed in the Chop2-GFP-injected retinas, to determine the levels of ChR2 expression or expression in particular populations of cells, such as the retinal ganglion cells. Mutant Chop2-GFP expression can be monitored for a predetermined amount of time, i.e. 3-6 months, or 1 year after viral injection. Patch-clamp and multichannel array recordings can be performed using the methods known in the art and described herein to measure the light-evoked responses of mutant Chop2-GFP-expressing cells in vivo.

Additional techniques and tests are well-established in the art to test for the restoration of light sensitivity or vision. Visual evoked potentials from the Chop2-GFP expressing cells or visual cortex can be examined, as described in PCT publication WO 2007/131180. Other tests include behavioral assessments of the visual acuity in the mice, i.e., virtual optomotor test and visual water maze.

Example 5: Analysis of Long-Term Expression and Safety of Administration of Mutant Chop2 Constructs to Retinal Neurons Neurotoxicity was assessed in C57BL/6J adult mice injected with Chop2 constructs of the present invention. The expression safety of Chop2 mutants in the retina was assessed by immunostaining and cell counting after exposure to strong blue light for two weeks. None of the mice were found to exhibit symptoms of neurotoxicity for up to two months after injection.

Additional ongoing studies are evaluating the long-term expression and safety of Chop2/ChR2 mutants of the invention in retinal neurons.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An expression vector comprising a polynucleotide encoding a channelrhodopsin 2 polypeptide comprising an amino acid sequence of SEQ ID NO: 26 in which the amino acid at position 132 of SEQ ID NO: 26 is cysteine (C) and the amino acid at position 159 of SEQ ID NO: 26 is cysteine (C) or serine(S), wherein the channelrhodopsin 2 polypeptide expressed in a retinal cell has a higher light sensitivity and slower deactivation kinetics compared to that of a polypeptide comprising SEQ ID NO: 26.

2. The expression vector of claim 1, wherein the polypeptide comprises a cysteine (C) at positions 132 and 159 of SEQ ID NO: 26.

3. The expression vector of claim 2, wherein the polypeptide comprises the amino acid sequence of SEQ ID NO: 16 and the polynucleotide comprises the nucleic acid sequence of SEQ ID NO: 15.

4. The expression vector of claim 1, wherein the polypeptide comprises a cysteine (C) at position 132 and a serine(S) at position 159 of SEQ ID NO: 26.

5. The expression vector of claim 4, wherein the polypeptide comprises the amino acid sequence of SEQ ID NO: 19 and the polynucleotide comprises the nucleic acid sequence of SEQ ID NO: 18.

6. The expression vector of claim 1, wherein the expression vector is an adeno-associated virus (AAV) vector.

7. The expression vector of claim 6, wherein the AAV vector is an AAV2 vector.

8. A method of improving vision in a subject suffering from a retinal disease, the method comprising administering to the subject the expression vector of claim 1.

9. The method of claim 8, wherein the subject is suffering from macular degeneration or retinitis pigmentosa.

10. A method of improving vision in a subject suffering from a retinal disease, the method comprising administering to the subject the expression vector of claim 6.

11. The method of claim 10, wherein the subject is suffering from macular degeneration or retinitis pigmentosa.

12. A method of improving vision in a subject suffering from a retinal disease, the method comprising administering to the subject the expression vector of claim 7.

13. The method of claim 12, wherein the subject is suffering from macular degeneration or retinitis pigmentosa.

* * * * *

SEQUENCE LISTING

```
Sequence total quantity: 26
SEQ ID NO: 1            moltype = DNA  length = 3585
FEATURE                 Location/Qualifiers
source                  1..3585
                        mol_type = other DNA
                        organism = Chlamydomonas reinhardtii
SEQUENCE: 1
gcagcaccat acttgacatc tgtcgccaag caagcattaa acatggatta tggaggcgcc  60
ctgagtgccg ttgggcgcga gctgctattt gtaacgaacc cagtagtcgt caatggctct  120
gtacttgtgc ctgaggacca gtgttactgc gcgggctgga ttgagtcgcg tggcacaaac  180
ggtgcccaaa cggcgtcgaa cgtgctgcaa tggcttgctg ctggcttctc catcctactg  240
cttatgtttt acgcctacca aacatggaag tcaacctgcg gctgggagga gatctatgtg  300
tgcgctatcg agatggtcaa ggtgattctc gagttcttct tcgagtttaa gaacccgtcc  360
atgctgtatc tagccacagg ccaccgcgtc cagtggttgc gttacgccga gtggcttctc  420
acctgcccgg tcattctcat tcacctgtca aacctgacgg gcttgtccaa cgactacagc  480
aggcgcacca tgggtctgct tgtgtctgat attggcacaa ttgtgtgggg cgccacttcc  540
gccatggcca ccggatacgt caaggtcatc ttcttctgcc tgggtctgtg ttatggtgct  600
aacacgttct ttcacgctgc caaggcctac atcgagggtt accacaccgt gccgaagggc  660
cggtgtcgcc aggtggtgac tggcatggct tggctcttct tcgtatcatg gggtatgttc  720
cccatcctgt tcatcctcgg ccccgagggc ttcggcgtcc tgagcgtgta cggctccacc  780
gtcggccaca ccatcattga cctgatgtcg aagaactgct ggggtctgct cggccactac  840
ctgcgcgtgc tgatccacga gcatatcctc atccacggcg acattcgcaa gaccaccaaa  900
ttgaacattg gtggcactga gattgaggtc gagacgctgg tggaggacga ggccgaggct  960
ggcgcggtca acaagggcac cggcaagtac gcctcccgcg agtccttcct ggtcatgcgc  1020
gacaagatga aggagaaggg cattgacgtg cgcgcctctc tggacaacag caaggaggtg  1080
gagcaggagc aggccgccag ggctgccatg atgatgatga acggcaatgg catgggtatg  1140
ggaatgggaa tgaacggcat gaacggaatg ggcggtatga acgggatggc tggcggcgcc  1200
aagcccggcc tggagctcac tccgcagcta cagcccggcc gcgtcatcct ggcggtgccg  1260
gacatcagca tggttgactt cttccgcgag cagtttgctc agctatcggt gacgtacgag  1320
ctggtgccgg ccctgggcgc tgacaacaca ctggcgctgg ttacgcaggc gcagaacctg  1380
ggcggcgtgg actttgtgtt gattcacccc gagttcctgc gcgaccgctc tagcaccagc  1440
atcctgagcc gcctgcgcgg cgcgggccag cgtgtggctg cgttcggctg ggcgcagctg  1500
gggcccatgc gtgacctgat cgagtccgca aacctggacg gctggctgga gggcccctcg  1560
ttcggacagg gcatcctgcc ggcccacatc gttgccctgg tggccaagat gcagcagatg  1620
cgcaagatgc agcagatgca gcagattggc atgatgaccg gcggcatgaa cggcatgggc  1680
ggcggtatgg gcggcggcat gaacggcatg ggcggcggca acggcatgaa caacatgggc  1740
aacggcatgg gcggcggcat gggcaacggc atgggcggca atggcatgaa cggaatgggt  1800
ggcggcaacg gcatgaacaa catgggcggc aacggaatgg ccggcaacgg aatgggcggc  1860
ggcatgggcg gcaacggtat gggtggctcc atgaacggca tgagctccgg cgtggtggcc  1920
```

```
aacgtgacgc cctccgccgc cggcggcatg ggcggcatga tgaacggcgg catggctgcg  1980
ccccagtcgc ccggcatgaa cggcggccgc ctgggtacca acccgctctt caacgccgcg  2040
ccctcaccgc tcagctcgca gctcggtgcc gaggcaggca tgggcagcat gggaggcatg  2100
ggcggaatga gcggaatggg aggcatgggt ggaatggggg gcatgggcgg cgccggcgcc  2160
gccacgacgc aggctgcggg cggcaacgcg gaggcggaga tgctgcagaa tctcatgaac  2220
gagatcaatc gcctgaagcg cgagcttggc gagtaaaagg ctggaggccg gtactgcgat  2280
acctgcgagc tcgcgcgcct gactcgtcgt acacacggct caggagcacg cgcgcgtgga  2340
cttctcaacc tgtgtgcaac gtatctagag cggcctgtgc gcgaccgtcc gtgagcattc  2400
cggtgcgatc ttcccgcctt cgcaccgcaa gttcccttcc tggccctgct gcgcctgacg  2460
catcgtccga acggaagggc ggcttgatca gtaaagcatt gaagactgaa gtcgtgcgac  2520
cgtagtgcta tggctctgca cgtaagtggg cgctgccctg cttactacgc attgcccaag  2580
actgcttcct tttggtggcc gaggccctgg tcccacatca ttcatttgca taacgtactg  2640
tttagttaca tacgctttgc ttaacctcga caattgcaac atgggctgag agtccgtacg  2700
gcggctatgg acgaaggtgt tatcggatgt gattaggaat ctcggttgaa aggcttcgag  2760
aaagtgagct tcatctgtgg cttctgttgg ggtcatcaag aagaacgacg gtaaggcaaa  2820
cgaggtaaaa gtggcacgtc tttgtgcaca acgggcccgt ggagagtggg ggagtgcatg  2880
tgtgcggtcc taacacgcga gtgcaaagcg ggcttttctg gagctgggtt acggtctggc  2940
tcggcaactg ctctgtgttt taaccacagc ttcggaagtc tgggtatgtt ttgttggcag  3000
aaacatttgg gtaacttgag ggtgattcgt ctggagtcgg acaacatggc tgccgtccgt  3060
gtgcagggac ggtaatcaat gagctggagc tgtgatgctc accacacgtt gcatacccct  3120
gcttacaaaa acactttgat gtcgtggcca aactatgcgt gagcaaagag ttaaagaggc  3180
atgagtgcat ggttgcggac gtgcgcaaca attgcatcaa gtatttgacg ccttcaagcc  3240
aacaagtgcg cgcgcggcaa cttgattaac acgccggacg cagtggtggg ggcgtgtaca  3300
gtgtttatga gctgccattc tgcgatccgt agtgttaggt tgcgtgtgac gccgcgcggc  3360
tgtgggccct tacatggaga gttgggtgct tcaccacacg gttggcgccg ctgaagggtg  3420
tgctatgttt tggtaaagcc ggggccctga agaccgcaac cgtagaaccg tactgaaagg  3480
gtgtcagccc ggggtaactg gatgccctgg gacatagcta ttaatgttga agtgaagccg  3540
tcaagccgag tgccgtgcgc cgctgtatca ccaaggcccg tccta                  3585

SEQ ID NO: 2            moltype = AA  length = 737
FEATURE                 Location/Qualifiers
source                  1..737
                        mol_type = protein
                        organism = Chlamydomonas reinhardtii
SEQUENCE: 2
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ILIHLSNLTG LSNDYSRRTM GLLVSDIGTI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGKYASRE SFLVMRDKMK EKGIDVRASL DNSKEVEQEQ AARAAMMMMN  360
GNGMGMGMGM NGMNGMGGMN GMAGGAKPGL ELTPQLQPGR VILAVPDISM VDFFREQFAQ  420
LSVTYELVPA LGADNTLALV TQAQNLGGVD FVLIHPEFLR DRSSTSILSR LRGAGQRVAA  480
FGWAQLGPMR DLIESANLDG WLEGPSFGQG ILPAHIVALV AKMQQMRKMQ QMQQIGMMTG  540
GMNGMGGGMG GGMNGMGGGN GMNNMGNGMG GGMGNGMGGN GMNGMGGGNG MNNMGGNGMA  600
GNGMGGGMGG NGMGGSMNGM SSGVVANVTP SAAGGMGGMM NGGMAAPQSP GMNGGRLGTN  660
PLFNAAPSPL SSQLGAEAGM GSMGGMGGMS GMGGMGGMGG MGGAGAATTQ AAGGNAEAEM  720
LQNLMNEINR LKRELGE                                                 737

SEQ ID NO: 3            moltype = DNA  length = 2241
FEATURE                 Location/Qualifiers
source                  1..2241
                        mol_type = other DNA
                        organism = Chlamydomonas reinhardtii
SEQUENCE: 3
gcatctgtcg ccaagcaagc attaaacatg gattatggag gcgccctgag tgccgttggg  60
cgcgagctgc tatttgtaac gaacccagta gtcgtcaatg gctctgtact tgtgcctgag  120
gaccagtgtt actgcgcggg ctggattgag tcgcgtggca caaacggtgc ccaaacggcg  180
tcgaacgtgc tgcaatggct tgctgctggc ttctccatcc tactgcttat gttttacgcc  240
taccaaacat ggaagtcaac ctgcggctgg gaggagatct atgtgtgcgc tatcgagatg  300
gtcaaggtga ttctcgagtt cttcttcgag tttaagaacc cgtccatgct gtatctagcc  360
acaggccacc gcgtccagtg gttgcgttac gccgagtggc ttctcacctg cccggtcatt  420
ctcattcacc tgtcaaacct gacgggcttg tccaacgact acagcaggcg caccatgggt  480
ctgcttgtgt ctgatattgg cacaattgtg tggggcgcca cttccgccat ggccaccgga  540
tacgtcaagg tcatcttctt ctgcctgggt ctgtgttatg gtgctaacac gttctttcac  600
gctgccaagg cctacatcga gggttaccac accgtgccga agggccggtg tcgccaggtg  660
gtgactggca tggcttggct cttcttcgta tcatggggta tgttccccat cctgttcatc  720
ctcggccccg agggcttcgg cgtcctgagc gtgtacggct ccaccgtcgg ccacaccatc  780
attgacctga tgtcgaagaa ctgctggggt ctgctcggcc actacctgcg cgtgctgatc  840
cacgagcata tcctcatcca cggcgacatt cgcaagacca ccaaattgaa cattggtggc  900
actgagattg aggtcgagac gctggtggag gacgaggccg aggctggcgc ggtcaacaag  960
ggcaccggca agtacgcctc ccgcgagtcc ttcctggtca tgcgcgacaa gatgaaggag  1020
aagggcattg acgtgcgcgc ctctctggac aacagcaagg aggtggagca ggagcaggcc  1080
gccagggctg ccatgatgat gatgaacggc aatggcatgg gtatgggaat gggaatgaac  1140
ggcatgaacg gaatgggcgg tatgaacggg atggctggcg gcgccaagcc cggcctggag  1200
ctcactccgc agctacagcc cggccgcgtc atcctggcgg tgccggacat cagcatggtt  1260
gacttcttcc gcgagcagtt tgctcagcta tcggtgacgt acgagctggt gccggccctg  1320
ggcgctgaca acacactggc gctggttacg caggcgcaga acctgggcgg cgtggacttt  1380
gtgttgattc accccgagtt cctgcgcgac cgctctagca ccagcatcct gagccgcctg  1440
```

-continued cgcggcgcgg gccagcgtgt ggctgcgttc ggctgggcgc agctggggcc catgcgtgac 1500
ctgatcgagt ccgcaaacct ggacggctgg ctggagggcc cctcgttcgg acagggcatc 1560
ctgccggccc acatcgttgc cctggtggcc aagatgcagc agatgcgcaa gatgcagcag 1620
atgcagcaga ttggcatgat gaccggcggc atgaacggca tgggcggcgg tatgggcggc 1680
ggcatgaacg gcatgggcgg cggcaacggc atgaacaaca tgggcaacgg catgggcggc 1740
ggcatgggca acggcatggg cggcaatggc atgaacggaa tgggtggcgg caacggcatg 1800
aacaacatgg gcggcaacgg aatggccggc aacggaatgg gcggcggcat gggcggcaac 1860
ggtatgggtg gctccatgaa cggcatgagc tccggcgtgg tggccaacgt gacgccctcc 1920
gccgccggcg gcatgggcgg catgatgaac ggcggcatgg ctgcgcccca gtcgcccggc 1980
atgaacggcg gccgcctggg taccaacccg ctcttcaacg ccgcgccctc accgctcagc 2040
tcgcagctcg gtgccgaggc aggcatgggc agcatgggag gcatgggcgg aatgagcgga 2100
atgggaggca tgggtggaat ggggggcatg ggcggcgccg gcgccgccac gacgcaggct 2160
gcgggcggca acgcggaggc ggagatgctg cagaatctca tgaacgagat caatcgcctg 2220
aagcgcgagc ttggcgagta a 2241

SEQ ID NO: 4 moltype = AA length = 737
FEATURE Location/Qualifiers
source 1..737
mol_type = protein
organism = Chlamydomonas reinhardtii
SEQUENCE: 4
MDYGGALSAV GRELLFVTNP VVVNGSVLVP EDQCYCAGWI ESRGTNGAQT ASNVLQWLAA 60
GFSILLLMFY AYQTWKSTCG WEEIYVCAIE MVKVILEFFF EFKNPSMLYL ATGHRVQWLR 120
YAEWLLTCPV ILIHLSNLTG LSNDYSRRTM GLLVSDIGTI VWGATSAMAT GYVKVIFFCL 180
GLCYGANTFF HAAKAYIEGY HTVPKGRCRQ VVTGMAWLFF VSWGMFPILF ILGPEGFGVL 240
SVYGSTVGHT IIDLMSKNCW GLLGHYLRVL IHEHILIHGD IRKTTKLNIG GTEIEVETLV 300
EDEAEAGAVN KGTGKYASRE SFLVMRDKMK EKGIDVRASL DNSKEVEQEQ AARAAMMMMN 360
GNGMGMGMGM NGMNGMGGMN GMAGGAKPGL ELTPQLQPGR VILAVPDISM VDFFREQFAQ 420
LSVTYELVPA LGADNTLALV TQAQNLGGVD FVLIHPEFLR DRSSTSILSR LRGAGQRVAA 480
FGWAQLGPMR DLIESANLDG WLEGPSFGQG ILPAHIVALV AKMQQMRKMQ QMQQIGMMTG 540
GMNGMGGGMG GGMNGMGGGN GMNNMGNGMG GGMGNGMGGN GMNGMGGGNG MNNMGGNGMA 600
GNGMGGGMGG NGMGGSMNGM SSGVVANVTP SAAGGMGGMM NGGMAAPQSP GMNGGRLGTN 660
PLFNAAPSPL SSQLGAEAGM GSMGGMGGMS GMGGMGGMGG MGGAGAATTQ AAGGNAEAEM 720
LQNLMNEINR LKRELGE 737

SEQ ID NO: 5 moltype = DNA length = 3599
FEATURE Location/Qualifiers
source 1..3599
mol_type = other DNA
organism = Chlamydomonas reinhardtii
SEQUENCE: 5
ttgacatctg tcgccaagca agcattaaac atggattatg gaggcgccct gagtgccgtt 60
gggcgcgagc tgctatttgt aacgaaccca gtagtcgtca atggctctgt acttgtgcct 120
gaggaccagt gttactgcgc gggctggatt gagtcgcgtg gcacaaacgg tgcccaaacg 180
gcgtcgaacg tgctgcaatg gcttgctgct ggcttctcca tcctactgct tatgttttac 240
gcctaccaaa catggaagtc aacctgcggc tgggaggaga tctatgtgtg cgctatcgag 300
atggtcaagg tgattctcga gttcttcttc gagtttaaga acccgtccat gctgtatcta 360
gccacaggcc accgcgtcca gtggttgcgt tacgccgagt ggcttctcac ctgcccggtc 420
attctcattc acctgtcaaa cctgacgggc ttgtccaacg actacagcag gcgcaccatg 480
ggtctgcttg tgtctgatat tggcacaatt gtgtggggcg ccacttccgc catggccacc 540
ggatacgtca aggtcatctt cttctgcctg ggtctgtgtt atggtgctaa cacgttcttt 600
cacgctgcca aggcctacat cgagggttac cacaccgtgc cgaagggccg gtgtcgccag 660
gtggtgactg gcatggcttg gctcttcttc gtatcatggg gtatgttccc catcctgttc 720
atcctcggcc ccgagggctt cggcgtcctg agcgtgtacg gctccaccgt cggccacacc 780
atcattgacc tgatgtcgaa gaactgctgg ggtctgctcg gccactacct gcgcgtgctg 840
atccacgagc atatcctcat ccacggcgac attcgcaaga ccaccaaatt gaacattggt 900
ggcactgaga ttgaggtcga gacgctggtg gaggacgagg ccgaggctgg cgcggtcaac 960
aagggcaccg gcaagtacgc ctcccgcgag tccttcctgg tcatgcgcga caagatgaag 1020
gagaagggca ttgacgtgcg cgcctctctg gacaacagca aggaggtgga gcaggagcag 1080
gccgccaggg ctgccatgat gatgatgaac ggcaatggca tgggtatggg aatgggaatg 1140
aacggcatga acggaatggg cggtatgaac gggatggctg gcggcgccaa gcccggcctg 1200
gagctcactc cgcagctaca gcccggccgc gtcatcctgg cggtgccgga catcagcatg 1260
gttgacttct tccgcgagca gtttgctcag ctatcggtga cgtacgagct ggtgccggcc 1320
ctgggcgctg acaacacact ggcgctggtt acgcaggcgc agaacctggg cggcgtggac 1380
tttgtgttga ttcaccccga gttcctgcgc gaccgctcta gcaccagcat cctgagccgc 1440
ctgcgcggcg cgggccagcg tgtggctgcg ttcggctggg cgcagctggg gcccatgcgt 1500
gacctgatcg agtccgcaaa cctggacggc tggctggagg gcccctcgtt cggacagggc 1560
atcctgccgg cccacatcgt tgccctggtg gccaagatgc agcagatgcg caagatgcag 1620
cagatgcagc agattggcat gatgaccggc ggcatgaacg gcatgggcgg cggtatgggc 1680
ggcggcatga acggcatggg cggcggcaac ggcatgaaca acatgggcaa cggcatgggc 1740
ggcggcatgg gcaacggcat gggcggcaat ggcatgaacg gaatgggtgg cggcaacggc 1800
atgaacaaca tgggcggcaa cggaatggcc ggcaacggaa tgggcggcgg catgggcggc 1860
aacggtatgg gtggctccat gaacggcatg agctccggcg tggtggccaa cgtgacgccc 1920
tccgccgccg gcggcatggg cggcatgatg aacggcggca tggctgcgcc ccagtcgccc 1980
ggcatgaacg gcggccgcct gggtaccaac ccgctcttca acgccgcgcc ctcaccgctc 2040
agctcgcagc tcggtgccga ggcaggcatg ggcagcatgg gaggcatggg cggaatgagc 2100
ggaatgggag gcatgggtgg aatggggggc atgggcggcg ccggcgccgc cacgacgcag 2160
gctgcgggcg gcaacgcgga ggcggagatg ctgcagaatc tcatgaacga gatcaatcgc 2220
ctgaagcgcg agcttggcga gtaaaaggct ggaggccggt actgcgatac ctgcgagctc 2280

```
gcgcgcctga ctcgtcgtac acacggctca ggagcacgcg cgcgtggact tctcaacctg  2340
tgtgcaacgt atctagagcg gcctgtgcgc gaccgtccgt gagcattccg gtgcgatctt  2400
cccgccttcg caccgcaagt tcccttcctg gccctgctgc gcctgacgca tcgtccgaac  2460
ggaagggcgg cttgatcagt aaagcattga agactgaagt cgtgcgaccg tagtgctatg  2520
gctctgcacg taagtgggcg ctgccctgct tactacgcat tgcccaagac tgcttccttt  2580
tggtggccga ggccctggtc ccacatcatt catttgcata acgtactgtt tagttacata  2640
cgctttgctt aacctcgaca attgcaacat gggctgagag tccgtacggc ggctatggac  2700
gaaggtgtta tcggatgtga ttaggaatct cggttgaaag gcttcgagaa agtgagcttc  2760
ttctgtggct tctgttgggg tcatcaagaa gaacgacggt aaggcaaacg aggtaaaagt  2820
ggcacgtctt tgtgcacaac gggcccgtgg agagtggggg agtgcatgtg tgcggtccta  2880
acacgcgagt gcaaagcggg cttttctgga gctgggttac ggtctggctc ggcaactgct  2940
ctgtgtttta accacagctt cggaagtctg ggtatgtttt gttggcagaa acatttgggt  3000
aacttgaggg tgattcgtct ggagtcggac aacatggctg ccgtccgtgt gcagggacgg  3060
taatcaatga agctgaagct gtgatgctca ccacacgttg catacccctg cttacaaaaa  3120
cactttgatg tcgtggccaa actatgcgtg agcaaagagt taaagaggca tgagtgcatg  3180
gttgcggacg tgcgcaacaa ttgcatcaag tatttgacgc cttcaagcca acaagtgcgc  3240
gcgcggcaac ttgattaaca cgccggacgc agtggtgggg gcgtgtacag tgtttatgag  3300
ctgccattct gcgatccgta gtgttaggtt gcgtgtgacg ccgcgcggct gtgggccctt  3360
acatggagag ttgggtgctt caccacacgg ttggcgccgc tgaagggtgt gctatgtttt  3420
ggtaaagccg gggccctgaa gaccgcaacc gtagaaccgt actgaaaggg tgtcagcccg  3480
gggtaactgg atgccctggg acatagctat taatgttgaa gtgaagccgt caagccgagt  3540
gccgtgcgcc gctgtatcac caaggcccgt ccaaaaaaaa aaaaaaaaaa aaaaaaaaa   3599

SEQ ID NO: 6            moltype = AA  length = 737
FEATURE                 Location/Qualifiers
source                  1..737
                        mol_type = protein
                        organism = Chlamydomonas reinhardtii
SEQUENCE: 6
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ILIHLSNLTG LSNDYSRRTM GLLVSDIGTI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGKYASRE SFLVMRDKMK EKGIDVRASL DNSKEVEQEQ AARAAMMMMN  360
GNGMGMGMGM NGMNGMGGMN GMAGGAKPGL ELTPQLQPGR VILAVPDISM VDFFREQFAQ  420
LSVTYELVPA LGADNTLALV TQAQNLGGVD FVLIHPEFLR DRSSTSILSR LRGAGQRVAA  480
FGWAQLGPMR DLIESANLDG WLEGPSFGQG ILPAHIVALV AKMQQMRKMQ QMQQIGMMTG  540
GMNGMGGGMG GGMNGMGGGN GMNNMGNGMG GGMGNGMGGN GMNGMGGGNG MNNMGGNGMA  600
GNGMGGGMGG NGMGGSMNGM SSGVVANVTP SAAGGMGGMM NGGMAAPQSP GMNGGRLGTN  660
PLFNAAPSPL SSQLGAEAGM GSMGGMGGMS GMGGMGGMGG MGGAGAATTQ AAGGNAEAEM  720
LQNLMNEINR LKRELGE                                                737

SEQ ID NO: 7            moltype = DNA  length = 2448
FEATURE                 Location/Qualifiers
source                  1..2448
                        mol_type = other DNA
                        organism = Chlamydomonas reinhardtii
SEQUENCE: 7
catctgtcgc caagcaagca ttaaacatgg attatggagg cgccctgagt gccgttgggc  60
gcgagctgct atttgtaacg aacccagtag tcgtcaatgg ctctgtactt gtgcctgagg  120
accagtgtta ctgcgcgggc tggattgagt cgcgtggcac aaacggtgcc caaacggcgt  180
cgaacgtgct gcaatggctt gctgctggct tctccatcct actgcttatg ttttacgcct  240
accaaacatg gaagtcaacc tgcggctggg aggagatcta tgtgtgcgct atcgagatgg  300
tcaaggtgat tctcgagttc ttcttcgagt ttaagaaccc gtccatgctg tatctagcca  360
caggccaccg cgtccagtgg ttgcgttacg ccgagtggct tctcacctgc ccggtcattc  420
tcattcacct gtcaaacctg acgggcttgt ccaacgacta cagcaggcgc accatgggtc  480
tgcttgtgtc tgatattggc acaattgtgt ggggcgccac ttccgccatg gccaccggat  540
acgtcaaggt catcttcttc tgcctgggtc tgtgttatgg tgctaacacg ttctttcacg  600
ctgccaaggc ctacatcgag ggttaccaca ccgtgccgaa gggccggtgt cgccaggtgg  660
tgactggcat ggcttggctc ttcttcgtat catggggtat gttccccatc ctgttcatcc  720
tcggccccga gggcttcggc gtcctgagcg tgtacggctc caccgtcggc cacaccatca  780
ttgacctgat gtcgaagaac tgctggggtc tgctcggcca ctacctgcgc gtgctgatcc  840
acgagcatat cctcatccac ggcgacattc gcaagaccac caaattgaac attggtggca  900
ctgagattga ggtcgagacg ctggtggagg acgaggccga ggctggcgcg gtcaacaagg  960
gcaccggcaa gtacgcctcc cgcgagtcct tcctggtcat gcgcgacaag atgaaggaga  1020
agggcattga cgtgcgcgcc tctctggaca acagcaagga ggtggagcag gagcaggccg  1080
ccagggctgc catgatgatg atgaacggca atggcatggg tatgggaatg ggaatgaacg  1140
gcatgaacgg aatgggcggt atgaacggga tggctggcgg cgccaagccc ggcctggagc  1200
tcactccgca gctacagccc ggccgcgtca tcctggcggt gccggacatc agcatggttg  1260
acttcttccg cgagcagttt gctcagctat cggtgacgta cgagctggtg ccggccctgg  1320
gcgctgacaa cacactggcg ctggttacgc aggcgcagaa cctgggcggc gtggactttg  1380
tgttgattca ccccgagttc ctgcgcgacc gctctagcac cagcatcctg agccgcctgc  1440
gcggcgcggg ccagcgtgtg gctgcgttcg gctgggcgca gctggggccc atgcgtgacc  1500
tgatcgagtc cgcaaacctg gacggctggc tggagggccc ctcgttcgga cagggcatcc  1560
tgccggccca catcgttgcc ctggtggcca agatgcagca gatgcgcaag atgcagcaga  1620
tgcagcagat tggcatgatg accggcggca tgaacggcat gggcggcggt atgggcggcg  1680
gcatgaacgg catgggcggc ggcaacggca tgaacaacat gggcaacggc atgggcggcg  1740
gcatgggcaa cggcatgggc ggcaatggca tgaacggaat gggtggcggc aacggcatga  1800
```

```
acaacatggg cggcaacgga atggccggca acggaatggg cggcggcatg ggcggcaacg  1860
gtatgggtgg ctccatgaac ggcatgagct ccggcgtggt ggccaacgtg acgccctccg  1920
ccgccggcgg catgggcggc atgatgaacg gcggcatggc tgcgccccag tcgcccggca  1980
tgaacggcgg ccgcctgggt accaacccgc tcttcaacgc cgcgccctca ccgctcagct  2040
cgcagctcgg tgccgaggca ggcatgggca gcatgggagg catgggcgga atgagcggaa  2100
tgggaggcat gggtggaatg gggggcatgg gcggcgccgg cgccgccacg acgcaggctg  2160
cgggcggcaa cgcggaggcg gagatgctgc agaatctcat gaacgagatc aatcgcctga  2220
agcgcgagct tggcgagtaa aaggctggag gccggtactg cgatacctgc gagctcgcgc  2280
gcctgactcg tcgtacacac ggctcaggag cacgcgcgcg tggacttctc aacctgtgtg  2340
caacgtatct agagcggcct gtgcgcgacc gtccgtgagc attccggtgc gatcttcccg  2400
ccttcgcacc gcaagttccc ttcctggccc tgctgcgcct gacgcatc              2448

SEQ ID NO: 8           moltype = AA  length = 737
FEATURE                Location/Qualifiers
source                 1..737
                       mol_type = protein
                       organism = Chlamydomonas reinhardtii
SEQUENCE: 8
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ILIHLSNLTG LSNDYSRRTM GLLVSDIGTI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGKYASRE SFLVMRDKMK EKGIDVRASL DNSKEVEQEQ AARAAMMMMN  360
GNGMGMGMGM NGMNGMGGMN GMAGGAKPGL ELTPQLQPGR VILAVPDISM VDFFREQFAQ  420
LSVTYELVPA LGADNTLALV TQAQNLGGVD FVLIHPEFLR DRSSTSILSR LRGAGQRVAA  480
FGWAQLGPMR DLIESANLDG WLEGPSFGQG ILPAHIVALV AKMQQMRKMQ QMQQIGMMTG  540
GMNGMGGGMG GGMNGMGGGN GMNNMGNGMG GGMGNGMGGN GMNGMGGGNG MNNMGGNGMA  600
GNGMGGGMGG NGMGGSMNGM SSGVVANVTP SAAGGMGGMM NGGMAAPQSP GMNGGRLGTN  660
PLFNAAPSPL SSQLGAEAGM GSMGGMGGMS GMGGMGGMGG MGGAGAATTQ AAGGNAEAEM  720
LQNLMNEINR LKRELGE                                                737

SEQ ID NO: 9           moltype = DNA  length = 3033
FEATURE                Location/Qualifiers
misc_feature           1..3033
                       note = ChR2 mutant
source                 1..3033
                       mol_type = other DNA
                       organism = synthetic construct
SEQUENCE: 9
atggattacc ctgtggcccg gtccctgatt gtaagatacc ccaccgatct gggcaatgga  60
accgtgtgca tgcccagagg acaatgctac tgcgaggggt ggctgaggag ccggggcact  120
agtatcgaaa aaaccatcgc tatcaccctc cagtgggtag tgttcgctct gtccgtagcc  180
tgtctcggct ggtatgcata ccaagcctgg agggctacct gtgggtggga ggaagtatac  240
gtggccctga tcgagatgat gaagtccatc atcgaggctt tccatgagtt cgactcccca  300
gccacactct ggctcagcag tgggaatggc gtagtgtgga tgagatatgg agagtggctg  360
ctgacctgtc ccgtcctgct cattcatctg tccaatctga ccgggctgaa agatgactac  420
tccaagagaa caatgggact gctggtgagt gacgtggggt gtattgtgtg gggagccacc  480
tccgccatgt gcactggatg gaccaagatc ctcttttttcc tgatttccct ctcctatggg  540
atgtatacat acttccacgc cgctaaggtg tatattgagg ccttccacac tgtacctaaa  600
ggcatctgta gggagctcgt gcgggtgatg gcatggacct tctttgtggc ctgggggatg  660
ttccccgtgc tgttcctcct cggcactgag ggatttggcc acattagtcc ttacgggtcc  720
gcaattggac actccatcct ggatctgatt gccaagaata tgtgggggtg gctgggaaat  780
tatctgcggg taaagatcca cgagcatatc ctgctgtatg gcgatatcag aaagaagcag  840
aaaatcacca ttgctggaca ggaaatggag gtggagacac tggtagcaga ggaggaggac  900
gggaccgcgg tcgccaccat ggtgtctaag ggcgaagagc tgattaagga gaacatgcac  960
atgaagctgt acatggaggg caccgtgaac aaccaccact tcaagtgcac atccgagggc  1020
gaaggcaagc cctacgaggg cacccagacc atgagaatca aggtggtcga gggcggccct  1080
ctccccttcg ccttcgacat cctggctacc agcttcatgt acggcagcaa aaccttcatc  1140
aaccacaccc agggcatccc cgacttcttt aagcagtcct tccctgaggg cttcacatgg  1200
gagagagtca ccacatacga agacgggggc gtgctgaccg ctacccagga caccagcctc  1260
caggacggct gcctcatcta caacgtcaag atcagagggg tgaacttccc atccaacggc  1320
cctgtgatgc agaagaaaac actcggctgg gaggcctcca ccgagatgct gtaccccgct  1380
gacggcggcc tggaaggcag agccgacatg gccctgaagc tcgtgggcgg gggccacctg  1440
atctgcaact tgaagaccac atacagatcc aagaaacccg ctaagaacct caagatgccc  1500
ggcgtctact atgtggacag aagactggaa agaatcaagg aggccgacaa agagacctac  1560
gtcgagcagc acgaggtggc tgtggccaga tactgcgacc tccctagcaa actggggcac  1620
aaacttaatt gcctgcagga gaagaagtca tgcagccagc gcatggccga attccggcaa  1680
tactgttgga acccggacac tgggcagatg ctgggccgca ccccagcccg gtgggtgtgg  1740
atcagcctgt actatgcagc tttctacgtg gtcatgactg ggctctttgc cttgtgcatc  1800
tatgtgctga tgcagaccat tgatccctac acccccgact accaggacca gttaaagtca  1860
ccgggggtaa ccttgagacc ggatgtgtat ggggaaagag ggctgcagat ttcctacaac  1920
atctctgaaa acagctctag acaggcccag atcaccggac gtccggagac tgagacattg  1980
ccaccggtgg actacggggg ggccctgagc gctgtgggca gagaactcct gttcgtgaca  2040
aatccagtcg tggtgaacgg ctccgtactc gtacccgagg atcagtgcta ttgcgcagga  2100
tggatcgaga gcagaggcac aaacggcgca cagactgcat ccaacgtgct ccagtggttg  2160
gccgcaggct tttccattct cctgctcatg ttttacgcct accagacttg gaagtccaca  2220
tgtggctggg aggaaatcta cgtgtgtgca atcgaaatgg tgaaggtgat cctggagttt  2280
ttcttcgaat ttaaaaaccc aagcatgctg tacctggcta ctggccacag agtgcagtgg  2340
```

```
ctgcggtatg ccgaatggct gctgacttgc ccagtgattt gcatccacct gtccaacctg  2400
actgggctgt ctaacgatta cagtaggaga acaatgggac tgctcgtatc cgacatcggc  2460
actatcgtat ggggcgcaac tagtgccatg gccactggat acgtgaaagt gatcttcttc  2520
tgcctgggac tctgctacgg agcaaacaca ttttttcatg ccgcaaaagc atatatcgag  2580
gggtatcata ccgtcccaaa gggccggtgt agacaagtgg tgactggcat ggcttggctg  2640
ttcttcgtgt cctgggggat gtttcccatc ctctttatcc tgggcccaga aggcttcggg  2700
gtgctgagtg tgtatggcag taccgtagga cacactatca ttgacctgat gagcaaaaac  2760
tgctgggggc tgctcggcca ctacctgaga gtactcatcc acgagcatat cctgattcat  2820
ggcgatatcc ggaaaactac caagctcaat atcgggggca ccgagattga agtggagaca  2880
ctcgtggagg acgaggccga ggccggagca gtgaacaaag gcactggcaa gtatgcctcc  2940
agagaatcct ttctggtgat gcgggacaaa atgaaggaga aaggcattga tgtacggtgc  3000
agtaatgcca aagccgtcga gactgatgtg tag                               3033
```

```
SEQ ID NO: 10          moltype = AA  length = 1010
FEATURE                Location/Qualifiers
REGION                 1..1010
                       note = ChR2 mutant
source                 1..1010
                       mol_type = protein
                       organism = synthetic construct
SEQUENCE: 10
MDYPVARSLI VRYPTDLGNG TVCMPRGQCY CEGWLRSRGT SIEKTIAITL QWVVFALSVA  60
CLGWYAYQAW RATCGWEEVY VALIEMMKSI IEAFHEFDSP ATLWLSSGNG VVWMRYGEWL  120
LTCPVLLIHL SNLTGLKDDY SKRTMGLLVS DVGCIVWGAT SAMCTGWTKI LFFLISLSYG  180
MYTYFHAAKV YIEAFHTVPK GICRELVRVM AWTFFVAWGM FPVLFLLGTE GFGHISPYGS  240
AIGHSILDLI AKNMWGVLGN YLRVKIHEHI LLYGDIRKKQ KITIAGQEME VETLVAEEED  300
GTAVATMVSK GEELIKENMH MKLYMEGTVN NHHFKCTSEG EGKPYEGTQT MRIKVVEGGP  360
LPFAFDILAT SFMYGSKTFI NHTQGIPDFF KQSFPEGFTW ERVTTYEDGG VLTATQDTSL  420
QDGCLIYNVK IRGVNFPSNG PVMQKKTLGW EASTEMLYPA DGGLEGRADM ALKLVGGGHL  480
ICNLKTTYRS KKPAKNLKMP GVYYVDRRLE RIKEADKETY VEQHEVAVAR YCDLPSKLGH  540
KLNCLQEKKS CSQRMAEFRQ YCWNPDTGQM LGRTPARWVW ISLYYAAFYV VMTGLFALCI  600
YVLMQTIDPY TPDYQDQLKS PGVTLRPDVY GERGLQISYN ISENSSRQAQ ITGRPETETL  660
PPVDYGGALS AVGRELLFVT NPVVVNGSVL VPEDQCYCAG WIESRGTNGA QTASNVLQWL  720
AAGFSILLLM FYAYQTWKST CGWEEIYVCA IEMVKVILEF FFEFKNPSML YLATGHRVQW  780
LRYAEWLLTC PVICIHLSNL TGLSNDYSRR TMGLLVSDIG TIVWGATSAM ATGYVKVIFF  840
CLGLCYGANT FFHAAKAYIE GYHTVPKGRC RQVVTGMAWL FFVSWGMFPI LFILGPEGFG  900
VLSVYGSTVG HTIIDLMSKN CWGLLGHYLR VLIHEHILIH GDIRKTTKLN IGGTEIEVET  960
LVEDEAEAGA VNKGTGKYAS RESFLVMRDK MKEKGIDVRC SNAKAVETDV              1010
```

```
SEQ ID NO: 11          moltype = DNA  length = 3033
FEATURE                Location/Qualifiers
misc_feature           1..3033
                       note = ChR2 mutant
source                 1..3033
                       mol_type = other DNA
                       organism = synthetic construct
SEQUENCE: 11
atggattacc ctgtggcccg gtccctgatt gtaagatacc ccaccgatct gggcaatgga  60
accgtgtgca tgcccagagg acaatgctac tgcgaggggt ggctgaggag ccggggcact  120
agtatcgaaa aaaccatcgc tatcaccctc cagtgggtag tgttcgctct gtccgtagcc  180
tgtctcggct ggtatgcata ccaagcctgg agggctacct gtgggtggga ggaagtatac  240
gtggccctga tcgagatgat gaagtccatc atcgaggctt tccatgagtt cgactcccca  300
gccacactct ggctcagcag tgggaatggc gtagtgtgga tgagatatgg agagtggctg  360
ctgacctgtc ccgtcctgct cattcatctg tccaatctga ccgggctgaa agatgactac  420
tccaagagaa caatgggact gctggtgagt gacgtggggt gtattgtgtg gggagccacc  480
tccgccatgt gcactggatg gaccaagatc ctctttttcc tgatttccct ctcctatggg  540
atgtatacat acttccacgc cgctaaggtg tatattgagg ccttccacac tgtacctaaa  600
ggcatctgta gggagctcgt gcgggtgatg gcatggacct tctttgtggc ctggggggatg  660
ttccccgtgc tgttcctcct cggcactgag ggatttggcc acattagtcc ttacgggtcc  720
gcaattggac actccatcct ggatctgatt gccaagaata tgtggggggt gctgggaaat  780
tatctgcggg taaagatcca cgagcatatc ctgctgtatg gcgatatcag aaagaagcag  840
aaaatcacca ttgctggaca ggaaatggag gtggagacac tggtagcaga ggaggaggac  900
gggaccgcgg tcgccaccat ggtgtctaag ggcgaagagc tgattaagga gaacatgcac  960
atgaagctgt acatggaggg caccgtgaac aaccaccact tcaagtgcac atccgagggc  1020
gaaggcaagc cctacgaggg cacccagacc atgagaatca aggtggtcga gggcggccct  1080
ctccccttcg ccttcgacat cctggctacc agcttcatgt acggcagcaa aaccttcatc  1140
aaccacaccc agggcatccc cgacttcttt aagcagtcct tccctgaggg cttcacatgg  1200
gagagagtca ccacatacga agacgggggc gtgctgaccg ctacccagga caccagcctc  1260
caggacggct gcctcatcta caacgtcaag atcagagggg tgaacttccc atccaacggc  1320
cctgtgatgc agaagaaaac actcggctgg gaggcctcca ccgagatgct gtaccccgct  1380
gacggcggcc tggaaggcag agccgacatg gccctgaagc tcgtgggcgg gggccacctg  1440
atctgcaact tgaagaccac atacagatcc aagaaacccg ctaagaacct caagatgccc  1500
ggcgtctact atgtggacag aagactggaa agaatcaagg aggccgacaa agagacctac  1560
gtcgagcagc acgaggtggc tgtggccaga tactgcgacc tccctagcaa actggggcac  1620
aaacttaatt gcctgcagga gaagaagtca tgcagccagc gcatggccga attccggcaa  1680
tactgttgga acccggacac tgggcagatg ctgggccgca ccccagcccg gtgggtgtgg  1740
atcagcctgt actatgcagc tttctacgtg gtcatgactg ggctctttgc cttgtgcatc  1800
tatgtgctga tgcagaccat tgatccctac acccccgact accaggacca gttaaagtca  1860
ccgggggtaa ccttgagacc ggatgtgtat ggggaaagag ggctgcagat ttcctacaac  1920
```

```
atctctgaaa acagctctag acaggcccag atcaccggac gtccggagac tgagacattg  1980
ccaccggtgg actacggggg ggccctgagc gctgtgggca gagaactcct gttcgtgaca  2040
aatccagtcg tggtgaacgg ctccgtactc gtacccgagg atcagtgcta ttgcgcagga  2100
tggatcgaga gcagaggcac aaacggcgca cagactgcat ccaacgtgct ccagtggttg  2160
gccgcaggct tttccattct cctgctcatg ttttacgcct accagacttg gaagtccaca  2220
tgtggctggg aggaaatcta cgtgtgtgca atcgaaatgg tgaaggtgat cctggagttt  2280
ttcttcgaat ttaaaaaccc aagcatgctg tacctggcta ctggccacag agtgcagtgg  2340
ctgcggtatg ccgaatggct gctgacttgc ccagtgattc tgatccacct gtccaacctg  2400
actgggctgt ctaacgatta cagtaggaga acaatgggac tgctcgtatc cgacatcggc  2460
actatcgtat ggggcgcaac tagtgccatg gccactggat acgtgaaagt gatcttcttc  2520
tgcctgggac tctgctacgg agcaaacaca ttttttcatg ccgcaaaagc atatatcgag  2580
gggtatcata ccgtcccaaa gggccggtgt agacaagtgg tgactggcat ggcttggctg  2640
ttcttcgtgt cctgggggat gtttcccatc ctctttatcc tgggcccaga aggcttcggg  2700
gtgctgagtg tgtatggcag taccgtagga cacactatca ttgacctgat gagcaaaaac  2760
tgctgggggc tgctcggcca ctacctgaga gtactcatcc acgagcatat cctgattcat  2820
ggcgatatcc ggaaaactac caagctcaat atcgggggca ccgagattga agtggagaca  2880
ctcgtggagg acgaggccga ggccggagca gtgaacaaag gcactggcaa gtatgcctcc  2940
agagaatcct ttctggtgat gcgggacaaa atgaaggaga aaggcattga tgtacggtgc  3000
agtaatgcca aagccgtcga gactgatgtg tag                               3033

SEQ ID NO: 12          moltype = AA  length = 1010
FEATURE                Location/Qualifiers
REGION                 1..1010
                       note = ChR2 mutant construct
source                 1..1010
                       mol_type = protein
                       organism = synthetic construct
SEQUENCE: 12
MDYPVARSLI VRYPTDLGNG TVCMPRGQCY CEGWLRSRGT SIEKTIAITL QWVVFALSVA  60
CLGWYAYQAW RATCGWEEVY VALIEMMKSI IEAFHEFDSP ATLWLSSGNG VVWMRYGEWL  120
LTCPVLLIHL SNLTGLKDDY SKRTMGLLVS DVGCIVWGAT SAMCTGWTKI LFFLISLSYG  180
MYTYFHAAKV YIEAFHTVPK GICRELVRVM AWTFFVAWGM FPVLFLLGTE GFGHISPYGS  240
AIGHSILDLI AKNMWGVLGN YLRVKIHEHI LLYGDIRKKQ KITIAGQEME VETLVAEEED  300
GTAVATMVSK GEELIKENMH MKLYMEGTVN NHHFKCTSEG EGKPYEGTQT MRIKVVEGGP  360
LPFAFDILAT SFMYGSKTFI NHTQGIPDFF KQSFPEGFTW ERVTTYEDGG VLTATQDTSL  420
QDGCLIYNVK IRGVNFPSNG PVMQKKTLGW EASTEMLYPA DGGLEGRADM ALKLVGGGHL  480
ICNLKTTYRS KKPAKNLKMP GVYYVDRRLE RIKEADKETY VEQHEVAVAR YCDLPSKLGH  540
KLNCLQEKKS CSQRMAEFRQ YCWNPDTGQM LGRTPARWVW ISLYYAAFYV VMTGLFALCI  600
YVLMQTIDPY TPDYQDQLKS PGVTLRPDVY GERGLQISYN ISENSSRQAQ ITGRPETETL  660
PPVDYGGALS AVGRELLFVT NPVVVNGSVL VPEDQCYCAG WIESRGTNGA QTASNVLQWL  720
AAGFSILLLM FYAYQTWKST CGWEEIYVCA IEMVKVILEF FFEFKNPSML YLATGHRVQW  780
LRYAEWLLTC PVILIHLSNL TGLSNDYSRR TMGLLVSDIG TIVWGATSAM ATGYVKVIFF  840
CLGLCYGANT FFHAAKAYIE GYHTVPKGRC RQVVTGMAWL FFVSWGMFPI LFILGPEGFG  900
VLSVYGSTVG HTIIDLMSKN CWGLLGHYLR VLIHEHILIH GDIRKTTKLN IGGTEIEVET  960
LVEDEAEAGA VNKGTGKYAS RESFLVMRDK MKEKGIDVRC SNAKAVETDV             1010

SEQ ID NO: 13          moltype = AA  length = 315
FEATURE                Location/Qualifiers
REGION                 1..315
                       note = ChR2 mutant construct
source                 1..315
                       mol_type = protein
                       organism = synthetic construct
SEQUENCE: 13
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ICIHLSNLTG LSNDYSRRTM GLLVSDIGTI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                   315

SEQ ID NO: 14          moltype = AA  length = 315
FEATURE                Location/Qualifiers
REGION                 1..315
                       note = ChR2 mutant construct
source                 1..315
                       mol_type = protein
                       organism = synthetic construct
SEQUENCE: 14
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ILIHLSNLTG LSNDYSRRTM GLLVSDIGCI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                   315
```

```
SEQ ID NO: 15          moltype = DNA  length = 945
FEATURE                Location/Qualifiers
misc_feature           1..945
                       note = ChR2 mutant construct
source                 1..945
                       mol_type = other DNA
                       organism = synthetic construct
SEQUENCE: 15
atggactacg ggggggctct gtctgctgtc gggagggaac tgctgtttgt gactaaccct  60
gtcgtcgtga acgggagtgt gctggtccct gaggaccagt gctactgtgc cggctggatc  120
gaatcacgcg gaaccaacgg ggcccagaca gctagcaatg tgctgcagtg gctggccgct  180
gggtttagta tcctgctgct gatgttctac gcctatcaga cttggaagtc aacctgcggc  240
tgggaggaaa tctacgtgtg cgctattgag atggtgaaag tgatcctgga gttcttcttc  300
gagttcaaga acccaagcat gctgtacctg gctactggac accgagtgca gtggctgaga  360
tatgcagaat ggctgctgac atgccccgtc atctgcattc acctgtccaa cctgacaggc  420
ctgagcaatg actactccag gagaactatg ggactgctgg tgtccgacat cggctgcatt  480
gtctggggag caacttctgc tatggcaacc ggatacgtga aggtcatctt tttctgcctg  540
gggctgtgct atggcgcaaa tacctttttc cacgcagcca aggcctacat tgaggggtat  600
cataccgtgc caaaaggccg gtgccgacag gtggtcacag gaatggcttg gctgtttttc  660
gtctcttggg gaatgtttcc catcctgttc attctggggc ctgaagggtt cggcgtgctg  720
tctgtctacg gaagtacagt ggggcatact atcattgacc tgatgtccaa aaactgttgg  780
ggcctgctgg gacactatct gagagtgctg atccacgagc atatcctgat tcatggcgat  840
attcggaaga ccacaaaact gaatatcggc ggaaccgaga ttgaagtgga aacactggtg  900
gaagacgagg ctgaggctgg ggctgtgaac aaggggactg gcaaa                945

SEQ ID NO: 16          moltype = AA  length = 315
FEATURE                Location/Qualifiers
REGION                 1..315
                       note = mutated Chop2
source                 1..315
                       mol_type = protein
                       organism = synthetic construct
SEQUENCE: 16
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ICIHLSNLTG LSNDYSRRTM GLLVSDIGCI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                 315

SEQ ID NO: 17          moltype = AA  length = 315
FEATURE                Location/Qualifiers
REGION                 1..315
                       note = mutated Chop2
source                 1..315
                       mol_type = protein
                       organism = synthetic construct
SEQUENCE: 17
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ILIHLSNLTG LSNDYSRRTM GLLVSDIGSI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                 315

SEQ ID NO: 18          moltype = DNA  length = 945
FEATURE                Location/Qualifiers
misc_feature           1..945
                       note = mutated Chop2
source                 1..945
                       mol_type = other DNA
                       organism = synthetic construct
SEQUENCE: 18
atggactacg ggggggctct gtctgctgtc gggagggaac tgctgtttgt gactaaccct  60
gtcgtcgtga acgggagtgt gctggtccct gaggaccagt gctactgtgc cggctggatc  120
gaatcacgcg gaaccaacgg ggcccagaca gctagcaatg tgctgcagtg gctggccgct  180
gggtttagta tcctgctgct gatgttctac gcctatcaga cttggaagtc aacctgcggc  240
tgggaggaaa tctacgtgtg cgctattgag atggtgaaag tgatcctgga gttcttcttc  300
gagttcaaga acccaagcat gctgtacctg gctactggac accgagtgca gtggctgaga  360
tatgcagaat ggctgctgac atgccccgtc atctgcattc acctgtccaa cctgacaggc  420
ctgagcaatg actactccag gagaactatg ggactgctgg tgtccgacat cggcagcatt  480
gtctggggag caacttctgc tatggcaacc ggatacgtga aggtcatctt tttctgcctg  540
gggctgtgct atggcgcaaa tacctttttc cacgcagcca aggcctacat tgaggggtat  600
cataccgtgc caaaaggccg gtgccgacag gtggtcacag gaatggcttg gctgtttttc  660
gtctcttggg gaatgtttcc catcctgttc attctggggc ctgaagggtt cggcgtgctg  720
tctgtctacg gaagtacagt ggggcatact atcattgacc tgatgtccaa aaactgttgg  780
```

```
ggcctgctgg gacactatct gagagtgctg atccacgagc atatcctgat tcatggcgat  840
attcggaaga ccacaaaact gaatatcggc ggaaccgaga ttgaagtgga aacactggtg  900
gaagacgagg ctgaggctgg ggctgtgaac aaggggactg gcaaa                   945

SEQ ID NO: 19          moltype = AA  length = 315
FEATURE                Location/Qualifiers
REGION                 1..315
                       note = mutated Chop2
source                 1..315
                       mol_type = protein
                       organism = synthetic construct
SEQUENCE: 19
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ICIHLSNLTG LSNDYSRRTM GLLVSDIGSI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                    315

SEQ ID NO: 20          moltype = AA  length = 315
FEATURE                Location/Qualifiers
REGION                 1..315
                       note = mutated Chop2
source                 1..315
                       mol_type = protein
                       organism = synthetic construct
SEQUENCE: 20
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV IAIHLSNLTG LSNDYSRRTM GLLVSDIGTI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                    315

SEQ ID NO: 21          moltype = DNA  length = 945
FEATURE                Location/Qualifiers
misc_feature           1..945
                       note = mutated Chop2
source                 1..945
                       mol_type = other DNA
                       organism = synthetic construct
SEQUENCE: 21
atggactacg ggggggctct gtctgctgtc gggagggaac tgctgtttgt gactaaccct  60
gtcgtcgtga acgggagtgt gctggtccct gaggaccagt gctactgtgc cggctggatc  120
gaatcacgcg gaaccaacgg ggcccagaca gctagcaatg tgctgcagtg gctggccgct  180
gggtttagta tcctgctgct gatgttctac gcctatcaga cttggaagtc aacctgcggc  240
tgggaggaaa tctacgtgtg cgctattgag atggtgaaag tgatcctgga gttcttcttc  300
gagttcaaga acccaagcat gctgtacctg gctactggac accgagtgca gtggctgaga  360
tatgcagaat ggctgctgac atgccccgtc atcgccattc acctgtccaa cctgacaggc  420
ctgagcaatg actactccag gagaactatg ggactgctgg tgtccgacat cggctgcatt  480
gtctggggag caacttctgc tatggcaacc ggatacgtga aggtcatctt tttctgcctg  540
gggctgtgct atggcgcaaa tacctttttc cacgcagcca aggcctacat tgaggggtat  600
cataccgtgc caaaaggccg gtgccgacag gtggtcacag gaatggcttg gctgtttttc  660
gtctcttggg gaatgtttcc catcctgttc attctggggc ctgaagggtt cggcgtgctg  720
tctgtctacg gaagtacagt ggggcatact atcattgacc tgatgtccaa aaactgttgg  780
ggcctgctgg gacactatct gagagtgctg atccacgagc atatcctgat tcatggcgat  840
attcggaaga ccacaaaact gaatatcggc ggaaccgaga ttgaagtgga aacactggtg  900
gaagacgagg ctgaggctgg ggctgtgaac aaggggactg gcaaa                   945

SEQ ID NO: 22          moltype = AA  length = 315
FEATURE                Location/Qualifiers
REGION                 1..315
                       note = mutated Chop2
source                 1..315
                       mol_type = protein
                       organism = synthetic construct
SEQUENCE: 22
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV IAIHLSNLTG LSNDYSRRTM GLLVSDIGCI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                    315

SEQ ID NO: 23          moltype = AA  length = 315
FEATURE                Location/Qualifiers
REGION                 1..315
                       note = mutated Chop2
```

-continued

```
source                1..315
                      mol_type = protein
                      organism = synthetic construct
SEQUENCE: 23
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ILIHLSNLTG LSNDYSRRTM GLLVSDIGAI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                  315

SEQ ID NO: 24         moltype = DNA  length = 945
FEATURE               Location/Qualifiers
misc_feature          1..945
                      note = mutated Chop2
source                1..945
                      mol_type = other DNA
                      organism = synthetic construct
SEQUENCE: 24
atggactacg ggggggctct gtctgctgtc gggagggaac tgctgtttgt gactaaccct  60
gtcgtcgtga acgggagtgt gctggtccct gaggaccagt gctactgtgc cggctggatc  120
gaatcacgcg gaaccaacgg ggcccagaca gctagcaatg tgctgcagtg gctggccgct  180
gggtttagta tcctgctgct gatgttctac gcctatcaga cttggaagtc aacctgcggc  240
tgggaggaaa tctacgtgtg cgctattgag atggtgaaag tgatcctgga gttcttcttc  300
gagttcaaga acccaagcat gctgtacctg gctactggac accgagtgca gtggctgaga  360
tatgcagaat ggctgctgac atgccccgtc atctgcattc acctgtccaa cctgacaggc  420
ctgagcaatg actactccag gagaactatg ggactgctgg tgtccgacat cggcgccatt  480
gtctggggag caacttctgc tatggcaacc ggatacgtga aggtcatctt tttctgcctg  540
gggctgtgct atggcgcaaa taccttttttc cacgcagcca aggcctacat tgaggggtat  600
cataccgtgc caaaaggccg gtgccgacag gtggtcacag gaatggcttg gctgtttttc  660
gtctcttggg gaatgtttcc catcctgttc attctggggc ctgaagggtt cggcgtgctg  720
tctgtctacg gaagtacagt ggggcatact atcattgacc tgatgtccaa aaactgttgg  780
ggcctgctgg gacactatct gagagtgctg atccacgagc atatcctgat tcatggcgat  840
attcggaaga ccacaaaact gaatatcggc ggaaccgaga ttgaagtgga aacactggtg  900
gaagacgagg ctgaggctgg ggctgtgaac aaggggactg gcaaa                 945

SEQ ID NO: 25         moltype = AA  length = 315
FEATURE               Location/Qualifiers
REGION                1..315
                      note = mutated Chop2
source                1..315
                      mol_type = protein
                      organism = synthetic construct
SEQUENCE: 25
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ICIHLSNLTG LSNDYSRRTM GLLVSDIGAI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                  315

SEQ ID NO: 26         moltype = AA  length = 315
FEATURE               Location/Qualifiers
REGION                1..315
                      note = ChR2 mutant construct
source                1..315
                      mol_type = protein
                      organism = synthetic construct
SEQUENCE: 26
MDYGGALSAV GRELLFVTNP VVVNGSVLVP EDQCYCAGWI ESRGTNGAQT ASNVLQWLAA  60
GFSILLLMFY AYQTWKSTCG WEEIYVCAIE MVKVILEFFF EFKNPSMLYL ATGHRVQWLR  120
YAEWLLTCPV ILIHLSNLTG LSNDYSRRTM GLLVSDIGTI VWGATSAMAT GYVKVIFFCL  180
GLCYGANTFF HAAKAYIEGY HTVPKGRCRQ VVTGMAWLFF VSWGMFPILF ILGPEGFGVL  240
SVYGSTVGHT IIDLMSKNCW GLLGHYLRVL IHEHILIHGD IRKTTKLNIG GTEIEVETLV  300
EDEAEAGAVN KGTGK                                                  315
```